US012322480B2

(12) United States Patent (10) Patent No.: US 12,322,480 B2
Malfait et al. (45) Date of Patent: Jun. 3, 2025

(54) GRAPHICAL STUDY DESIGN FOR CLINICAL RESEARCH STUDY SYSTEMS

(71) Applicant: Nurocor, Inc., Austin, TX (US)

(72) Inventors: Frederik Malfait, Wolfenschiessen (CH); Maurice Williams, Canton, MI (US); Robert Ross, Lumberton, NJ (US)

(73) Assignee: Nurocor, Inc., Austin, TX (US)

( * ) Notice: Subject to any disclaimer, the term of this patent is extended or adjusted under 35 U.S.C. 154(b) by 877 days.

(21) Appl. No.: 17/305,372

(22) Filed: Jul. 6, 2021

(65) Prior Publication Data
US 2022/0005555 A1    Jan. 6, 2022

Related U.S. Application Data

(60) Provisional application No. 63/198,657, filed on Nov. 2, 2020, provisional application No. 63/048,375, filed on Jul. 6, 2020.

(51) Int. Cl.
*G06F 16/901* (2019.01)
*G06F 3/0486* (2013.01)
(Continued)

(52) U.S. Cl.
CPC .......... *G16H 10/20* (2018.01); *G06F 3/0486* (2013.01); *G06F 8/34* (2013.01); *G06F 16/211* (2019.01);
(Continued)

(58) Field of Classification Search
CPC ........ G16H 10/20; G16H 10/60; G16H 40/60; G16H 50/20; G06F 3/0486; G06F 8/34;
(Continued)

(56) References Cited

U.S. PATENT DOCUMENTS 8,041,735 B1    10/2011 Lacapra et al.
8,527,920 B1    9/2013 Choudhury et al.
(Continued)

FOREIGN PATENT DOCUMENTS

WO    2014033747 A2    3/2014

OTHER PUBLICATIONS

"Clinical trials and their patients: The rising costs and how to stem the loss," Pharmafile, accessed from http:/www.pharmafile.com/print/511225, Mar. 11, 2016, 6 pp.
(Continued)

*Primary Examiner* — Sanchita Roy
(74) *Attorney, Agent, or Firm* — Shumaker & Sieffert, P.A.

(57) ABSTRACT

Techniques are disclosed for digitizing a framework for clinical development. In one example, a computing device comprising a memory configured to store a study and a processor may be configured to perform the techniques. The processor may receive, from a user, an input specifying a plurality of trial elements for the study, and receive, from the user, an input arranging the plurality of trial elements into a tree data structure. The processor may also determine, based on the tree data structure of the plurality of trial elements, one or more trial arms for the study, each trial arm of the one or more trial arms comprising a single path between at least one trial element of the plurality of trial elements to at least one other trial element of the plurality of trial elements. The processor may further output, for display, the one or more trial arms for the study.

23 Claims, 37 Drawing Sheets

(51) Int. Cl.
　　　*G06F 8/34*　　　(2018.01)
　　　*G06F 16/21*　　(2019.01)
　　　*G06F 16/22*　　(2019.01)
　　　*G06F 16/23*　　(2019.01)
　　　*G06F 16/907*　　(2019.01)
　　　*G06F 16/908*　　(2019.01)
　　　*G16H 10/20*　　(2018.01)
　　　*G16H 10/60*　　(2018.01)

(52) U.S. Cl.
　　　CPC ........ *G06F 16/212* (2019.01); *G06F 16/2246* (2019.01); *G06F 16/2379* (2019.01); *G06F 16/9024* (2019.01); *G06F 16/9027* (2019.01); *G06F 16/907* (2019.01); *G06F 16/908* (2019.01); *G16H 10/60* (2018.01)

(58) Field of Classification Search
　　　CPC .. G06F 16/211; G06F 16/212; G06F 16/2246; G06F 16/2379; G06F 16/9024; G06F 16/9027; G06F 16/907; G06F 16/908; G06Q 10/103
　　　See application file for complete search history.

(56) References Cited

U.S. PATENT DOCUMENTS

| | | | |
|---|---|---|---|
| 2004/0249664 A1* | 12/2004 | Broverman | G16H 10/20 705/2 |
| 2005/0055241 A1 | 3/2005 | Horstmann | |
| 2005/0138635 A1 | 6/2005 | Auerbach et al. | |
| 2005/0256380 A1 | 11/2005 | Nourie et al. | |
| 2007/0174305 A1 | 7/2007 | Arocena | |
| 2008/0104141 A1 | 5/2008 | McMahon | |
| 2009/0313048 A1 | 12/2009 | Kahn et al. | |
| 2010/0118871 A1 | 5/2010 | Liu et al. | |
| 2011/0153358 A1 | 6/2011 | Campo et al. | |
| 2012/0035954 A1 | 2/2012 | Yeskel | |
| 2012/0101838 A1 | 4/2012 | Lingard et al. | |
| 2013/0232104 A1 | 9/2013 | Goyal et al. | |
| 2014/0039921 A1 | 2/2014 | Broverman et al. | |
| 2014/0222444 A1 | 8/2014 | Cerello et al. | |
| 2014/0280363 A1* | 9/2014 | Heng | G06F 16/185 707/802 |
| 2015/0142330 A1* | 5/2015 | Yeang | G16H 50/20 702/19 |
| 2017/0286456 A1 | 10/2017 | Wenzel et al. | |
| 2017/0357778 A1 | 12/2017 | Archer et al. | |
| 2018/0039399 A1 | 2/2018 | Kaltegaertner et al. | |
| 2020/0177710 A1 | 6/2020 | Wyatt et al. | |
| 2021/0241859 A1* | 8/2021 | Bhattacharya | G06F 30/10 |
| 2022/0004540 A1 | 1/2022 | Watson et al. | |
| 2022/0005554 A1 | 1/2022 | Malfait et al. | |
| 2022/0005555 A1 | 1/2022 | Malfait et al. | |
| 2022/0005558 A1 | 1/2022 | Malfait et al. | |
| 2023/0274809 A1 | 8/2023 | Dimitrova | |
| 2023/0360779 A1 | 11/2023 | Gnanasambandam et al. | |

OTHER PUBLICATIONS

"ICH E9 (R1) addendum on estimands and sensitivity analysis in clinical trials to the guidelin on statistical principles for clinical trials," European Medicines Agency, Committee for Medicinal Products for Human Use, EMA/CHMP/ICH/4362221/2017, Feb. 17, 2020, 19 pp.

"Nurocor Clinical Platform—Technical Perspective," Nurocor, Inc., accessed on Apr. 29, 2020, 11 pp.

"Optimize Clinical Development," Nurocor and Intilaris brochure, accessed on Sep. 9, 2020, 2 pp.

Grayling et al., "A web application for the design of multi-arm clinical trials," Arvix.org, Cornell University Library, Jun. 21, 2019.

International Search Report and Written Opinion of International Application No. PCT/US2021/070830, dated Oct. 25, 2021, 15 pp.

Kountouris et al., "Efficient scheduling of conditional behaviors for high-level synthesis," ACM Transactions on Design Automation of Electronic Systems, vol. 7, No. 3, Jul. 1, 2002, pp. 380-412.

Lin et al., "A Standard-Driven Approach for Electric Submission to Pharmaceutical Regulatory Authorities", Journal of Biomedical Informatics, vol. 79, Jan. 31, 2018, pp. 60-70.

Nelson et al., "CDISC 2019 US Interchange," [Presentation], CDISC, San Diego, CA, Oct. 14-18, 2019, 19 pp.

Sjobergh et al., "Visualizing Clinical Trial Data Using Pluggable Components," Information Visualisation, 2012 16th International Conference, Jul. 11, 2012, pp. 291-296.

U.S. Appl. No. 29/652,731, filed Nov. 2, 2021, naming inventors Malfait et al.

International Preliminary Report on Patentability from International Application No. PCT/US2021/070830 dated Jan. 19, 2023, 11 pp.

Response to Communication Pursuant to Rules 161(1) and 162 EPC dated Feb. 14, 2013, from counterpart European Application No. 21749512.6, filed Aug. 11, 2023, 34 pp.

Response to Communication Pursuant to Rules 161(1) and 162 EPC dated Feb. 16, 2023, from counterpart European Application No. 21749511.8, filed Aug. 16, 2023, 30 pp.

Response to Communication Pursuant to Rules 161(1) and 162 EPC dated Feb. 16, 2023, from counterpart European Application No. 21749514.2, filed Aug. 25, 2023, 34 pp.

Jiang et al., "Using Semantic Web technologies for the generation of domain-specific templates to support clinical study metadata standards", Journal of Biomedical Semantics, vol. 7, No. 10, BioMed Central, Mar. 6, 2016, 10 pp., https://doi.org/10.1186/s13326-016-0053-5.

* cited by examiner

| Query | |
|---|---|
| businessObject | BusinessObject |
| definedActivities | [DefinedActivity]] |
| definedActivity | DefinedActivity |
| definedActivityFilterById | DefinedActivityFilter| |
| definedActivityFilterDomains | [String]] |
| definedActivityFiltersByDomains | [DefinedActivityFilterDomain]] |
| endpointTemplate | EndpointTemplate |
| endpointTemplates | [EndpointTemplate| |
| exportFormats | [ExportFrom[]| |
| features | FeatureResponse| |
| getSchedulePDF | ReportRespone| |
| health | HealthResponse| |
| object | Object |
| objectiveTemplate | ObjectiveTemplate |
| objectiveTemplates | [ObjectiveTemplate| |
| objectiveTemplatesByIndication | [ObjectiveTemplate| |
| pingStudyDesign | String| |
| propertyGroup | PropertyGroup |
| propertyGroupByNameVersion | PropertyGroup |
| studies | [Study]] |
| terms | [Term]] |

Trial Arms Dataset

| Row ↑ | STUDYID | DOMAIN | ARMCD | ARM | TAETORD | ETCD | ELEMENT | TABRANCH | TATRANS | EPOCH |
|---|---|---|---|---|---|---|---|---|---|---|
| 1 | gsd-demo-1 | TA | DA | Arm 1 | 1 | scrn | screen | , | , | Screening |
| 2 | gsd-demo-1 | TA | DA | Arm 1 | 2 | rn | run-in | , | , | Run-in |
| 3 | gsd-demo-1 | TA | DA | Arm 1 | 3 | DA | Drug A | , | , | Treatment |
| 4 | gsd-demo-1 | TA | P | Arm 2 | 1 | scrn | screen | , | , | Screening |
| 5 | gsd-demo-1 | TA | P | Arm 2 | 2 | rn | run-in | , | , | Run-in |
| 6 | gsd-demo-1 | TA | P | Arm 2 | 3 | P | Placebo | , | , | Treatment |
| 7 | gsd-demo-1 | TA | P | Arm 3 | 1 | scrn | screen | , | , | Screening |
| 8 | gsd-demo-1 | TA | P | Arm 3 | 2 | rn | run-in | , | , | Run-in |
| 9 | gsd-demo-1 | TA | P | Arm 3 | 3 | P | Placebo | , | , | Treatment |
| 10 | gsd-demo-1 | TA | DB | Arm 4 | 1 | scrn | screen | , | , | Screening |
| 11 | gsd-demo-1 | TA | DB | Arm 4 | 2 | rn | run-in | , | , | Run-in |
| 12 | gsd-demo-1 | TA | DB | Arm 4 | 3 | DB | Drug B | , | , | Treatment |
| 13 | gsd-demo-1 | TA | DB | Arm 5 | 1 | scrn | screen | , | , | Screening |
| 14 | gsd-demo-1 | TA | DB | Arm 5 | 2 | rn | run-in | , | , | Run-in |
| 15 | gsd-demo-1 | TA | DB | Arm 5 | 3 | DB | Drug B | , | , | Treatment |

GRAPHICAL STUDY DESIGN FOR CLINICAL RESEARCH STUDY SYSTEMS

This application claims the benefit of U.S. Provisional Application No. 63/048,375, entitled "DIGITIZED FRAMEWORK FOR CLINICAL DEVELOPMENT," and filed Jul. 6, 2020, and U.S. Provisional Application No. 63/198,657, entitled "DIGITIZED FRAMEWORK FOR CLINICAL DEVELOPMENT," and filed Nov. 2, 2020, the contents of both of which are hereby incorporated by reference as if set forth fully herein.

TECHNICAL FIELD

This disclosure generally relates to systems for managing clinical studies.

BACKGROUND

Data standards are often developed and used as a uniform communicative structure for the transfer of data from one entity to another entity. These data structures may be used by a receiving entity so that data can be processed in a known format for efficiency and validation during processing. Regulatory agencies are becoming advocates of data standards for submission, analysis, and approval of consumable products. However, implementation of data standards is often burdensome and expensive for industry. Moreover, as a data standard is changed or updated, the implementation of the standard may need to be changed or updated, which may require significant programming efforts and further expense.

SUMMARY

In general, the disclosure describes techniques for digitizing a framework for clinical development. In some examples, a system as described herein defines a data model that specifies a data standard representative of requirements for regulatory-compliant exchange of data between entities and stores metadata for the data model in a metadata repository (MDR). As described herein, the data model includes one or more client business objects representing aspects of a well-structured pharmaceutical clinical research study. As described herein, a clinical research study (also referred to herein as a "study") is, for example, a clinical research project whose objectives are to test or confirm hypotheses concerning the utility, impact, pharmacological, physiological, and/or psychological effects of a particular treatment, procedure, drug, device, biologic, food product, cosmetic, care plan, or subject characteristic. Each study as a whole specifies one or more study events, (referred to herein as "study events" or "events") and each study event of the one or more study events specifying one or more study activities (also referred to herein as "study activities" or "activities") to be planned for the study event.

In addition to the events and activities mentioned above, the data model further includes additional study data elements (referred to herein as "study elements", "protocol elements" or "elements") each of which is represented as a dynamically configured property within the MDR. These properties are collected into one or more dynamically configured property groups, also specified within the MDR, with each property group representing a section of the study (referred to herein as "study section" or "section") whose elements are cohesively related. Section examples include Planned Intervention, Inclusion Criteria and Study Model Elements among others. These properties may be aggregated into standardized data sets for purposes of regulatory submission, or used to inform other aspects of study design (e.g., the authoring of a study protocol document that specifies the study in narrative form, submission of which is also a regulatory requirement).

The system uses the metadata stored in the MDR to generate a study template for planning a clinical research study. A user interface obtains input from a user to parameterize the study template and store the parameterized template in a database. The system further generates, based on the template, a sequence of one or more study events specifying one or more study activities to be executed for the study event. In some examples, the system may further generate, based on the template, one or more study sections each of which is composed of one or more study elements. In some examples, the system may further generate, based on the template, at least one study objective and at least one study estimand or endpoint (referred to herein as "endpoint") that may be used to facilitate generation of key activities and events within a schedule of study activities.

In some instances, objectives may specify precise endpoint descriptions, defined by ways to estimate (which may be referred to as an estimator) and a numerical result (which may be referred to as an estimate), where, for example, in a diabetes study an endpoint may be described by an estimator HbA1c (glycated hemoglobin) as a measure for blood glucose levels, and an estimate that compares the change from study baseline of HbA1c at a prespecified study timepoint. An estimand may refer to a precise description of the treatment effect reflecting a clinical question posed by a trial objective and may have different components depending on a phase and purpose of a given trial. Estimands may be mandatory for confirmatory studies.

An estimand description may not be required for exploratory objectives or for core phase 1 studies. Estimand components include a study population, a statistical variable to be measured (which again may be referred to as an endpoint), details of how to account for intercurrent events (e.g. study discontinuation), and a population-level summary of a variable.

In some examples, the system may generate reporting information and documentation, and/or determine a cost estimate for each study activity of the study. The techniques disclosed herein further enable performing a "lazy" copy of elements stored in the database, and further enable updating or deleting elements of the database where a lazy copy has been performed.

Moreover, within the context of a clinical trial and clinical operations processes, activities can be accelerated through what is described herein as the "lean protocol process," which is based on protocol development gates from Clinical Development Plan (CDP) through to final protocol. This "gated" process begins with the CDP/Protocol workflow as the first gate when critical data is first available and enables parallel development of the protocol, SAP and study build to begin. The early availability of critical study data elements further triggers early and parallel development of functional plans and process activities. Using feasibility as an example, study population, planned procedures and reference drugs may be identified at gate 1 and trigger development of the feasibility and strategy plan. The protocol is further refined through subsequent gates, enabling early execution of protocol feasibility to begin after gate 2 and site feasibility activities at gate 3 or protocol level 2. The same methodology applies to other functional plan development such as data management (DM) and monitoring. Most importantly, this lean process provides the shared alignment and transparency to generate and address recommendations for changes to the study design before final protocol.

The Lean Protocol process digitizes and standardizes data that may be important to the reliability of the study findings, specifically data that supports primary and key secondary estimands/endpoints. By prioritizing the critical domains and activities based on what is unique to the study such as new/unique tools/procedures or safety considerations as a result of comparator drugs or the indication, the techniques herein may drive informed decisions and risk assessment. Leveraging the early availability of the digitized study-critical elements also facilitates study build processes such as Electronic Data Capture (EDC) configuration and Randomization and Trial Supply Management (RTSM) specification.

Critical data for reporting and analysis are also identified early on in the planning phase, driving a potential early start on development of dashboards and reporting specifications. Therefore, the lean protocol process driven by data standards and the digital protocol may accelerate the lifecycle through to submission data sets that are consistent with the protocol. This "intelligent automation" through the lean protocol process may drive quality, consistency, and behaviors that focus on critical data versus the completeness and accuracy of every data point at the expense of critical aspects. The end result provided by the lean protocol process may enable a significant reduction of the clinical life cycle and submission timeline driven by a systematic quality by design process.

In addition, various aspects of the techniques may enable a graphical user interface (GUI) clinical study protocol designer (also referred to herein as "Graphical Study Designer") that allows a study design practitioner (or, in other words, a user) to graphically model the conceptual structure of a Study Protocol in an intuitive manner and as a result of that modeling, automatically generate the Arms necessary to execute that Study Protocol. The extended functionality provided by the graphical study designer improves user efficiency and accuracy in the early stages of Study Design. Each Arm represents a path through which a Study Subject can proceed within the context of the Study.

The Graphical Study Designer application and supporting microservice may eliminate the potential for an inaccurate representation of these Arms and the resulting delays in Study Protocol finalization that would ensue from such an error. In this manner, the Graphical Study Designer provides a more capable alternative means of modeling Study Protocol Arms than a tabular capability otherwise disclosed as part of the Study Protocol Elements application provided by the system.

In this way, the techniques of the disclosure may provide specific improvements to the computer-related field of database management that have practical applications. For example, the techniques disclosed herein enable the digitization of clinical research studies, clinical research study management, and clinical research study reporting requirements so as to obviate the performance of clinical research study management by hand. Therefore, the techniques of the disclosure improve efficiency and data quality, reduce cycle times, reduce the cumbersome administrative overhead of clinical research study management by hand, as well as reduce the potential for error or omission in critical record-keeping. Furthermore, the techniques of the disclosure allow for the use of a lazy copy in a database as well as enabling the updating or deleting of elements of the database where a lazy copy has been performed. In this manner, the techniques of the disclosure may allow for the use of lazy copy to increase performance of copying elements, even where the elements are within a complex database such as a graph database, without substantially impacting the user experience or computing performance.

In one example, this disclosure describes a method comprising: defining, by processing circuitry, a data model comprising metadata that specifies a data standards-based representation of requirements for regulatory-compliant exchange of data between entities, wherein the data model includes one or more client business objects, each client business object specifying one or more study events or supporting study elements, and each study event of the one or more study events specifying one or more study activities to be executed for the study event, and wherein the data model includes one or more properties for each of the client business objects that organize the client business objects and supporting study elements into one or more property groups representing study sections, and expressing, by the processing circuitry, the data model to define one or more templates for a clinical research study comprising at least a sequence of the one or more study events, and in some examples one or more study element properties collected into at least one property group representing a study section, and/or at least one study objective and at least one study endpoint.

In another example, this disclosure describes a method comprising: retrieving, by processing circuitry and from a regulatory database, a template based on a governance process; receiving, by the processing circuitry and via a user interface, input from a user; parameterizing, by the processing circuitry, the template based on the governance process with the user input to create a parameterized template; and storing, by the processing circuitry, the parameterized template in a database.

In another example, this disclosure describes a method comprising: retrieving, by processing circuitry and from a regulatory database, a template based on a governance process; receiving, by the processing circuitry and via a user interface, input from a user; parameterizing, by the processing circuitry, the template based on the governance process with the user input to create a parameterized template; and generating, by the processing circuitry and based on the parameterized template, a clinical research study comprising at least a sequence of one or more study events specifying one or more study activities to be executed for the study event, and in some examples one or more study element properties collected into at least one property group representing a study section, and/or at least one study objective and one study endpoint; and presenting, by the processing circuitry, via the user interface, and to the user, the clinical research study.

In another example, this disclosure describes a method for copying a first node of a tree data structure, the method comprising: duplicating, by processing circuitry, a first node to create a duplicate node, wherein the first node comprises an inbound edge to a parent node of the first node and at least one outbound edge to at least one child node of the first node; creating, by the processing circuitry, an inbound edge of the duplicate node to the parent node of the first node and an outbound edge to the at least one child node of the first node; receiving, by the processing circuitry, an update to the at least one child node of the first node; in response to determining that the at least one child node has multiple parent nodes: duplicating, by the processing circuitry, the at least one child node to create a duplicate child node; creating, by the processing circuitry, an outbound edge of the duplicate node to the duplicate child node; deleting, by the processing circuitry, the outbound edge of the duplicate node to the at least one child node; and performing, by the processing circuitry, the update to the at least one child node.

In another example, this disclosure describes a method for deleting a first node of a tree data structure, the method comprising: determining, by processing circuitry, that the first node has multiple parent nodes, wherein the first node comprises multiple inbound edges to the multiple parent nodes of the first node and at least one outbound edge to at least one child node of the first node; in response to determining that the first node has multiple parent nodes: determining, by the processing circuitry, a closest superior ancestor node of the first node that has only a single parent node: duplicating, by the processing circuitry, the superior ancestor node of the first node to create a duplicate superior ancestor node; duplicating, by the processing circuitry, a branch descending from the superior ancestor node of the first node to create a duplicate branch descending from the duplicate superior ancestor node, wherein the duplicate branch descending from the duplicate superior ancestor node duplicates nodes and edges of the branch descending from the superior ancestor node of the first node; and deleting, by the processing circuitry, the first node and any inferior descendent nodes of the first node.

In another example, this disclosure describes a method for deleting a first node of a tree data structure, the method comprising: determining, by processing circuitry, that the first node comprises at least one outbound edge to at least one child node of the first node, wherein the first node comprises an inbound edge to a parent node of the first node; determining, by the processing circuitry and based on inbound edges of the at least one child node to the first node and to a second node, that the at least one child node has multiple parent nodes; and deleting, by the processing circuitry, the first node, an outbound edge of the parent node to the first node, and the inbound edges of the at least one child node to the first node.

In another example, this disclosure describes a method comprising: receiving, by processing circuitry and from a user, an input specifying a plurality of trial elements for a study; receiving, by the processing circuitry and from the user, an input arranging the plurality of trial elements into a tree data structure; determining, by the processing circuitry based on the tree data structure of the plurality of trial elements, one or more trial arms for the study, each trial arm of the one or more trial arms comprising a single path between at least one trial element of the plurality of trial elements to at least one other trial element of the plurality of trial elements; and outputting, by the processing circuitry and for display, the one or more trial arms for the study.

In another example, this disclosure describes a device comprising processing circuitry configured to: receive, from a user, an input specifying a plurality of trial elements for a study; receive, from the user, an input arranging the plurality of trial elements into a tree data structure; determine, based on the tree data structure of the plurality of trial elements, one or more trial arms for the study, each trial arm of the one or more trial arms comprising a single path between at least one trial element of the plurality of trial elements to at least one other trial element of the plurality of trial elements; and output, for display, the one or more trial arms for the study.

In another example, this disclosure describes a non-transitory, computer-readable medium comprising instructions that, when executed, are configured to cause processing circuitry to: receive, from a user, an input specifying a plurality of trial elements for a study; receive, from the user, an input arranging the plurality of trial elements into a tree data structure; determine, based on the tree data structure of the plurality of trial elements, one or more trial arms for the study, each trial arm of the one or more trial arms comprising a single path between at least one trial element of the plurality of trial elements to at least one other trial element of the plurality of trial elements; and output, for display, the one or more trial arms for the study.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIG. 5 is a block diagram illustrating an example query data structure for a clinical research study template in accordance with the techniques of the disclosure.

FIGS. 20-30 are illustrations of a graphical user interface (GUI) clinical study protocol designer in accordance with the techniques of the disclosure.

FIG. 32 is a diagram illustrating a graphical user interface that includes statuses of a plurality of gates for a single study.

Like reference characters refer to like elements throughout the figures and description.

DETAILED DESCRIPTION

Figure 1:
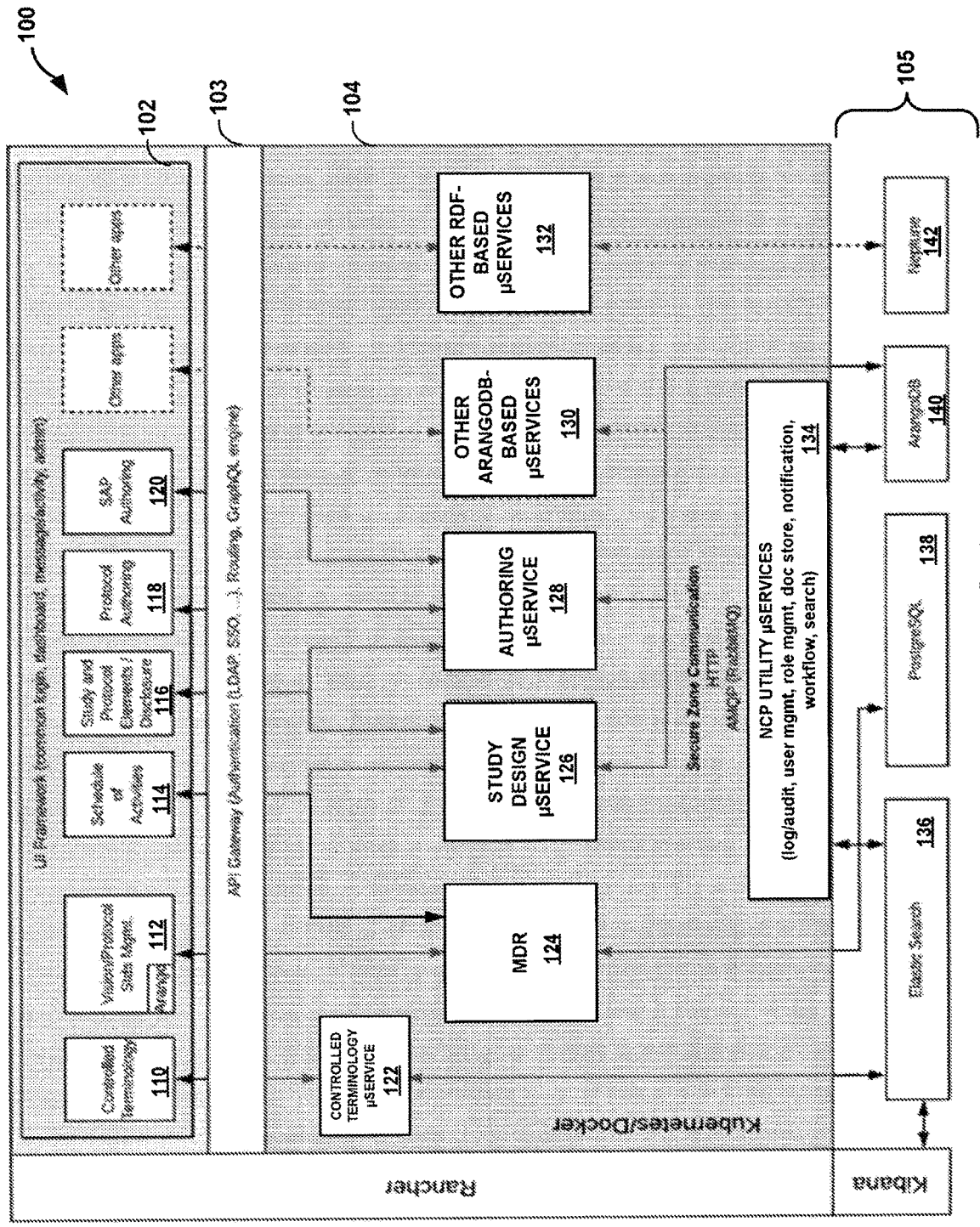
FIG. 1 is a block diagram illustrating an example system for generating a digitized framework for clinical development in accordance with the techniques of the disclosure.

FIG. 1 is a block diagram illustrating example system 100 for generating a digitized framework for clinical development in accordance with the techniques of the disclosure. System 100 includes UI framework 102, microservice platform 104, and database 105. System 100 further includes API gateway 103 which interfaces between UI framework 102 and microservice platform 104.

System 100 provides a clinical lifecycle management application suite and provides a technology platform that supports multiple means of integration and collaboration. System 100 is architected with three core principles in mind: modularity and flexibility, scalability resiliency and security, and openness and pluggability.

System 100 uses a microservice-based architecture, which provides a flexible means of building out incremental functionality, with each microservice deployed within the platform controlling its own data and collaborating with other microservices and UI based applications via one or more APIs, with API gateway 103 serving as both a security layer and an internal routing mechanism for such APIs. Microservices also enable multiple programming languages to be used within the same deployment platform. In some examples, system 100 uses a mix of Java and node.js languages to develop fit-for-purpose components.

UI framework 102 provides a framework for various applications to provide information to a user. Typically, an application of UI framework 102 operates in conjunction with a corresponding microservice of microservice platform 104. In the example of FIG. 1, UI framework 102 includes controlled terminology application 110, which operates with controlled terminology microservice 122 of microservice platform 104 to support the ingestion of quarterly updates of controlled terminology from CDISC and NCI. UI framework 102 further includes protocol standards management application (also known as Vision) 112, which operates with MDR 124 to provide clinical standards management. Schedule of study activities application 114, Study and Protocol Elements/disclosure application 116, protocol authoring application 118, and statistical analysis plan (SAP) authoring application 120 operate in conjunction with study design microservice 126 and authoring microservice 128 to facilitate the digitization and automation of clinical research studies as discussed in more detail below.

Each microservice 122, 124, 126, 128, 130, and 132 communicates within the platform and to UI framework 102 through APIs. System 100 is an API-first platform, and uses a combination of GraphQL based APIs as well as REST-based APIs to support intercommunication both within the server side of the platform as well as communication to the outside world through UI-based applications and via direct API calls.

With respect to UI-based applications 110, 112, 114, 116, 118, 120, system 100 implements a common UI framework 102 that all applications consume. UI framework 102 provides a seamless cross-application navigation interface such that a user of system 100 is not aware that the user is using multiple applications. Instead, the user simply navigates from capability to capability as he or she goes about his or her daily work. Lastly, system 100 supports multiple data persistence platforms and enables the easy addition of support for additional data platforms in the future.

In some examples, from a scalability, resiliency and security standpoint, system 100 uses a combination of Docker and Kubernetes as a deployment backbone. Docker enables the packaging up of stateless applications or components, such as microservices and UI-based applications, in a reusable fashion. Kubernetes then combines its capabilities with Docker to manage Docker instances within a runtime environment, automatically scaling those capabilities, ensuring that the instances stay up and running as well as managing restarts when needed, and otherwise providing effective administrative capability over the run-time of the platform.

An administrator may manage system 100 through Rancher, which is a popular administrative user interface plugged into the Kubernetes environment. System 100 also provides access to elastic search 136 from a log and audit standpoint through a Kibana UI front end, which is part of the ELK (Elasticsearch, LogStash, Kibana) suite. Although described with respect to a particular front end user interface (UI), e.g., Kibana UI, for accessing ELK databases, and a particular database, system 100 may utilize different front end UIs and databases.

System 100 provides a secure and flexible perimeter around back-end microservices that are managing data via a purpose-built API Gateway 103. System 100 uses industry-hardened components within this implementation to provide core endpoint security, to give the flexibility to plug in multiple authentication approaches such as (Lightweight Directory Access Protocol (LDAP) and various types of Single Sign-On (SSO) and to support federation of GraphQL APIs. API Gateway 103 also provides other baseline capabilities, such as health check support, for the various components in the platform and a means for components to register as the components come online.

System 100 is architected to be open and pluggable via the use of APIs that facilitate loosely coupled integration. These APIs support both technical integrations around the utility capabilities of the platform as well as functional integrations that support the clinical lifecycle. Above and beyond this loosely coupled API support, system 100 supports deep integration through a well-defined set of internal microservice APIs 122, 124, 126, 130, 132 and a reusable UI Framework 102. These interfaces enable partners and customers to develop natively-deployed microservices and UI apps that sit seamlessly alongside capabilities that system 100 delivers.

In some examples, the runtime of system 100 is based on Docker. Docker is a container virtualization environment that enables components based on Java, node.js and other languages to efficiently share a set of pooled runtime instances. These images are then configured to be deployed within cloud platforms or into properly-configured on-premises (so-called "on-prem") environments in a reusable and scalable manner. Kubernetes supports platform scalability and resiliency by providing a management backbone for these Docker instances. When one configures Kubernetes, one establishes various clusters of runtime containers and establishes affinity for various components that one is deploying into those containers. Kubernetes then manages those capabilities to ensure that the platform stays up and performs well. Kubernetes also provides a communication backbone in the form of a private IP network.

The architecture of system 100 builds upon common data stores by provisioning data stores of various types. In some examples, system 100 leverages relational data stores in the form of PostgreSQL 138, document type NoSQL data stores in the form of Elasticsearch 126, and combination document/graph type data stores in the form of ArangoDB 140. System 100 may also integrate with other data stores, such as RDF triple stores. Rancher provides a UI for managing Kubernetes instances, and Kibana provides effective log and audit retrieval and analysis capabilities on top of Elasticsearch 126.

System 100 includes a security layer between the server side of the platform and the outside world, e.g., the Internet or other public networks. System 100 creates a secure "green zone" within Kubernetes taking advantage of the private IP network that Kubernetes provides. System 100 also supports internal message queue-based communication through Advanced Message Queueing Protocol (AMQP) provided by a RabbitMQ instance. All of this is secured behind a purpose-built application programming interface (API) Gateway 103. API Gateway 103 provides a secure perimeter for API exposure to the outside world, both to applications of system 100 as well as for direct integration from other partner platforms or customer direct usage. API Gateway 103 also enables pluggable authentication through various authentication strategies, including, for example, lightweight director access protocol (LDAP), header based single sign-on (SSO), security assertion markup language (SAML) based SSO, or open identification (OpenID). Other authentication strategies may also be enabled via this pluggable authentication framework. API Gateway 103 integrates a GraphQL engine that allows microservices 122, 124, 126, 128, 130, 132 to provision their portion of the data graph into a federated GraphQL API. This GraphQL API aggregates data content across all the various microservices supporting system capabilities. This provides increased client-side ease of use and efficient access to content provided by system 100.

System 100 uses both a common UI framework 102 and a back-end set of utility microservices 134. UI framework 102 provides all applications with common login, common user session management and seamless cross-application navigation, with applications registering into the framework such that they are able to communicate and navigate with each other. UI framework 102 also provides various shared end user and administrative UI elements including a library of common widgets and other components that are available for application development. In the back-end, system 100 provides a suite of utility microservices that in essence provide the shared technical capabilities needed in order to build out an enterprise-class application platform suite. Capabilities such as dynamic properties, comments, change requests, logging, audit, user management, role and permissions management (i.e., access control), document store, reporting, notifications through multiple channels, integrated workflow and integrated cross-application search are part of utility microservice suite 134.

System 100 enables data standards management by an underlying metadata repository (MDR) 124 that is embedded within system 100. MDR 124 is an ISO 11179-based MDR that support the provisioning of configurable content. In some examples, MDR 124 is a regulatory database based on a governance process that defines a protocol model for storing metadata. This metadata is managed to ensure that version control is maintained as the platform and its capabilities mature over time. Robust workflow and governance capabilities of the system 100 apply both as new clinical data standards (CDISC and others) are specified and provisioned and as new program, protocol and study standards are defined and refined.

In some examples, MDR 124 is prepopulated with clinical data acquisition standards harmonization (CDASH) to study data tabulation model (SDTM) transformation rules. As organizations continue to build out more efficient clinical lifecycle execution, MDR 124 may incorporate additional rule-based transformations (including internal standards transformations and transformations from SDTM to analysis data model—ADaM). MDR 124 may express rules in narrative or executable form (for example statistical analysis system—SAS—program fragments). Additional models and transformation rules between models may be incorporated as required to support clinical trial modeling, definition and execution.

MDR 124 is an ISO 11179-based MDR that support the provisioning of configurable content. This metadata is managed to ensure that version control is maintained as the platform and its capabilities mature over time. Robust change request, workflow and governance capabilities of the system 100 apply both as new clinical data standards (CDISC and others) are specified and populated, and as new program, protocol and study standards are defined and refined.

MDR 124 is exposed to data standards curators and other standards management personnel through Protocol Standards Management application 112 (also known as Vision). Vision provides a very flexible yet end user centric view over MDR content. MDR 124, by its very nature, includes technical components and Vision allows the presentation of MDR content in a context that is meaningful to managers of that content. Controlled terminology microservice 122 and application 110 suite augment MDR 124 by supporting the ingestion of quarterly updates of controlled terminology from CDISC and NCI. Thus, MDR 124 provides a flexible application that supports effective identification of the intersection between new terminology and existing internal terminology defined by clinical organizations and helps customer organizations manage the impact of adopting newly defined terminology on a case-by-case basis. API Gateway 103 in turn exposes data standards APIs that allow system 100 to support downstream data platform provisioning with other customer or vendor platforms.

In addition to supporting direct content access externally via GraphQL API calls, the platform also provides reporting microservice 134 which exposes platform content via configured REST APIs. Each configured API is exposed via API Gateway 103 and is associated with an internal GraphQL query that retrieves content of interest for the report. Query results are then provided to a configurable formatting engine that is part of microservice 134. The formatting engine collects, organizes, and transforms the contents of query results into the desired output in the form of java script object notation (JSON), extensible markup language (XML), Microsoft Excel spreadsheet (XLSX), comma separated values (CSV) and/or portable document format (PDF)

as required by the expected user of the configured API. In one example, reporting microservice 134 maps an inbound REST API request to a specific service configuration that defines how to fetch the data needed for the response, how to traverse that data, and how to prepare the response. The incoming request mapping is routed based on the parameterized resource path of the incoming resource request.

Once mapped, the service configuration informs which GraphQL query to run against the system's federated GraphQL interface. This query may be tuned to specify the exact data attributes needed to satisfy the request. The GraphQL response is a JSON object that is further processed by reporting microservice 134. The JSON object is traversed based on the service configuration and is defined in terms of data views, each of which consists of data selectors and (further recursive) data views. During traversal, the recursion algorithm sends events to a formatter when a view starts, a data selector delivers data, or when a view ends. Formatters are agnostic to the actual request, data source or traversal. They prepare a data export based on the events such formatters receive. Each formatter is specialized for a specific export format based on the media type of the original request. Reporting microservice 134 may support response formats for Excel, CSV, JSON, XML, and PDF media types. In another example, the reporting microservice configuration supports the application of XSLT transformations for XML based media types.

Study Design microservice 126 sits at the core of the clinical lifecycle management suite provided by system 100. Study Design microservice 126 provides a fully digital clinical research study representation ranging from study initialization parameters such as Therapeutic Area and Indication, study-specific objectives and endpoints, all the way through to a full fidelity schedule of study activities with study events and study activity items that are to be executed for those study events. Both industry-wide and corporate clinical standards may be automatically sourced from MDR 124 in support of Study Design microservice 126.

Study and Protocol Elements application 116 manages the wide range of elements organized into pages and sections and that are necessary to populate and define a fully specified study. A key aspect of this application is the Objective and Endpoint editor. This editor exposes predefined templates managed within the MDR 124, providing a study designer with an intuitive and easy to use UI when defining primary, secondary, or exploratory Objectives and Endpoints for the study under development. These Objectives and Endpoints establish a basis for the scientific hypotheses to be experimentally assessed by the Study. Study and Protocol elements populated via this application are persisted in study design microservice 126, where the elements become available for downstream systems use including automated disclosure capabilities to relevant authorities.

Schedule of study activities application 114 provides a fully digitized clinical research study schedule development environment that leverages objectives and endpoints that have been previously specified to provide automated suggestions for schedule study events as well as study activities to be executed during those study events. Schedule of study activities application 114 directly consumes industry and corporate data standards automatically from MDR 124 such that once the user has completed schedule definition, a full fidelity schedule is then stored in study design microservice 126, synchronized back to MDR 124 for impact analysis purposes and ultimately enabled for export (via file extract, API invocation or other means) to downstream customer or vendor platforms. In other examples, the full fidelity schedule may be stored in one or more special purpose microservices for impact analysis and export purposes.

System 100 provides an additional protocol standards management capability in the area of data standards via MDR 124. A clinical data standards management protocol standards management application facilitates defining reusable objective and endpoint templates along with other data elements in support of clinical research study lifecycle applications.

Authoring microservice 128 and application suite 120 provide protocol authoring capabilities. In one example, this suite supports a fully digitized implementation of a protocol model of a clinical research study along with other templatized content. Authoring microservice 128 and application suite are natively integrated with study design microservice 126 and MDR 124. Authoring microservice 128 is fully templatized so that one may apply additional templates to support customer-specific protocol formats, and support alternative documents such as statistical analysis plans.

Microservice developers may pick from a wide range of programming languages and data persistence platforms. Specifically, system 100 may incorporate both portfolio and program level applications such as Portfolio Management, Indication Analysis, Target Product Profile (TPP), Clinical Development Plan (CDP) and Protocol Synopsis as well as study execution centric applications and support of topics such as feasibility and recruitment, risk management and supply management. These additional applications are examples only and not intended to limit the scope of system 100.

System 100 uses database 105 to store, manage, and retrieve content for clinical development. Database 105 may take various forms, such as a relational database, a document-based database, or a graph-based database. In the example of FIG. 1, database 105 is implemented with Elasticsearch 136, PostgreSQL 138, ArangoDB 140 and/or Neptune (an example of an RDF Triple Store database) 142. In some examples, database 105 implements GraphQL queries and mutations to manage data. For example, study design microservice 126 implements GraphQL APIs that invoke database 105 as an efficient and flexible way to retrieve clinical development content.

Microservices 122, 124, 126, 128, 130, 132, and 134 are "GraphQL first" in nature. Microservices 122, 124, 126, 128, 130, 132, and 134 expose core Create/Read/Update/Delete (CRUD) actions on their business objects via GraphQL queries and mutations. GraphQL, originally developed by Facebook, Inc. as part of its microservice-based platform architecture, provides two possible features that make GraphOL well-suited for such development: federation and field (attribute) selectivity.

GraphQL supports the concept of API federation, where each microservice contributes its business object declarations to an all-encompassing graph spanning the entire set of business objects deployed into the platform. This federated view is exposed by a single GraphQL API endpoint. As each new microservice 122, 124, 126, 128, 130, 132, and 134 is deployed into the platform, the microservice augments this object graph with the new objects for which it has responsibility. A GraphQL API consumer can in turn initiate a single API query that spans as much of the graph as is needed, with server-side infrastructure efficiently merging the content to support the API request.

Field selectivity in GraphQL is a natural complement to business object federation, as GraphQL allows API consumers to precisely identify which object fields (attributes) are to be returned in query results. This eliminates the potential concern of very large datasets being returned to the client in response to a broad query invocation, while at the same time eliminating the need to implement multiple purpose-specific APIs supporting various combinations of object content to suit the needs of the client. Because GraphQL supports field selectivity, it is easy to modify a full query to database 105 by removing various elements to produce a result that aligns with desired view of the template graph aligned for ease of use to the customer. The result may in turn be transformed from JSON into other representations (e.g., HTML) via reporting microservice 134, UI framework 102, or other means.

System 100 may operate to generate dynamically configured applications composed of pages and sections within pages. Contextual properties such as ordinality, read-only, multivalued and required are used by the UI to present the property correctly within the page section in question. Different property subtypes require specialized context properties; for instance, ordered literal types such as integer, decimal, date and timestamp include optional properties such as lower and upper bounds and Boolean flags that indicate inclusive or exclusive bounds settings. Dynamically retrieved types such as user specify attributes such as permission name (derived from system configuration used to specify access control microservice 134 behavior) and associated resource type, and include optional properties such as whether the current user is to be included in the dynamically retrieved results for the property. Enumerated properties may be specified by value lists within MDR 124, or those value lists may be dynamically retrieved from sources external to MDR 124 (e.g., a list of platform users with a specified role may be retrieved from the system's User microservice in concert with the Access Control microservice, a list of valid Protocol Numbers may be retrieved from an external Clinical Trial Management System (CTMS)). Compound property types (which compose two or more elemental property types) may also be specified within the system. One example of a compound property type is a representation of a Study Event composed of a period type (enumerated value list composed of values such as Day, Week, Month) and integer. The Study Event property type may support automatic generation of Study Events via Endpoint Template parameterization.

Conditional property specifications, where default contextual properties are modified given a specific set of conditions, are also supported. For example, a property A may become editable only when a property B contains a specific value, or when property B is populated with any value. Conditions may span multiple specified values for a designated property (e.g., property C must be set to one of values x, y or z for the condition to be in effect) and may span multiple designated properties (e.g., the conditional rules for properties D, E and F must all be met for the condition to be in effect).

In general, system 100, operating in accordance with the techniques of the disclosure, enables the digitization of a framework for clinical development. For example, study design microservice 126 uses metadata stored in MDR 124 to generate a study template for performing a clinical research study. UI framework 102 obtains input from a user to parameterize the study template and store the parameterized template in database 105. User input includes an Effective Date parameter which is defaulted to the current date and may be modified by the user. The Effective Date value is used to automatically retrieve the correct version of study and protocol standards from which the study template will be generated.

As such, different versions of the study template may be associated with a corresponding Effective Date parameter and thereby facilitate retrieval of a correct version of the study template representative of the governance process identified by the Effective Date parameter. The correct version is selected by identifying the version with a specified date most recently prior to the Effective date specified for the study. For example, if three versions of the study template exist, with version 1 specified date set to Jan. 31, 2018; version 2 set to Oct. 15, 2019; and version 3 set to Dec. 31, 2020, then Study A with an effective date of Jul. 15, 2019 would be assigned version 1, Study B with an effective date of Jan. 15, 2020 would be assigned version 2, and Study C with an effective date of Apr. 30, 2021 would be assigned version 3. The ability to specify an Effective Date may be useful for long-running Clinical Development Programs (e.g., for an Oncology Therapeutic Domain) where Studies within a Program span years and for which a consistent set of standards must be applied.

Study design microservice 126 generates, based on the template and potentially combined with user input, a sequence of one or more study events specifying one or more study activities to be executed for the study event and study elements associated with the clinical research study. As described herein, a "study event" refers to a checkpoint or milestone during a clinical research study at which specific study activities are performed. The study event specifies one or more study activities to be executed for the corresponding study event. Each study activity may be, e.g., a clinical assessment or procedure to be performed on a subject, a data element to be measured from the subject, an assemblage of already existing data about the subject, or collection of non-treatment related data (e.g., healthcare utilization) from the subject. The detailed specification of a study activity is based on data collection standards (e.g., CDASH) as governed within MDR 124, thus linking these collection standards (and by extension tabulation, analysis and other data standards via transformation rules also governed in MDR 124) to the study template and protocol standards also specified within that template. For example, a study event for a study objective may occur on a periodic basis (e.g., daily, weekly, or monthly) and specify that a study activity to be performed, for example, that a subject's blood pressure and heart rate be monitored. In accordance with the techniques of the disclosure, a clinical research study may be quantized into a sequence of such study events and study activities, and thereby objectively defined and measured.

Study elements are data elements that a regulatory authority may require the collection of during the clinical research study. Further, the regulatory authority may require the submission of such study elements to the regulatory authority as part of reporting requirements of the clinical research study. System 100 enables the collection of study element data via configuration of properties and property groups specified as part of the study template and managed within MDR 124. System 100 manages these configured elements as configured sections within study design microservice 126 and directly persisted via dynamic property microservice, one of the utility microservices 134. These configured sections also support the Lean Protocol process as disclosed in subsequent paragraphs. Dynamic property microservice 134 is primed to accept study elements by study design microservice 126 through advanced message queuing protocol (AMQP) messages informing dynamic property microservice 134 of the study element sections specified in the template used for the study. Use of asynchronous messaging in this manner may preserve loose coupling between microservices.

In some examples, the specific types of study elements are mandated by the regulatory authority (e.g., as CDISC submission data sets). Examples of study elements include data related to pharmaceutical administration, sponsor information, study planning, or study extensions. Study elements related to pharmaceutical administration may include a dose formulation of the pharmaceutical studied in the clinical research study, a route of administration, a dose per administration, a dose regimen, dose units, or dosing frequency. Study elements related to sponsor information may include a responsible party, a sponsor status, a sponsor name, sponsor contact information, a sponsor legal address, a sponsor telephone number, or a sponsor email address. Study elements related to study planning may include a planned number of subjects, a planned treatment duration, a stable disease minimum duration, a confirmed response minimum duration, a planned trial duration, or study stop rules. Study elements related to study extension may include an extension trial indicator, a substudy planned indicator, or substudy details.

In some examples, study design microservice 126 may further generate, based on the template, at least one study objective and at least one study endpoint that may be used to facilitate generation of key activities and events within a schedule of study activities. A study objective specifies a hypothesis for the clinical research study. A study endpoint specifies a means by which the hypothesis is evaluated (e.g., a lab test, physiological measurement, or other data point). Each study event may be linked to a study objective and an associated study endpoint of the study objective. For example, a study endpoint is defined within the scope of a study objective, and the study endpoint is the means by which one establishes connectivity to a corresponding study activity for a study event. In other words, the study endpoint allows for the definition of one or more relevant study activities to be executed in associated study events. In some examples the study endpoint is connected to one or more study activities via introduction of a Biomedical Concept resource type within MDR 124.

By defining a hypothesis through a study objective and a means for testing the hypothesis with a corresponding study endpoint, system 100 may generate a sequence of study events and study activities to be performed for each study event such that system 100 may objectively define the clinical research study as well as a method for implementing and carrying out the clinical research study. As described in more detail herein, various applications executing within microservice platform 104 may generate a schedule of study activities and study events to implement the study, generate reporting information and documentation, and/or determine a cost estimate for each study activity of the study.

As a further example, study design microservice 126 enables the specification of repeated activities during a single study event. Such a specification is called a timepoint schedule. Consider the scenario where a study event X includes drug administration (Exposure) followed by repeated measurements of Vital Signs, e.g., 10 min, 20 min, and 30 min after drug exposure. In this scenario, the Exposure study activity is marked once on the main schedule for study event X and a timepoint schedule with three timepoints is created for study event X. The Vital Signs study activity is then scheduled for observation at each of the timepoints.

As further described below, to support the digitized framework for clinical development described herein, MDR 124 extends the data model set forth in ISO 11179. For example, MDR 124 implements a data model that specifies a data standard representative of requirements for regulatory-compliant exchange of data between entities and stores metadata for the data model. As described herein, the data model includes one or more client business objects representing aspects of a well-structured pharmaceutical clinical research study. As described herein, a clinical research study is, for example, a research project whose objectives are to test or confirm hypotheses concerning the utility, impact, pharmacological, physiological, and/or psychological effects of a particular treatment, procedure, drug, device, biologic, food product, cosmetic, care plan, or subject characteristic.

MDR 124 extends each client business object to represent a clinical research study or associated study element, whereas each clinical research study in turn specifies one or more study events. Each event specifies one or more study activities to be executed for the corresponding study event. MDR 124 further extends the data model of ISO 11179 to include one or more properties for each of the client business objects that organize the client business objects into one or more property groups. These properties and property groups are used to represent both cohesive collections of study elements (i.e., sections) and configurable elements of objective and endpoint templates.

The extended data model implemented by MDR 124 enables the digitization of clinical research studies as described herein by templatizing various data for clinical research study such that clinical research studies may be standardized and preformatted, and specific instances of clinical research studies may be rapidly designed. Such techniques as described herein enable the digitization of clinical research studies, clinical research study management, and clinical research study reporting requirements so as to obviate the performance of clinical research study management by hand. Therefore, the techniques of the disclosure improve efficiency and data quality, reduce submission cycle times, reduce the cumbersome administrative overhead of clinical research study management by hand, as well as reduce the potential for error or omission in critical recordkeeping.

As described herein, data for clinical research studies generated in accordance with the techniques of the disclosure are stored in database 105. The techniques disclosed herein further enable the use of a "lazy" copy algorithm to copy elements stored in database 105. Furthermore, techniques are disclosed herein for updating or deleting elements of the database where a lazy copy has been performed. In this manner, the techniques of the disclosure may allow for the use of lazy copy to increase performance of copying elements in a graph, even where the elements are members of a complex database such as a graph database, without substantially impacting the user experience or computing performance.

System 100 may be implemented on one or more computing devices that comprise processing circuitry and a memory. In some examples, the processing circuitry is one or more microprocessors, digital signal processors (DSPs), application specific integrated circuits (ASICs), field programmable gate arrays (FPGAs), or any other equivalent integrated or discrete logic circuitry, as well as any combinations of such components. In some examples, the memory is random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Further, this memory may be implanted entirely in hardware, software, or a combination thereof.

Figure 2:
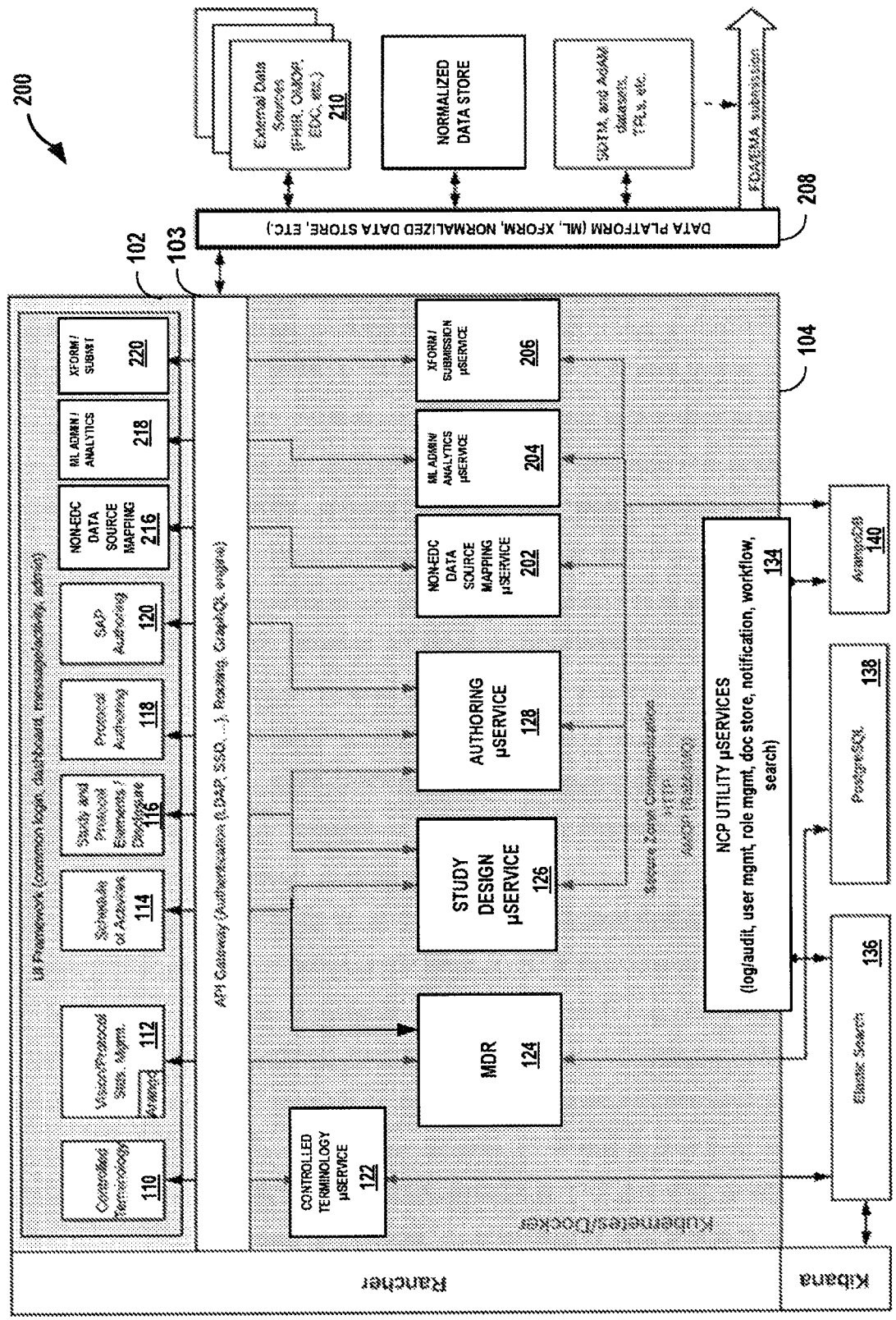
FIG. 2 is a block diagram illustrating another example system for generating a digitized framework for clinical development in accordance with the techniques of the disclosure.

FIG. 2 is a block diagram illustrating example system 200 for generating a digitized framework for clinical development in accordance with the techniques of the disclosure. System 200 may operate in a substantially similar fashion to system 100 of FIG. 1. However, system 200 includes additional application/microservice suites, such as non-EDC data source mapping application 216 and microservice 202, machine learning administration/analytics application 218 and microservice 204, and transform/submit application 220 and microservice 206.

System 200 may operate as an industry-wide integration platform and may support various partner- and customer-specific applications. For example, one partner may choose to specialize in non-EDC data source management, and so system 200 may provide non-EDC data source mapping application 216 and underlying microservice 202 to integrate and consume non-EDC oriented data sources such as the FHIR and OMOP standards. Such an application 216 and microservice 202 consumes content from MDR 124, including additional data standards definitions and mapping rules, to support cross-standard data normalization. Because MDR 124 is an ISO 11179-based implementation, MDR 124 is fully flexible and extensible to support wide ranges of data and other content standards in support of partner and customer goals.

In some examples, system 200 may implement machine learning in aspects of clinical lifecycle development as well as in analysis of legacy protocols and studies in support of future optimization efforts. For example, system 100 may embed machine learning analytics and administrative capabilities application 218 and accompanying machine learning analytics and administrative microservice 202 within microservices platform 104. System 100 may provide a common machine learning framework application and microservice suite in support of customer machine learning initiatives.

In some examples, system 100 implements a submission management application 220 and accompanying microservice 206. Such an application 220 integrates with an external data management platform 208 and/or data warehouse to trigger content extraction, transformation and assembly of submission materials, including CDISC submission data sets directly extracted from Study Design microservice 126 or other functional microservices. This submission management microservice manages submission packages to government authorities such as FDA and EMA, as well as tracks submissions as the submissions are processed.

Figure 3:
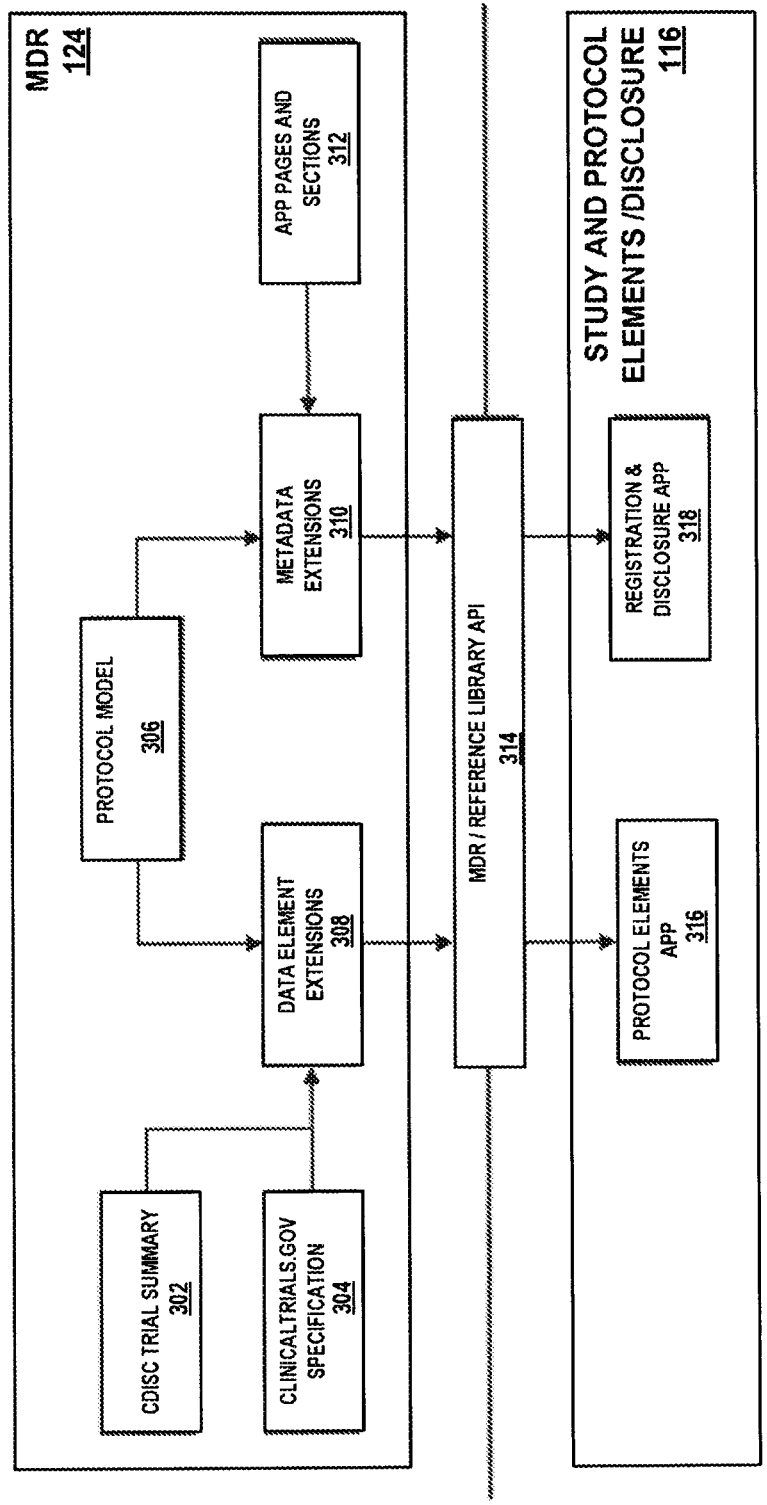
FIG. 3 is a block diagram illustrating interactions between the MDR and the Study and Protocol Elements application of FIG. 1 in accordance with the techniques of the disclosure.

FIG. 3 is a block diagram illustrating interactions between MDR 124 and Study and Protocol Elements application 116 of FIG. 1 in accordance with the techniques of the disclosure. MDR 124 stores and maintains metadata definitions as well as relationships with related metadata types. MDR 124 is an enterprise software system that provides metadata management for an end-to-end data lifecycle including public or private standards or data exchange formats, which can be any established norm or requirement with a formal document that establishes uniform engineering or technical criteria, methods, processes and practices. MDR 124 may implement one or more standards as an authoritative source and governance for creation of metadata as well as automatic inheritance and impact analysis of any proposed changes.

MDR 124 acts as a centralized repository of metadata assets associated with data collection, tabulation, analysis and other representational standards, and a governance platform that supports requirements through configuration, rather than hardcoded behavior requiring custom modification to adapt to changing requirements.

MDR 124 provides and maintains an asset library that stores assets, and presents an interface to index, search and selectively retrieve the assets from the asset library for reuse. In this way, MDR 124 may be implemented to provide, as one example, a centralized organizational metadata repository and governance solution for providing management of standards, semantics, and metadata associated with data collection. In general, MDR 124 allows users to manage metadata assets associated with data standards, where each of the assets is a separate collection of descriptive information about an accepted, standardized data element having semantic context for a given data standard, and where the asset is related in a hierarchical structure within an asset library where each respective asset may have one or more parent or child assets.

As such, entities may use MDR 124 to reuse the collection of information represented by any given asset for implementing different data standards. This may be particularly useful in situations where a standard is built on top of another standard. When this happens, MDR 124 allows users to advantageously create relationships to generic assets. For example, if each asset represents an XML element and each asset attribute represents an XML attribute for that respective XML element, then MDR 124 allows the assets to be used across standards and, for example, for creation of forms for collecting data and for tabulation and reporting of the data, i.e., throughout the entire process.

In some examples, the underlying physical data model used by standards specification and management system 18 may be based on an Object Management Group's (OMG) Reusable Asset Specification, such as Reusable Asset Specification Version 2.2, Object Management Group, November 2005, incorporated herein by reference. Physical content may be organized and constrained by a logical meta-model.

MDR 124 is an ISO/IEC 11179-based MDR. ISO/IEC 11179 standardizes the representation of metadata for an organization in an MDR and documents the standardization and registration of metadata to make data understandable and shareable. An MDR as defined by ISO/IEC 11179 specifies the use of one or more data elements. Each data element specifies a type of data and permits the use of only those values enumerated in a value domain to be used as valid values for the type of data. Further, ISO/IEC 11179 specifies the grouping of related data elements by a high-level concept and an object class, e.g., a data element concept. Additional description of data elements may be found in the ISO/IEC 11179 standard available from the International Organization for Standardization (ISO), the entire content of which is incorporated herein by reference. The baseline logical model provided by standards specification and management system 18 may be based on the ISO/IEC 11179 standard for metadata registries.

CDISC trial summary 302 and ClinicalTrials.gov specification 304 are examples of regulatory authorities, entities, or organizations that specify or receive submissions of clinical study data or clinical research study protocols. For example, a regulatory authority may use submitted data to ensure that proper procedures were followed during a clinical trial or study and/or to approve or reject the introduction of one or more products into the market. Although the techniques are described with respect to a clinical study, the techniques are not so limited and may be applied in other implementations where an agency or organization needs produce a detailed specification for controlling submission of data in accordance with a standard.

MDR 124 allows a user to automatically generate and manage metadata associated with client business objects. In some examples, the metadata may be associated with one or more standards (e.g., associated with one or more data models defined by a data standard). For example, a regulatory authority may define and promulgate one or more standards, such as a data collection standard, a data tabulation standard, or a data submission standard, to which MDR 124 adheres. For a given data submission standard being implemented, MDR 124 tabulates data submitted by users and formats the data according to the data submission standard.

MDR 124 implements one or more data models that represent a data standard for exchanging data. Each data model is a guide or specification that describe standardized data for collection and tabulation. As one example, a model associated with a standard data exchange for clinical research may identify data collection fields needed from a clinical, scientific and regulatory perspective to enable more efficient and consistent data collection at an investigative site. In one example, a model represents a data standard by defining a schema in accordance with a data description language, such as the extensible markup language (XML), JSON, or other languages not expressly described herein.

In this way, a model may represent a corresponding standard for describing and exchanging data, such as data for clinical studies, in a form that is vendor neutral and platform independent. More specifically, a model may specify a data standard for exchanging data via an XML schema, which uses schema components to define the meaning, usage and relationships of the elements that may be used within a class of XML documents, as well as permissible content, attributes, and values for the elements. In some examples, the data models may include, i.e., specify, assets that define objects for the data model.

MDR 124 operates as a fully integrated asset management system in which data specified in data guides or specifications for data standards are automatically processed and transformed into reusable assets. This metadata can be exported in submission standards such as ODM XML or Define XML, which is an XSD and specification relating business rules, for automatic generation of forms utilized by regulatory authorities.

In some examples, MDR 124 implements the Clinical Data Acquisition Standards Harmonization (CDASH) data collection standard, such as the CDASH v1.1 Standard developed by CDISC.ORG (which is one example of an industry standard) and/or sponsor-specific standards (e.g., pharmaceutical standards, contact research organization (CRO) standards, and/or device manufacturer standards). MDR 124 can be configured to support independent management of multiple sponsor standards in conjunction with shared global standards. This configuration is useful for Contract Research Organizations (CROs) that concurrently execute studies for numerous pharmaceutical, biotech and medical device providers.

In this configuration, the shared global standards (CDISC and/or CRO-defined) are managed at the top (Enterprise) organization of MDR 124. A suborganization is created for each sponsor and clearly named to be easily identifiable as associated with that sponsor. Sponsor-provided and sponsor-specific (i.e., developed by the CRO specifically in support of a sponsor) standards are populated in the suborganization for that sponsor. System users are then assigned specific organizations for which they are allowed access.

For example, User A may be allowed to access Sponsor 1, User B may be allowed to access Sponsor 2, and User C may be allowed to access Sponsors 1, 2 and 3 and the Enterprise (CRO) organizations. When a user logs into system in this configuration, they select an organization for which they are working for the duration of that user session. That user is then allowed to view only those standards contained in the specific organization which they selected, along with the global standards at the Enterprise level if the selected organization is a sponsor organization.

This organizational hierarchy approach may provide two major benefits to a CRO. First, each sponsor is freely able to share/reuse CRO global standards as part of their sponsor-level definitions, where this can greatly improve efficiency for the sponsor as the CRO may have well-defined standards in areas that the sponsor would otherwise have to itself define and develop. Second, users are strictly limited to access standards for only those sponsor organizations for which they have been assigned. For example, Sponsor 1 and Sponsor 2 may establish contractual stipulations that CRO individuals directly assigned to sponsor-specific work may be limited to view only CRO shared standards and sponsor-specific standards for the duration of the contract.

In this respect, User A and User B in the above example are dedicated to Sponsor 1 and Sponsor 2, respectively. CRO oversight personnel (e.g., User C) are configured to have viewing rights to all sponsor standards along with direct access to CRO shared standards. CRO oversight personnel may be configured to have such viewing rights so that they can provide guidance to sponsor-specific users when confronted with difficult standards modeling decisions, and maintain and enhance CRO global standards over time so as to improve the efficiency of sponsor work done by the CRO.

In any event, the CDASH standard may be represented by a declarative XML-based data model conforming to the CDISC Operational Data Model (ODM). The XML-based model facilitates the regulatory-compliant acquisition, archive and interchange of metadata and data for clinical research studies. As one example, a regulatory-compliant standard for exchanging clinical research may be specified in accordance with the CDISC Operational Data Model Version 1.3.2 available from CDISC.ORG. In other examples, one or both of the data tabulation standard and/or the data submission standard may conform to a Study Data Tabulation Model (SDTM) data standard and/or an ADaM data standard.

As an example data model, MDR 124 incorporates protocol model 306. The protocol model defines a set of data elements, controlled terminology, and relationships based on existing industry and/or sponsor-specific standards which would be leveraged to automate the transfer and re-use of the same data by different systems. The protocol model enables the platform to be used by different study sponsor organizations and a broad range of vendor types and vendor systems. Foundational industry standards (CDISC (SDTM, ODM-XML, CTR-XML, etc.), TransCelerate Common Protocol Template (CPT) libraries, Clinical Trials.gov, EudraCT, HL7/FHIR) are leveraged to define the data elements of the protocol model. The protocol model uses industry standards, such as CDISC, LOINC, SNOMED, MedDRA, ICD9/10, IDMP) to control terminology and relationships to identify additional components from other libraries (CDISC Library, Sponsor Global Libraries) which identify data to be received during defined study time periods which is stored in additional data elements of the protocol model.

MDR 124 implements a full metadata model including various reference libraries, such as Program and Study Design Elements, Objective and Endpoint Templates, Biomedical Concepts, and Study Activities. MDR 124 also holds various clinical data standards, such as Collection Standards, Tabulation Standards, and Analysis Standards. MDR 124 may provide these standards as linked data, including tracing Indication to Objective to Endpoint to Biomedical Concept to Defined Study Activity, and from there further on to Collection, Tabulation, and Analysis Standards. Furthermore, MDR 124 extends the metadata model to include all data elements defined by CDISC Trial Summary Domain and ClinicalTrials.gov specifications.

MDR 124 implements a data model that specifies a data standard representative of requirements for regulatory-compliant exchange of data between entities and stores metadata for the data model. As described herein, the data model includes one or more client business objects. MDR 124 includes data element extensions 308 and metadata extensions 310 that extend the data model set forth in ISO 11179 and/or sponsor-specific standards.

Metadata element extensions 308 include extensions to the business objects to specify one or more study events. Each study activity may be, e.g., a clinical assessment or procedure to be performed on a subject, a data element to be measured from the subject, an assemblage of already existing data about the subject, or collection of non-treatment related data (e.g., healthcare utilization) from the subject. For example, a study event for a study objective may occur on a periodic basis (e.g., daily, weekly, or monthly) and specify a study activity to be performed, for example, that a subject's blood pressure and heart rate be monitored. In accordance with the techniques of the disclosure, a clinical research study may be quantized into a sequence of such study events and study activities, and thereby objectively defined and measured.

Data element extensions 310 extend the data elements of ISO 11179 to include one or more properties for each of the client business objects. MDR 124 may use the properties to organize the client business objects into one or more property groups. Each property specifies a value for a property type for the property. For example, the property type may be one of a date, a time, a string, a uniform resource locator (URL), a Boolean, or an integer. In some examples, one may enumerate one or more valid property types (e.g., as a predefined string or integer list of valid values), where a valid property specifies one of the enumerated property types specified by the predefined list.

In some instances, each of the one or more properties are strongly typed. In some examples, each of the one or more properties specifies a dependent relationship to another property of the one or more properties. In other examples, a property may be compound (i.e., composed of two or more simple properties). Each property group specifies, for example, an ordinality of the property group in a property group hierarchy or a business object within a microservice associated with the property group. In some examples, each property group comprises a clinical research study, a clinical research study protocol, a clinical research study version, a clinical research study design, or a clinical research study.

Properties and property groups are managed as MDR-governed standards and are specified alongside other clinical standards elements, such as CDISC 302 and internal organizational data standards (including sponsor-specific standards). These standards are grouped into a standards collection (i.e., study template) that is managed and versioned within MDR 124. Each version of the standards collection is assigned an Effective Date attribute. MDR 124 uses this Effective Data attribute to automatically select the correct standards collection version to be used as the template for a newly instantiated Study. Properties and property groups are used to implement protocol model 306 as described above. An example property is masking, which has a type Value Domain, so the Masking property in turn references an ISO 11179 Value Domain for Masking, which contains a set of enumerated Domain Values. The enumerated domain values are the only valid values for the value domain masking type, which ensures consistency in metadata across multiple organizations by forcing a user to use only enumerated values when describing data elements.

MDR 124 exposes properties and property groups to applications and microservices via a GraphQL API. With respect to FIG. 1, study design microservice 126 consumes properties and property groups to populate study creation elements. Additionally, Study and Protocol Elements application 116 uses properties and property groups to specify the broad range of data required to fully instantiate a study. A Study Disclosure application may reuse study planning and execution content alongside user-populated study finalization and submission related elements such as governing authority mandates. Further, properties may be configurable elements within objective and endpoint templates used in support of Schedule of Study Activities automation as described herein.

MDR 124 implements properties and property groups as logical class models. Properties are strongly typed, and support property types such as String, URL, Value Domain, Boolean, Date, Timestamp, Time, Integer, Decimal, User, and Compound. Most property types are represented by a LiteralPropertyDefinition subclass. Value Domain properties are represented by a TermPropertyDefinition subclass which references a Terminology Domain (Value Domain) and Terms (Domain Values). Values for term properties may also be dynamically derived via connection to system microservice (e.g., User) or external systems. Compound property types may be composed of two or more simple property types as listed above.

Properties share a set of common configuration elements via a class inheritance structure. Common configuration elements may include, e.g., display name, cardinality, required and multivalued flags, and read-only setting. Each individual type in turn receives type specific elements from its subclass. For example, ordered literal property types such as Integer, Decimal, Date and Timestamp add upper bound and lower bound settings.

Properties may in turn be assembled into Property Groups, where context-specific configuration elements such as ordinality and the associated microservice field name are specified. Property Groups themselves have configuration elements such as display name, and can be assembled by parent groups with each level establishing group-level ordinality as needed.

Properties can also be grouped into dependent relationships. For example, a property specifying a valid set of Indications to be presented when creating a study may depend on a value previously specified for a Therapeutic Area property. Properties can also be grouped into compound assemblies. For example, one may combine a Value Domain property comprising Day, Week, Month, or Year with a positive integer property to represent a study event within the specification of an Endpoint.

Applications 312 of UI framework 102 may invoke metadata extensions 310 to parameterize objective and endpoint templates. In some examples, MDR 124 may further generate, based on the template, one or more study sections each of which is composed of one or more study elements. In some examples, system 100 may further generate, based on the template, at least one study objective and at least one study estimand or endpoint (referred to herein as "endpoint") that may be used to facilitate generation of key activities and events within a schedule of study activities.

These templates parameterize information for scientific hypotheses and link these to associated biomedical concepts and activities that are applicable to those concepts. A clinician may specify objectives and endpoints for the clinical research study based on template constraints, including an identification of study events in support of analysis of the scientific hypotheses. These study events, coupled with the previously mentioned study activities, serve as a basis for automatically generating key aspects of a schedule of activities for the clinical research study. The study activities indicate which clinical observations need to be performed and the study events indicate when these observations need to be scheduled, so that the results of these observations can be used to validate if the study has met the endpoint according to the statistical hypothesis of the study. The clinician may use the generated schedule of activities to guide data collection in support of the scientific hypotheses of the clinical research study.

For example, as described herein, objective and endpoint templates extend the use of properties to support dynamic user-driven objective and endpoint specification within Study and Protocol Elements application 116 of FIG. 1. The objectives and endpoints editor of application 116 presents this templatized information in a structured way such that the clinician can specify key aspects of the study. The specified endpoints are further presented to the clinician in Schedule of Activities application 114 of FIG. 1. When creating the study events in the schedule using this application, the user is offered suggestions about including certain study events based on the content of the endpoints. These templates are similar to property groups in that the templates contain properties as part of their definition. Objective and endpoint templates include objective or endpoint-specific information, such as objective type, study type, indication (for objective templates), and biomedical concept and associated study activities (for endpoint templates). Objective and endpoint templates further include a tokenized string representing the configurable objective or endpoint text and associated named properties for each of the tokenized string elements.

Study and Protocol Elements application 116 renders these templates into a configurable form where a user may specify concrete values in combination with template-specific default and read-only values. Study and Protocol Elements application 116 uses these values, in combination with a parameterized string representation of the Objective or Endpoint, to render a human-readable sentence representing the Objective or Endpoint that is processed by protocol authoring application 118, and in the case of an Endpoint, stored for downstream system use in generating Schedule Study events and corresponding Study activities. Each parameter is the parameterized string is associated with a specific property of the template such that a human readable phrase is produced upon processing of the string and associated properties as specified by the Objective or Endpoint template. In some examples, a property may be specified as multi-valued (e.g., a property representing a Study Event for which data supporting an Endpoint is to be collected). The human readable phrase rendered from such a configuration may take into account grammatical rules (e.g., if multi-valued Secondary Study Event property of an Endpoint template has been specified to include Week 4, Week 8, and Week 12 as values, string rendering processing must produce grammatically correct output such as "The percentage change in HbA1c from Baseline to Week 4, Week 8 and Week 12"). For example, protocol elements application 316 (which may represent an example of study and protocol app 116 of FIG. 1) may invoke properties and property groups to parameterize objective and endpoint templates in the creation of a study. Registration and disclosure application 318 may invoke properties and property groups when generating disclosure submissions mandated by regulatory authorities.

Figure 4:
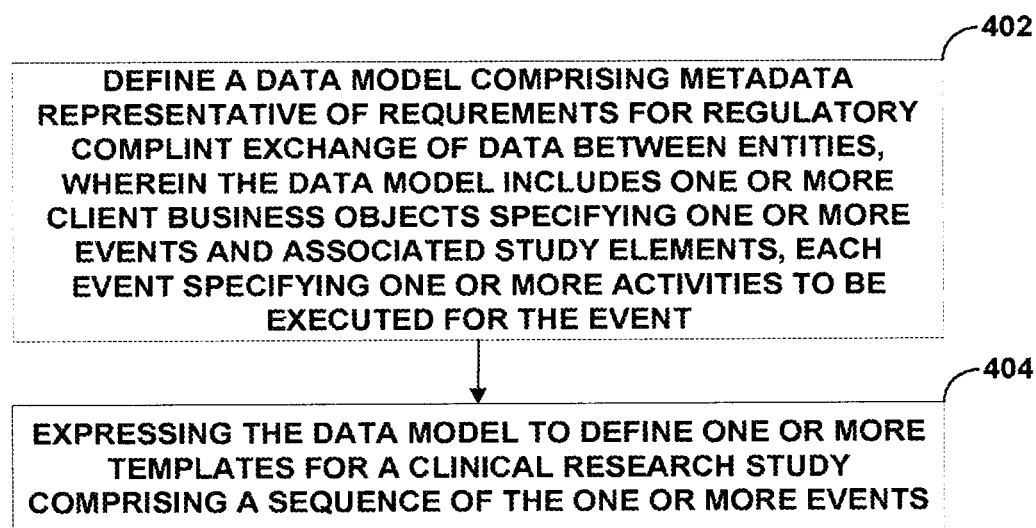
FIG. 4 is a flowchart illustrating an example operation to obtain template information from an MDR in accordance with the techniques of the disclosure.

FIG. 4 is a flowchart illustrating an example operation to obtain template information from an MDR in accordance with the techniques of the disclosure. MDR 124 defines a data model comprising metadata that specifies a data standard representative of requirements for regulatory-compliant exchange of data between entities (402). In some examples, MDR 124 stores the data model in an ISO 11179-based MDR database. The data model conforms to a data description language and specifies which data elements must be collected and a format in which the data elements are to be collected. The data model includes one or more client business objects representing aspects of a well-structured pharmaceutical clinical research study. As described herein, a clinical research study is, for example, a research project whose objectives are to test or confirm hypotheses concerning the utility, impact, pharmacological, physiological, and/or psychological effects of a particular treatment, procedure, drug, device, biologic, food product, cosmetic, care plan, or subject characteristic.

Each client business object specifies one or more study events and associated study elements for a clinical research study. Each study event specifies one or more study activities to be executed for the study event. Each study activity may be, e.g., a clinical treatment or procedure to be performed on a subject, a data element to be measured from the subject, an assemblage of already existing data about the subject, or collection of non-treatment related data (e.g., healthcare utilization) from the subject.

The data model further includes one or more properties for each of the client business objects; these properties may be in turn organized into one or more property groups representing the client business objects. Each property specifies a value for a property type for the property. For example, the property type may be one of a date; a time; a string; a uniform resource locator (URL); a Boolean; or an integer. In some examples, one may enumerate one or more valid property types (e.g., as a predefined string or integer list of valid values), wherein a valid property specifies one of the enumerated, valid property types specified by the predefined list. In other examples, the valid value list may be dynamically retrieved from system microservices (e.g., users based on roles as specified by the combination of the user microservice and the access control microservice) or from external systems (e.g., protocol numbers as specified by an external CTMS system). In other examples, a property may be specified as compound (i.e., composed of two or more simple properties of the above types).

In addition, conditional property specifications, where default contextual properties are modified given a specific set of conditions, are also supported. For example, a property A may become editable only when a property B contains a specific value, or when property B is populated with any value. Conditions may span multiple specified values for a designated property (e.g., property C must be set to one of values x, y or z for the condition to be in effect) and may span multiple designated properties (e.g., the conditional rules for properties D, E and F must all be met for the condition to be in effect).

Each of the one or more properties are strongly typed. In some examples, each of the one or more properties specifies a dependent relationship to another property of the one or more properties. Each property group specifies, for example, an ordinality of the property group in a property group hierarchy or a microservice associated with the property group. In some examples, each property group comprises a clinical research study, a clinical research study protocol, a clinical research study version, a clinical research study design, or a clinical research study.

MDR 124 expresses the data model to define one or more templates for a clinical research study comprising a sequence of the one or more study events and associated study elements (404). To support the digitized framework for clinical development described herein, MDR 124 extends the data model set forth in ISO 11179. For example, MDR 124 implements a data model that specifies a data standard representative of requirements for regulatory-compliant exchange of data between entities and stores metadata for the data model. As described herein, the data model includes one or more client business objects representing aspects of a well-structured pharmaceutical clinical research study. As described herein, a clinical research study is, for example, a research project whose objectives are to test or confirm hypotheses concerning the utility, impact, pharmacological, physiological, and/or psychological effects of a particular treatment, procedure, drug, device, biologic, food product, cosmetic, care plan, or subject characteristic.

MDR 124 extends each client business object to represent a clinical research study or associated study element, whereas each clinical research study in turn specifies one or more study events. Each event specifies one or more study activities to be executed for the corresponding study event. MDR 124 further extends the data model of ISO 11179 to include one or more properties for each of the client business objects that organize the client business objects into one or more property groups. These properties and property groups are used to represent both cohesive collections of study elements (which may be referred to as "sections") and configurable elements of objective and endpoint templates.

The extended data model implemented by MDR 124 enables the digitization of clinical research studies as described herein by templatizing various data for clinical research study such that clinical research studies may be standardized and preformatted, and specific instances of clinical research studies may be rapidly designed. Such techniques as described herein enable the digitization of clinical research studies, clinical research study management, and clinical research study reporting requirements so as to obviate the performance of clinical research study management by hand. Therefore, the techniques of the disclosure may improve efficiency and data quality, reduce submission cycle times, reduce the cumbersome administrative overhead of clinical research study management by hand, as well as reduce the potential for error or omission in critical recordkeeping.

MDR 124 may optionally express the data model to define at least one study objective and at least one study endpoint which may be used to facilitate generation of a sequence of the one or more study events and key activities for the events. For example, MDR 124 expresses one or more properties for each client business object specified by the one or more templates to define one or more study objective templates and one or more study endpoint templates. In some examples, system 100 may parameterize one or more templates for the clinical research study based on the user input to obtain a schedule of study activities to be executed for each study event of the sequence of the one or more study events.

FIG. 5 is a block diagram illustrating example query data structure 500 for a study template in accordance with the techniques of the disclosure. Query data structure 500 lists the set of queries supported by the GraphQL API of system 100 of FIG. 1. Query data structure 500 uses a mix of data standards queries (such as propertyGroupByNameVersion and objectiveTemplatesByIndication) and protocol and study instance-specific (such as studies) queries are present. Data standards queries are provisioned into the federated system's GraphQL API by MDR 124 of FIG. 1, whereas instance-specific queries are provisioned by Study Design microservice 126 o FIG. 1. As depicted in the example of FIG. 5, query data structure 500 includes the following data fields: businessObject, definedActivities, definedActivity, definedActivityFilterByID, definedActivityFilterDomains, definedActivityFilterByDomains, endpointTemplate, endpointTemplates, exportFormats, features, getSchedulePDF, health, object, objectiveTemplate, objectiveTemplates, objectiveTemplatesByIndication, pingStudyDesign, propertyGroup, propertyGroupByNameVersion, studies, and terms. The foregoing data fields are provided as examples only, and other implementations of the techniques of the disclosure may use only a portion of the foregoing data fields or additional data fields not expressly described herein.

Figure 6:
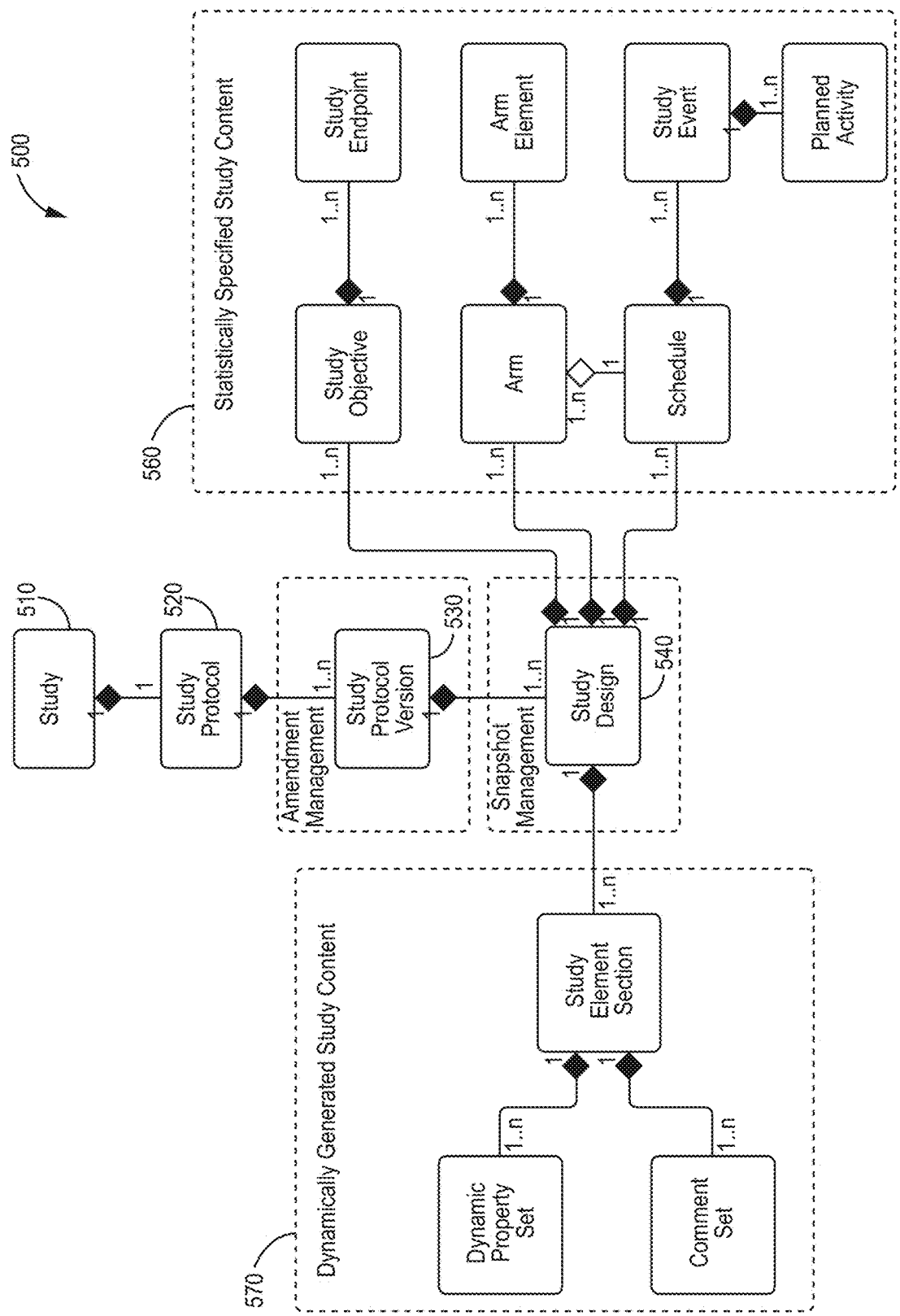
FIG. 6 is a block diagram illustrating an example data system for a clinical research study template in accordance with the techniques of this disclosure.

FIG. 6 is a block diagram illustrating example data system for a clinical research study template in accordance with the techniques of the disclosure. Data system 500 include a number of interconnected data structures 510-560. Study data structure 510 is the entry point to study and protocol content that is managed by Study Design microservice 126 of FIG. 1. Study data structure 510 serves as an anchor point for Study Protocol data structure 520, which binds a corresponding user or users who own a protocol for purposes of attribute-based access control.

Attributes specified during study creation such as Therapeutic Area, Indication, Study Type, Study Phase, Participant Type and Compound may be persisted as part of the Study object, and may be used as filter attributes to determine user eligibility for a configured role in system 100. For example, an organization may choose to assign users to specific Therapeutic Areas. As such, each user profile as managed by User microservice 134 will then be populated with one or more Therapeutic Area values for which they are eligible. At time of user login into system 100, Access Control microservice 134 retrieves the set of Therapeutic Area values for the user and incorporates these values into role and permission evaluation.

A user assigned to Therapeutic Area A may, in this example, not be allowed to own, view, or otherwise access Studies created for other Therapeutic Areas. Study data structure 510 includes the following data fields: internalID, ID, owner, protocol, and revision. The foregoing data fields are provided as examples only, and other implementations of the techniques of the disclosure may use only a portion of the foregoing data fields or additional data fields not expressly described herein.

Study protocol data structure 520 serves as an anchor point for the potentially multiple versions of a study that are produced over the life of the study and that system 100 of FIG. 1 manages to implement a digitized protocol. Study protocol data structure 520 may include the following data fields (which may be persisted via dynamic property capabilities in which certain properties are automatically inherited, generated, and/or created due to definition of templates for clinical research studies): internalID, addedOnToExistingTreatments, agencyIDs, aLocation, boardApproalStatus, caApplicantType, citations, companionStudies, compound, confirmedResponseMinimumDuration, country, currentTherapyOrTreatment, currentVersion, extensionTrialIndicator, ID, Indication, InterventionModel, InterventionModelOtherValue, InvestigationalTherapyOrTreatment, keywords, masking, participant, pharmacologicClass, plannedSubjects, plannedTreamentDuration, plannedTrialDuration, program, protocolNumber, protocolTemplate, pubmedCitationID, responsibleParty, revision, sexOfParticipants, sponsorStatus, stableDiseaseMinimumDuration, stratificationFactor, study, studyDescription, studyPhase, studyStopRules, studyType, studyURL, substudyDetails, substudyPlannedIndicator, supportOrganization, therapeuticArea, trialIntent, trialIntentOtherValue, trial Scope, and versions. Again, the foregoing data fields are provided as examples only, and other implementations of the techniques of the disclosure may use only a portion of the foregoing data fields or additional data fields not expressly described herein.

Study protocol version data structure 530 may support a clinical research study template in accordance with the techniques of the disclosure. Study Protocol Version data structure 530 may serve as the anchor point for each version (original or amendment) produced in the course of study planning and execution. Study protocol version data structure 530 includes the following data fields (which similarly may be persisted via dynamic property capabilities in which certain properties are automatically inherited, generated, and/or created due to definition of templates for clinical research studies): internalID, amendment, approvalDate, creationDate, designs, ID, lastModificationDate, ordinal, protocol, protocolAcronym, protocolShortTitle, protocolStatus, protocolTitle, revision, and studyElementObjectID. As noted above, the foregoing data fields are provided as examples only, and other implementations of the techniques of the disclosure may use only a portion of the foregoing data fields or additional data fields not expressly described herein.

Study design data structure 540 may further support a clinical research study template in accordance with the techniques of the disclosure. Study design data structure 540 may serve as the collection of all study protocol version data elements 530, and enables these study protocol version data elements 530 in aggregate to be saved and restored as a snapshot. Snapshots allow users to save their work at checkpoints and if desired return to one of those checkpoints as needed should future study definition work be determined to be incorrect or otherwise problematic. Study design data structure 540 may include the following data fields: internalID, arms, elements, epochs, ID, label, lastModificationDate, lastModificationUser, objectives, ordinal, protocol Version, revision, schedules, and studyActivities. Once again, the foregoing data fields are provided as examples only, and other implementations of the techniques of the disclosure may use only a portion of the foregoing data fields or additional data fields not expressly described herein.

Study design data structure 540 consists of two primary categories of content: schedule and arm related content, and section-related lock state, properties and comments. Schedule and arm related content consists of Objectives and Endpoints, Arms and Arm Elements, and Schedules, Study Events and Planned Activities. Section-related content consists of Study Element Sections, Dynamic Property Sets and Comment Sets.

In other words, study data structure 510 is (as noted above) the entry point to study and protocol content that is managed by Study Design microservice 126 of FIG. 1. Study data structure 510 serves as an anchor point for study protocol data structure 520 and contains mandatory data fields (which may be another way to refer to "study design elements") specified during study creation such as Therapeutic Area, Indication, Study Type, Study Phase, Participant Type and Compound. These attributes characterize the study and are thus immutable upon study creation. They may also be used to assist, via attribute-based access control mechanisms implemented by system 100, in binding specific users to the study.

In some instances, attribute-based access control enables use of these attributes within filters that are then used to determine user eligibility for a configured role (e.g., study owner, study protocol editor, etc.) in system 100. For example, an organization may choose to assign users to specific Therapeutic Areas. As such, each user profile as managed by User microservice 134 will then be populated with one or more Therapeutic Area values for which the associated users are eligible. At time of user login into system 100, access control microservice 134 retrieves the set of Therapeutic Area values for the user and incorporates these values into role and permission evaluation. In this manner, a user assigned to Therapeutic Area A in this example is not allowed to own, view, or otherwise access Studies created for other Therapeutic Areas. The foregoing data fields discussed above are provided as examples only, and other implementations of the techniques of the disclosure may use only a portion of the foregoing data fields or additional data fields not expressly described herein.

Study protocol data structure 520 serves as an anchor point for the potentially multiple versions of a study protocol that are produced over the life of the study and that system 100 of FIG. 1 manages to implement a digitized protocol. As such, study protocol data structure 520 contains an immutable Protocol Number data field that is specified at time of study creation, along with a collection of all study protocol versions in existence for the study and specific references to the original and currently active study protocol version. The foregoing data fields are provided as examples only, and other implementations of the techniques of the disclosure may use only a portion of the foregoing data fields or additional data fields not expressly described herein.

Study protocol version 530 serves as the anchor point for each version (original or amendment, and minor versions of the same) produced in the course of study planning and execution. As such, the study protocol version data structure includes the following data fields: amendment version (major and minor), creation date, approval date, and mutable study protocol attributes such as protocol title, protocol short title, protocol acronym and protocol keywords. Study protocol version also maintains a reference to the currently active study design along with a collection of all study designs in existence for the study protocol version. The foregoing data fields are provided as examples only, and other implementations of the techniques of the disclosure may use only a portion of the foregoing data fields or additional data fields not expressly described herein.

Study design data structure 540 may serve as the collection of all Study Protocol Version data structures and elements, and enables these data structures and elements in aggregate to be saved and restored as a snapshot. Snapshots allow users to save their work at meaningful checkpoints and if desired return to one of those checkpoints as needed should future study definition work be determined to be incorrect or otherwise problematic. Only the currently active study design as referenced by the study protocol version may be updated in the course of study protocol development.

Study design content can be further classified into one of two content categories: statically specified (or in other words, fixed) study protocol elements (shown as statically specified study content 560) and dynamically generated elements (shown as dynamically generated study content 570). For example, statically-specified study content 560 may include Objectives and Endpoints, Arms and Arm Elements, and Schedules, Study Events and Planned Activities, each of which supports aspects of study design as discussed throughout this disclosure. Dynamically generated study content 570 may include a representation of section-related content via Study Element Sections. Each Study Element Section may in turn consist of a section locked element, Dynamic Property Sets and Comment Sets. A Dynamic Property Set represents the manifestation of a specific dynamic property group with its collection of dynamically configured properties as discussed throughout this disclosure. A Comment Set represents a collection of informal thread-based communications created by Study role-players as appropriate to assist in section specification decisions made over the course of Study Element Section development and review. The foregoing data fields are provided as examples only, and other implementations of the techniques of the disclosure may use only a portion of the foregoing data fields or additional data fields not expressly described herein.

The section locked element of a Study Element Section is used in combination with user access control permissions to control the ability to update the content of the associated section, and can also be used to validate whether updates to related sections are allowed (e.g., a user who has update permission for the Schedule section may still be prevented from editing that section until the Arms section is locked; a user attempting to submit a Study Protocol Version for approval may be prevented from that submission if Lean Protocol is installed and the Lean Protocol section is unlocked). In support of these and other permissions validation requirements, the Study Design service integrates a configurable rules engine. For example, when a user attempts to update a specific Study Element Section, the rules engine looks up the section, verifies that it is under a Study Protocol Version that is not in an approved state, checks that the properties in the section are valid, and then does an Access Control check to make sure the user has permission to lock the section.

In this way, dynamically generated study content 570, which includes dynamic property set, comment set, and study element section, are dynamically configured from MDR 124, where property and property groups flow from MDR 124 (e.g., MDR 124 provides the structure, users enter information with respect to such structure, and MDR 124 dynamically persists the information entered by the users via a dynamic properties microservice). MDR 124 may, in other words, specify properties and/or property groups as key-value pairs so that such properties and/or property groups can be resolved into a cohesive object. For example, 100 or more attributes (which is another way to refer to properties) may result in a single object type.

In addition, the template represented by data system 500 (and which may, as a result, be referred to as template 500) may parameterize what normally would be entered as a text phrase (e.g., in a document defining a study). For example, a scientific hypothesis specification may be entered (e.g., "To evaluate the efficacy of ZD 5 mg Daily/Oral administered to individuals with Type 2 Diabetes Mellitus (T2DM) "), whereupon study design microservice 126 may parse such text phrase representative of the scientific hypothesis specification to identify parameters by which to identify attributes to which system 100 may automate against. Study design microservice 126 may generate endpoints as part of statically specified study content 560, where in the example above such endpoints may include "The absolute change in HbA1c from Baseline to Week 4, Week 8 and Week 12), "The percentage of patients with HbA1c (%)<10% at Week 10," etc.

Study and protocol elements user interface 116 may enable editing of objectives and definition of different endpoints to facilitate dynamic generation of the study. In the immediately proceeding examples, the values "Baseline", "Week 4", "Week 8", "Week 10", and "Week 12" represent Study Events that may be automatically populated into a Schedule for the Study. The edits all flow to template 500 and create additional arms, arm elements, schedules, events, activities, etc, as described above. Study design 540 may control which of the created events, activities, etc. are to be performed and/or edited, using template 500 as a definition for mandatory activities and events, thereby allowing template 500 from MDR 124 to establish secure and safe clinical research studies that adhere to formal and/or sponsor standards while also potentially permitting expedient study research as such templates may be reusable and allow for faster study design.

Figure 7:
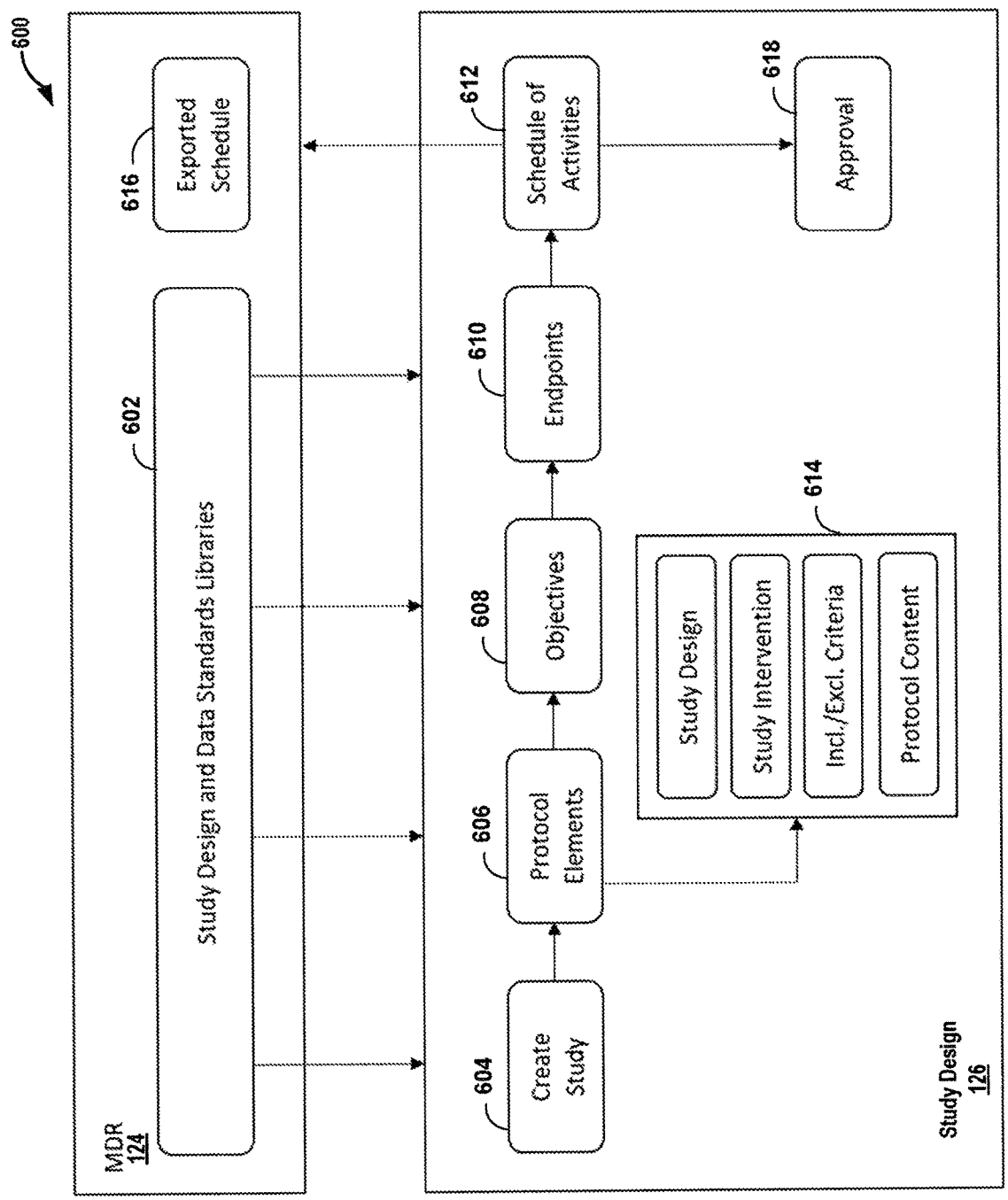
FIG. 7 is a flowchart illustrating an example operation for designing a clinical research study in accordance with the techniques of the disclosure.

FIG. 7 is a flowchart illustrating an example operation for designing a clinical research study in accordance with the techniques of the disclosure . . . FIG. 7, in other words, illustrates an operation for creating a clinical research study during which a user initiates a new study, defines protocol level content, sets up objectives and endpoints, defines a schedule of study activities, reviews a version history of the study, and submits changes to the study for approval. The operation of FIG. 7 may be executed by study design microservice 126.

Study design microservice 126 receives, as process inputs, metadata from a metadata library of MDR 124, external data, and protocol data elements (602). Study design microservice 126 may receive, from a user, an indication to create a study (604). In some examples, UI framework 102 allows a user to initiate a study from an authorized list of studies or allows the user to initiate a study by defining a new study via study attributes provided by the user. To initiate a study from an authorized list, UI framework 102 may present, to the user, one or more approved studies for selection by the user. The user may select a study program or provide a study protocol number. UI framework 102 may prepopulate one or more study attributes of the selected study for presentation to the user for review.

To initiate a study by defining a new study, UI framework 102 allows to define a new study, provide study attributes such as a study ID, protocol title, and protocol acronym. UI framework 102 may further prompt the user to select a compound, study phase, study type, participant type, and therapeutic area, or indication. Additionally UI framework 102 may present the user with an Effective Date value defaulted to current date but which the user can modify to specify a date in the past and is used to select the correct version of study template (i.e., standards collection) based on the algorithm previously described. Typically, UI framework 102 provides, to the user, a list of valid options for each element of the study. Some elements may be dependent on other elements selected by the user; for example, UI framework 102 may not allow the user to select an indication until the user specifies a therapeutic area.

Study design microservice 126 receives, from a user, protocol content for specifying a protocol for the study (606). This allows study design microservice 126 to capture key attributes for the protocol, such as study long name, short name, acronym, study blinding, treatment administration, comparator arms, or other defined fields. UI framework 102 may provide, to the user, a drop-down menu of choices to specify data for the protocol, such as a study intent.

Study design microservice 126 retrieves, possibly prior and/or concurrent to the protocol content being defined or potentially after the user has defined the protocol content, from the reference library of MDR 124 the relevant set of objective templates (608) and endpoint templates (610) based on prior specified data elements for the study such as Therapeutic Area and Indication. Study design microservice 126 parameterizes the templates based on input from the user and full metadata defined by the reference library of MDR 124. This configuration further generates relationships between indications and objective templates and relationships between objective templates and endpoint templates.

Study design microservice 126 adds an objective or endpoint to a study by parameterizing an objective or endpoint template. Study design microservice 126 may use, e.g., parameters bound by the template, study parameters, or metadata data elements specified by MDR 124 to parameterize the templates. Further, Study design microservice 126 may parameterize the templates based on input received from the user via UI framework 102. Study design microservice 126 assembles a description of the objectives or endpoints based on the parameterized data.

Study design microservice 126 specifies a data model that relates arms to interventions (many-to-many) consistent with CT.gov submission requirements, while also integrating drug administration information that can be related to product information compliant to the ISO standard for the identification of medicinal products (IDMP data model). For example, a treatment arm may include more than one intervention (e.g., for a combination therapy), and a medicinal product may be administered in multiple ways (e.g., dosage level) within a schedule.

Study design microservice 126 further generates one or more of study design, study intervention, inclusion and/or exclusion criteria, and protocol content for the study (614). For example, a study builder defines and manages a schedule for the clinical research study based on defined protocol content. Schedule of Activities application 114 defines and manages the schedule based on the defined protocol content. Schedule of Activities application 114 enables the selection and definition of desired assessments and measures to be collected within protocol content (616). Once the user has completed the study and reviewed the study content, study design microservice 126 allows the user to approve the study (618). UI framework 102 may thereafter display the approved study as read-only and disallow subsequent changes to the study. However, UI framework 102 may still provide a mechanism for the user to review the study.

Further, UI framework 102 may allow the user to define an amendment (i.e., change to the scientific experiment expressed by the study) or minor version (e.g., corrections to the study specification that do not result in meaningful change to the scientific experiment expressed by the study) to the study and submit the amendment for approval. The amendment or minor version may specify an edit or change to the study arm of the study. UI framework 102 may also display a version history including a list of approved versions of the study and a status of submitted amendments.

As described in more detail below with respect to Lean Protocol Microservice 9404, a Gate instance supports a fixed state machine that includes In Progress, Ready for Review, Under Review, and Approved states. This four-state model is applied to approval of StudyProtocolVersion as well. For example, when Lean Protocol application is present, the Approve action on StudyProtocolVersion in UI Framework 102 is augmented by a collection of one or more StudyProtocolVersion gates in Lean Protocol application 9402, each of which assembles relevant section locks as represented by Study and Protocol Elements application 116, Schedule of Activities application 114, Protocol Authoring application 118, etc., to the minimum set required as a precursor to approval of the StudyProtocolVersion (e.g., because some Study and Protocol Element application sections may be informational and not mandatory). Additional discussion of the Lean Protocol Microservice and corresponding state machine is set forth in more detail below.

Figure 8:
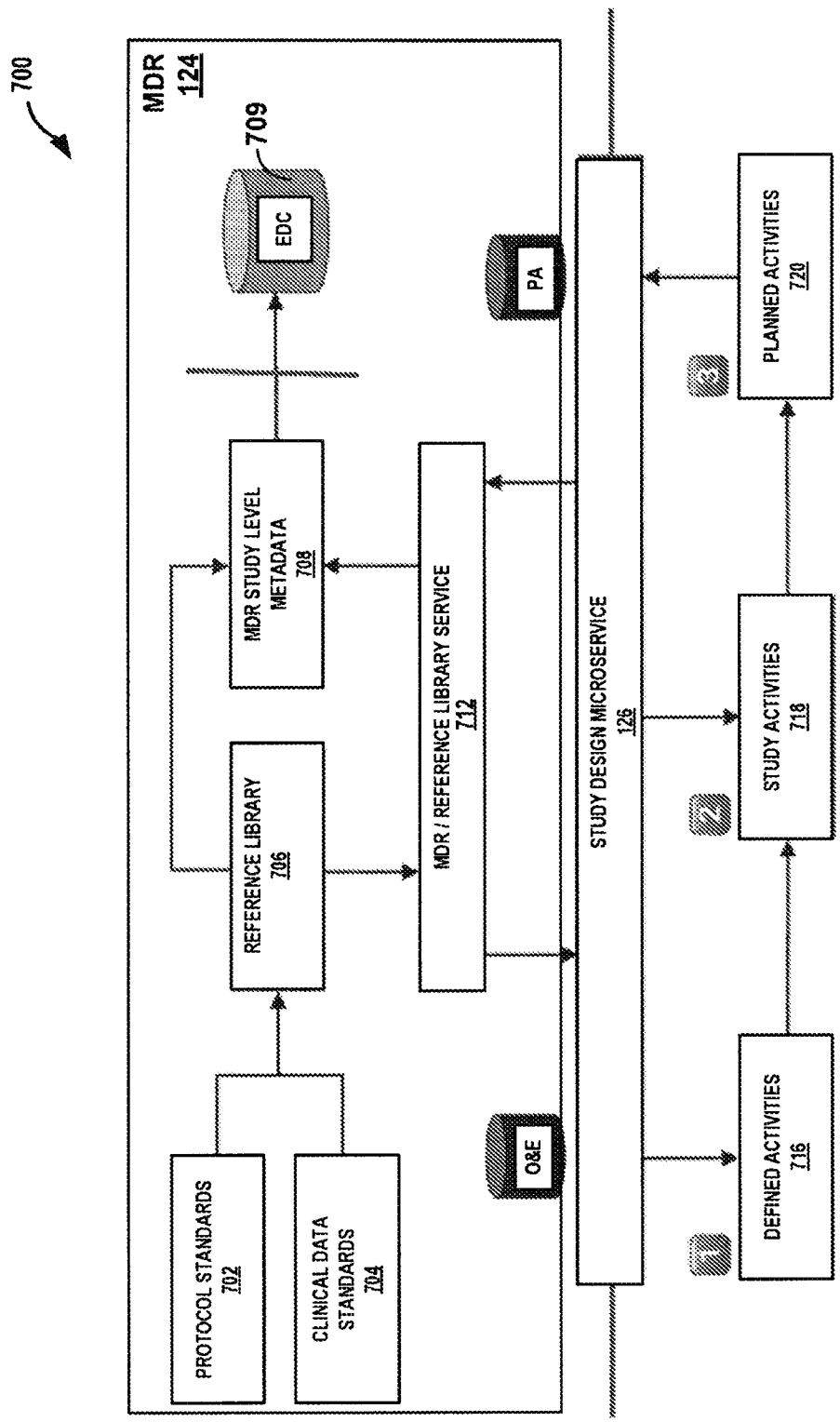
FIG. 8 is a block diagram illustrating interactions between the MDR and study design microservice of FIG. 1 in accordance with the techniques of the disclosure.

FIG. 8 is a block diagram illustrating interactions between MDR 124 and study design microservice 126 of FIG. 1 in accordance with the techniques of the disclosure. FIG. 8 may, in other words, illustrate a process by which study design microservice 126 uses protocol content and parameterized objective and endpoint templates to generate a schedule of study activities for the study.

As described above, MDR 124 may implement protocol standards 702 and clinical data standards 704 specified by regulatory authorities such as the CDISC trial summary and ClinicalTrials.gov specifications and/or as determined by enterprise-specific guidelines and processes. MDR 124 defines a data model and accompanying metadata in reference library 706 in accordance with protocol standards 702 and clinical data standards 704.

MDR reference library service 712 interfaces with study design microservice 126 to provide a schedule of study activities to a user. For example, study design microservice 126 may present, via UI framework 102, one or more defined study activities 716 in the study to the user. Defined Activities 716 present a preferred grouping of clinical data standards elements as they are to be used in definition of a schedule. Study design microservice 126 obtains the defined study activities from reference library 706 based on protocol standards 702 and clinical data standards 704. Defined study activities 716 may be mandatory, recommended, or optional. If a study activity is mandatory, the study activity is presented via UI framework 102 as selected and may not be unselected by the user. If a study activity is recommended, the study activity is presented via UI framework 102 as selected but may be unselected by the user. If a study activity is optional, the study activity is presented via UI framework 102 as unselected but may be selected by the user.

Study design microservice 126 may also inform the user on a selection of defined study activities based on protocol content, such as endpoints of the study. Study design microservice 126 stores the user selection as study activities 718. Study design microservice 126 brings in clinical data collection standards 704 for study activities. The user may review the list of study activities and may change default settings of study activities for a study schedule. Further, the user builds the study schedule of study activities by selecting study events via UI framework 102 so as to denote planned study activities 720 for the study schedule. Study design microservice 126 may write the study schedule to MDR 124 as MDR study-level metadata 708 which in turn can be used to generate Electronic Data Capture (EDC) system builds 709 to enable electronic capture of study execution data, along with other data descriptor formats that can be used to specify the non-EDC data to be collected for the study. Examples of non-EDC data include lab test results produced by central lab service providers and Electronic Health Records (EHR) patient data related to concomitant medications, demographic information and other topics and specified through the use of HL7 FHIR resource profiles. In some examples, such information is represented as an intermediate "clinical view" standard that aggregates all data sources (EDC and non-EDC) into a consolidated data structure that is then mapped to the SDTM tabulation standard currently mandated by the FDA as the format for all study submissions. In other examples, the study schedule may be populated in one or more specialized system microservices to facilitate generation of EDC, non-EDC and other study specification representations.

Figure 9:
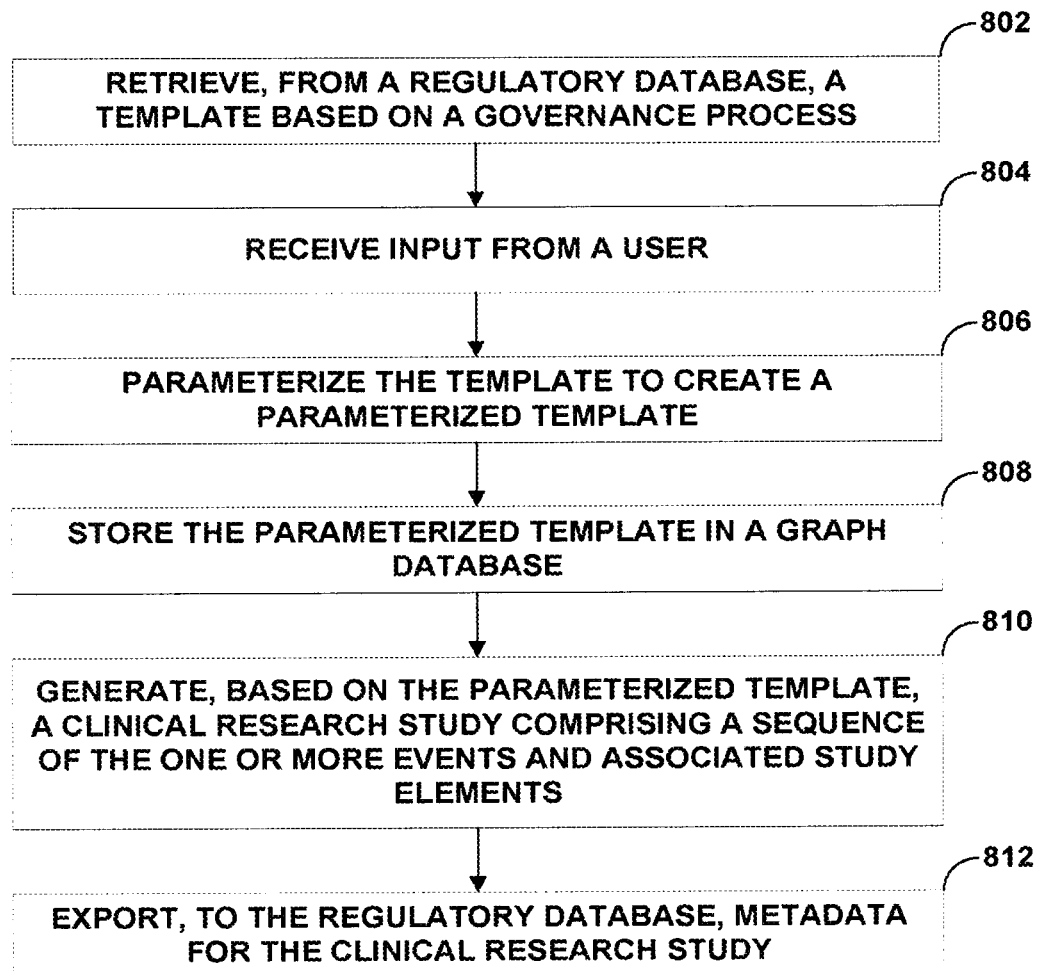
FIG. 9 is a flowchart illustrating an example operation for designing a clinical research study in accordance with the techniques of the disclosure.

FIG. 9 is a flowchart illustrating an example operation for designing a clinical research study in accordance with the techniques of the disclosure. Study design microservice 126 retrieves, from a regulatory compliant database such as MDR 124 of FIG. 1, one or more templates based on a governance process (802). The one or more templates based on a governance process may comprise, e.g., a clinical research study objective template and a clinical research study endpoint template.

Any combination of Study and Protocol Elements application 116, Schedule of Activities application 114, Protocol authoring application 118 and additional not-specified applications receive, via a user interface provided by UI framework 102, input from a user (804). Study design microservice 126 parameterizes the template based on the governance process with the user input to create a parameterized template (806). For example, study design microservice 126 may parameterize a clinical research study objective template to obtain one or more study objectives for a clinical research study. As another example, study design microservice 126 may parameterize a clinical research study endpoint template to obtain one or more study endpoints for a clinical research study.

In some examples, system applications incorporating UI framework 102 display, via the user interface, one or more input types and one or more values for each of the one or more input types. System applications incorporating UI framework 102 receive, from the user, a selection of a value of the one or more values for each of the one or more input types. The selection of values may specify, e.g., one or more values for one or more study protocol elements, one or more study design elements, or one or more study model elements. The user input may further specify one or more secondary or exploratory study objectives or one or more secondary or exploratory study endpoints.

Study design microservice 126 parameterizes the template based on the governance process with the selection of the value of the one or more values for each of the one or more input types to create the parameterized template. Study design microservice 126 stores the parameterized template in database 105 (808). In some examples, database 105 implements GraphQL queries and mutations to manage data. For example, study design microservice 126 implements GraphQL APIs that invoke database 105 as an efficient and flexible way to retrieve clinical development content.

Study design microservice 126 generates, based on the parameterized template, a clinical research study comprising a sequence of one or more study events specifying one or more study activities to be executed for the study event and associated study elements (810). In some examples, study design microservice 126 may optionally generate, based on the template, at least one study objective and at least one study endpoint that may be used to facilitate generation of the sequence of study events and key activities for the one or more study events. In some examples, study design microservice 126 defines a database for storing data collected for the clinical research study. System applications incorporating UI framework 102 may present, via a user interface, the clinical research study to a user. The user interface provided by UI framework 102 may be a dashboard web application.

In some examples, study design microservice 126 determines schedule optimizations, for example in terms of traceability of estimands/endpoints, cost estimates, or patient burden, for the one or more study activities to be executed for each study event of the one or more study events. Study design microservice 126 determines, based on the cost estimate for the one or more study activities to be executed for each study event of the one or more study events, a total cost estimate for the at least one study endpoint of the clinical research study. Schedule of Activities application 114 may present, via a user interface provided by UI framework 102, the cost estimate for the one or more study activities to be executed for each study event of the one or more study events and the total cost estimate for the at least one study endpoint.

In some examples, study design microservice 126 determines, based on the sequence of the one or more study events, a timeline for the clinical research study. The timeline may include a schedule for each of the one or more study activities to be executed for each study event of the one or more study events. Schedule of Activities application 114 may present, via a user interface provided by UI framework 102, the timeline for the clinical research study.

In some examples, study design microservice 126 exports, to MDR 124, metadata for the clinical research study (812). For example, study design microservice 126 retrieves, from database 105, a graph data structure representative of the clinical research study. Study design microservice 126 generates, from the graph data structure representative of the clinical research study, a tree data structure representative of the metadata for the clinical research study. Study design microservice 126 stores, in MDR 124, the tree data structure representative of the metadata for the clinical research study. In some examples, MDR 124 stores the metadata for the clinical research study in a predefined file format such as, e.g., an Extensible Markup Language (XML) file, a Portable Document Format (PDF) file, or a Microsoft Excel (XLS) file. In other examples, study design microservice 126 exports to one or more specialized system microservices the metadata for the clinical research study.

In some examples, study design microservice 126 generates, based on the parameterized template, one or more reporting criteria for the clinical research study. UI framework 102 may produce, within its dashboard capability, the results of one or more reporting criteria for the clinical research study.

Figure 10:
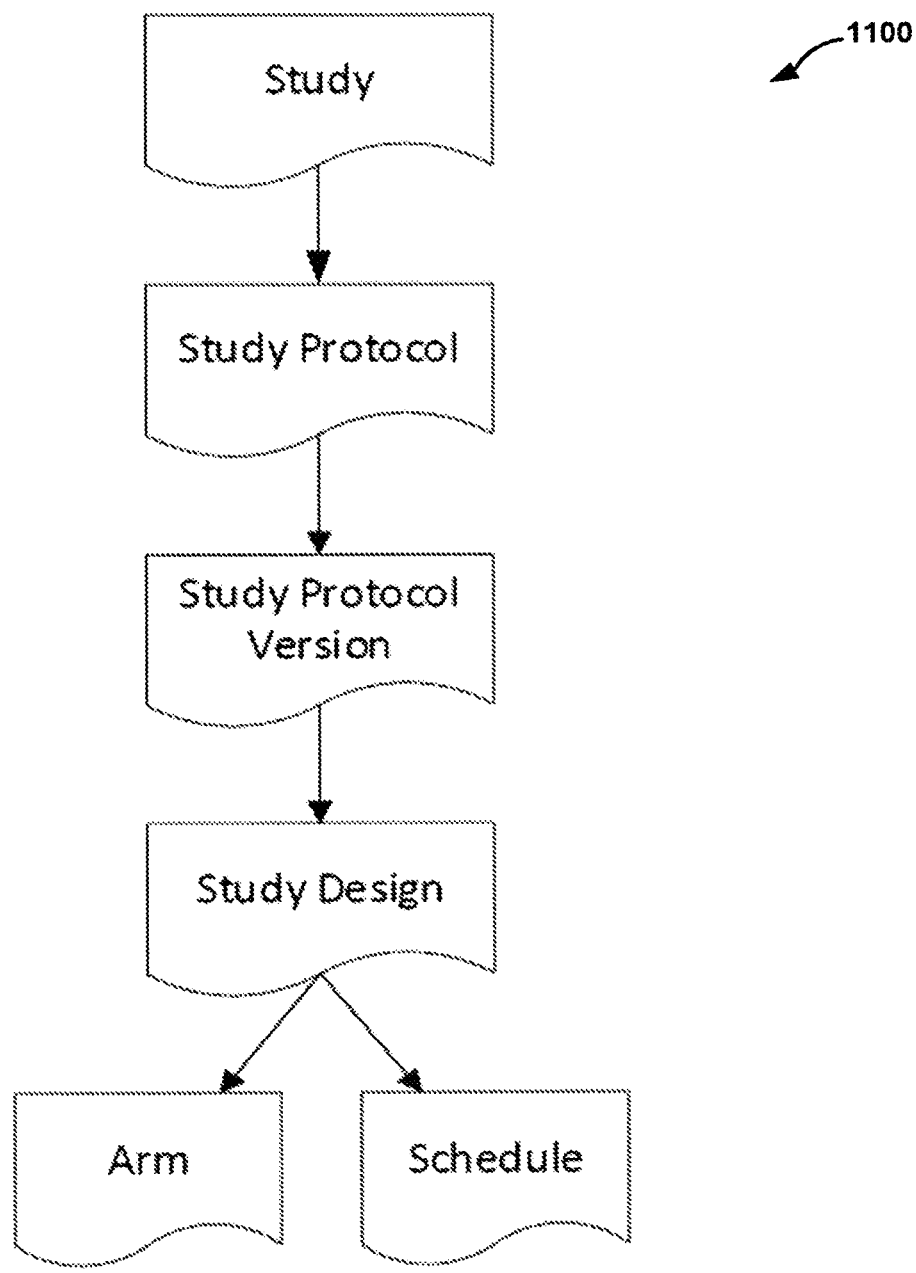
FIGS. 10-15 are block diagrams illustrating a clinical research study organized into a tree data structure in accordance with the techniques of the disclosure.

FIGS. 10-15 are block diagrams illustrating a clinical research study organized into a tree data structure in accordance with the techniques of the disclosure. FIG. 10 depicts an initial state of tree data structure 1100. The tree data structure comprises a clinical research study as a root node. A study protocol is a child node of the clinical research study. A study protocol version is a child node of the study protocol. A study design is a child node of the study protocol version. The study design comprises two child nodes, a study arm and a study schedule.

To copy an object, most techniques may be considered to be either a "shallow" copy or a "deep" copy. To perform a shallow copy, one creates a new object, and copies data of the to-be-copied object to the new object. Furthermore, references of to-be-copied object are copied to the new object such that the new object contains references and/or pointers to the same objects as the to-be-copied object. For example, where the to-be-copied object is a node in a tree and comprises a reference to a child node, the new object is configured with a reference pointer that points to the same child node to which a reference pointer of the to-be-copied node points. Therefore, objects referenced by the to-be-copied object are shared by the new object, so if a referenced object is modified, the change is visible by both the to-be-copied object and the new object. Shallow copies are typically fast and computationally cheap to perform. However, shallow copies have the drawback that referenced objects are not distinct between the to-be-copied object and the new object.

An alternative to the shallow copy is the deep copy. To perform a deep copy, any references of the to-be-copied object are dereferenced such that, rather than copying references to objects from the to-be-copied object to the new object, a deep copy creates new copy objects are created for any referenced objects, and places references to these new copy objects placed in the new object that is a copy of the to-be-copied object. For example, where the to-be-copied object is a node in a tree and comprises a reference to a child node, a new child node and a new object are created, the data of the to-be-copied node is copied to the new node, the data of the child node is copied to the new child node, and the new object is configured with a reference pointer to the new child node. Thus, the deep copy is different from a shallow copy in that the objects referenced by the copy are distinct and independent from the objects referenced by the original. Changes made to the child node of the to-be-copied node are different and distinct from the changes made to the new child node of the new node. Deep copies are typically more computationally expensive because additional objects are created for each object referenced by the to-be-copied node. Further, deep copies may sometimes be substantially more complicated where the references form a complicated graph.

As described herein, the techniques of the disclosure store a clinical research study as a tree data structure in a database. Further, the techniques of the disclosure implement a form of lazy copy to make updates to the tree data structure. The lazy copy algorithm is described in additional detail below. A lazy copy is an implementation of a deep copy. When initially copying an object, a shallow copy is made between the to-be-copied node and the new node. When an object is modified (e.g., one of the to-be-copied node, the new node, or a child of the to-be-copied node), a deep copy is made to maintain independence between the to-be-copied node and the new node. This allows one to take advantage of the speed of a shallow copy where a deep copy is not immediately needed, and defer the computational expense of the deep copy until the deep copy is necessary.

Figure 11:
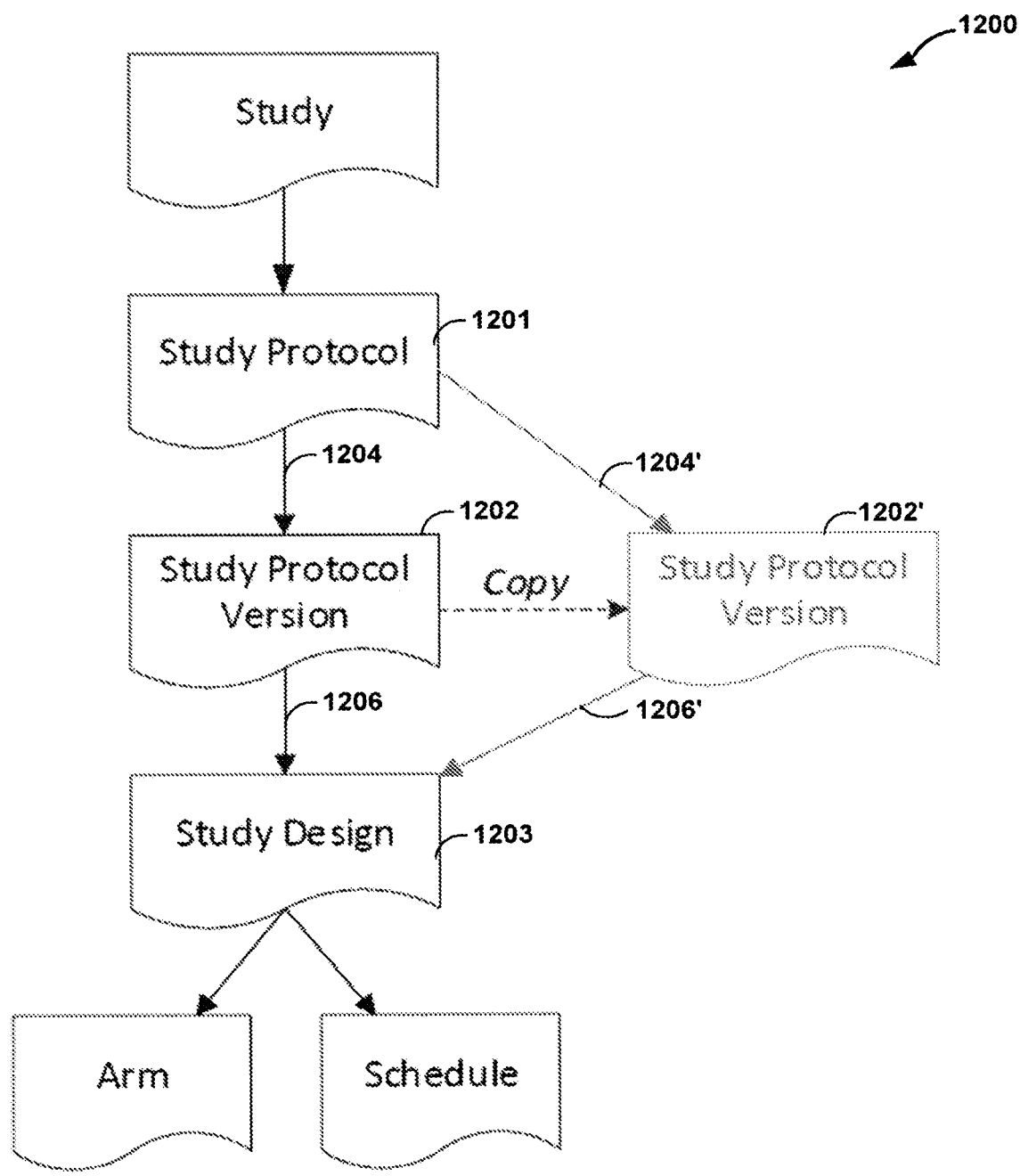

In some examples, tree graph 1200 shown in the example of FIG. 11 may be retrieved from a storage medium. One or more updates, changes, deletions, or additions may be made to tree graph 1200, a node of tree graph 1200, or data represented by a node of tree graph 1200, and the updated tree data structure 1200 may be stored in the storage medium. As described herein, a node of tree graph 1200 may comprise, e.g., data for one of a study, a study protocol, a study protocol version, a study design, or a study schedule of the data model stored by MDR 124 of FIG. 1.

FIG. 11 is a block diagram illustrating an operation for performing a lazy copy of node 1202 of tree data structure 1200 to obtain duplicate node 1202'. In some examples, tree data structure 1100 of FIG. 10 is modified from an initial state to obtain tree data structure 1200 as described subsequently. As depicted in FIG. 11, node 1202, which comprises data for a study protocol version, is copied to duplicate node 1202'. Further, inbound edge 1204 and outbound edge 1206 of node 1202 are duplicated to node 1202' such that node inbound edge 1204' and outbound edge 1206' point to duplicate node 1202'.

Figure 12:
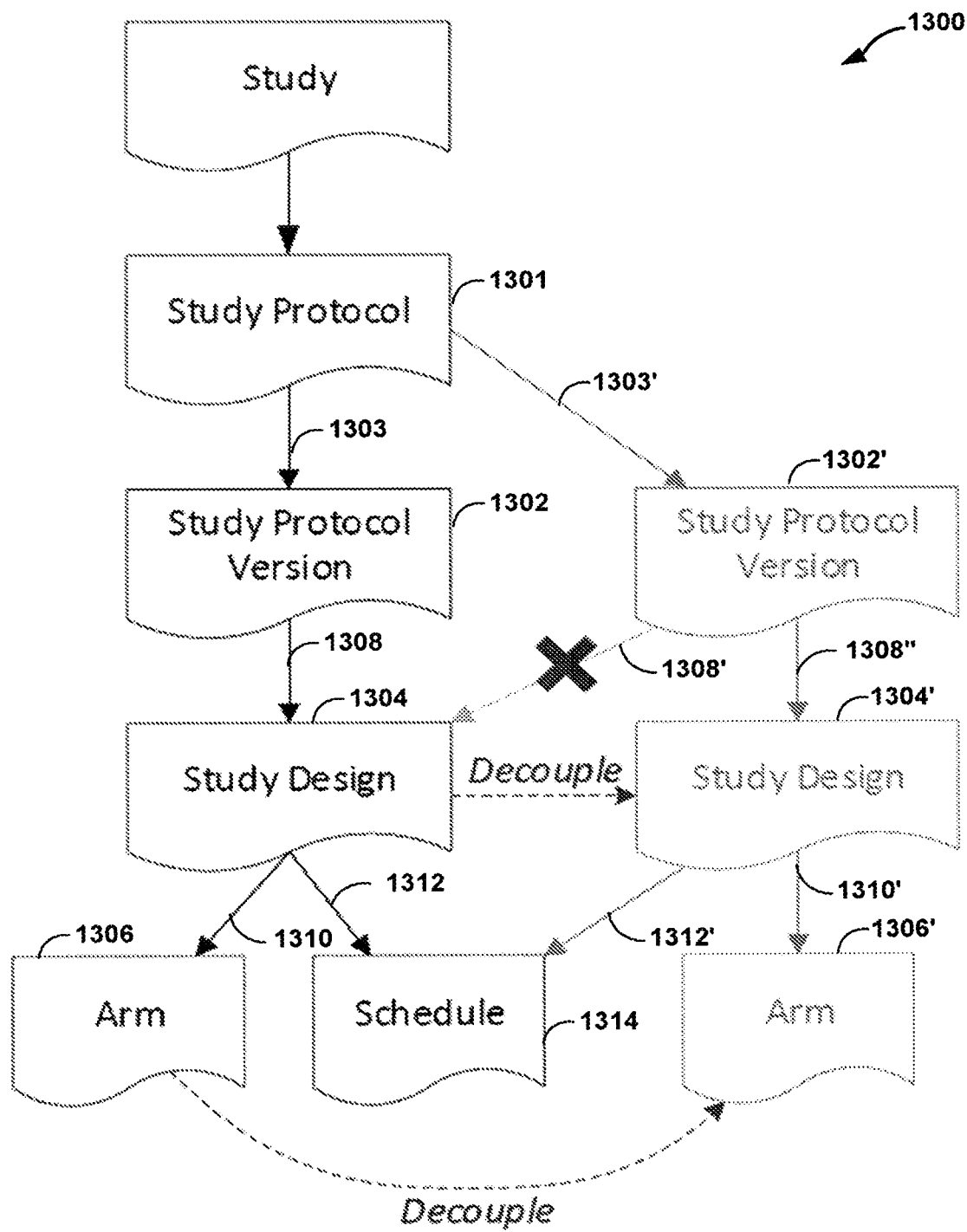

FIG. 12 is a block diagram illustrating an operation for updating node 1306 of tree data structure 1300, where an ancestor of node 1306 is a lazy copy of another node. In some examples, tree data structure 1200 of FIG. 10 is modified from an initial state to obtain tree data structure 1300 as described subsequently.

As depicted in FIG. 12, an update is to be made to node 1306, which includes data for a study arm. The algorithm of FIG. 12 walks up the stack of tree data structure 1300 to determine if the updated node 1306, or any ancestor of node 1306, has more than one owner. If so, then a branch including node 1306 includes a lazy copy. In the example of FIG. 12, node 1302' is a lazy copy of node 1302.

If the algorithm determines that node 1306 and each ancestor of node 1306 includes only a single owner (e.g., parent), then the update is performed in place and the algorithm completes. If the algorithm determines that node 1306 or an ancestor of node 1306 has multiple owners, then the algorithm duplicates node 1306 and all parents between node 1306 and the ancestor node with multiple owners. The algorithm duplicates inbound and outbound edges to point at new documents, and duplicates outbound edges pointing at new nodes.

For example, with respect to FIG. 12, node 1306 is duplicated as node 1306' and node 1304 is duplicated as node 1304'. Edge 1308' pointing at node 1304 is duplicated as edge 1308" to point at node 1304' and edge 1308' is deleted. Edge 1310 pointing at node 1306 is duplicated as edge 1310' to point at node 1306'. Edge 1312 pointing at node 1314 is duplicated as edge 1312' to point at node 1314.

As another example, first node 1302 comprises inbound edge 1302 to parent node 1301 and outbound edge 1308 to child node 1304. First node 1303 of tree data structure 1300 is duplicated to create second node 1302' as described above. Inbound edge 1303' of duplicate node 1302' is created to parent node 1301 and outbound edge 1308' of duplicate node 1302' is created to child node 1304. An update is made to child node 1304. In response to determining that child node 1304 has multiple parents (e.g., nodes 1302 and 1302'), child node 1304 is duplicated to create a duplicate child node 1304'. Outbound edge 1308" of duplicate node 1302' is created to duplicate child 1304'. Outbound edge 1308' of duplicate node 1302' to child 1308 is deleted, and the update is performed to the at least one child node. This process may be performed to duplicate each child and descendent of duplicate node 1302'.

Figure 13:
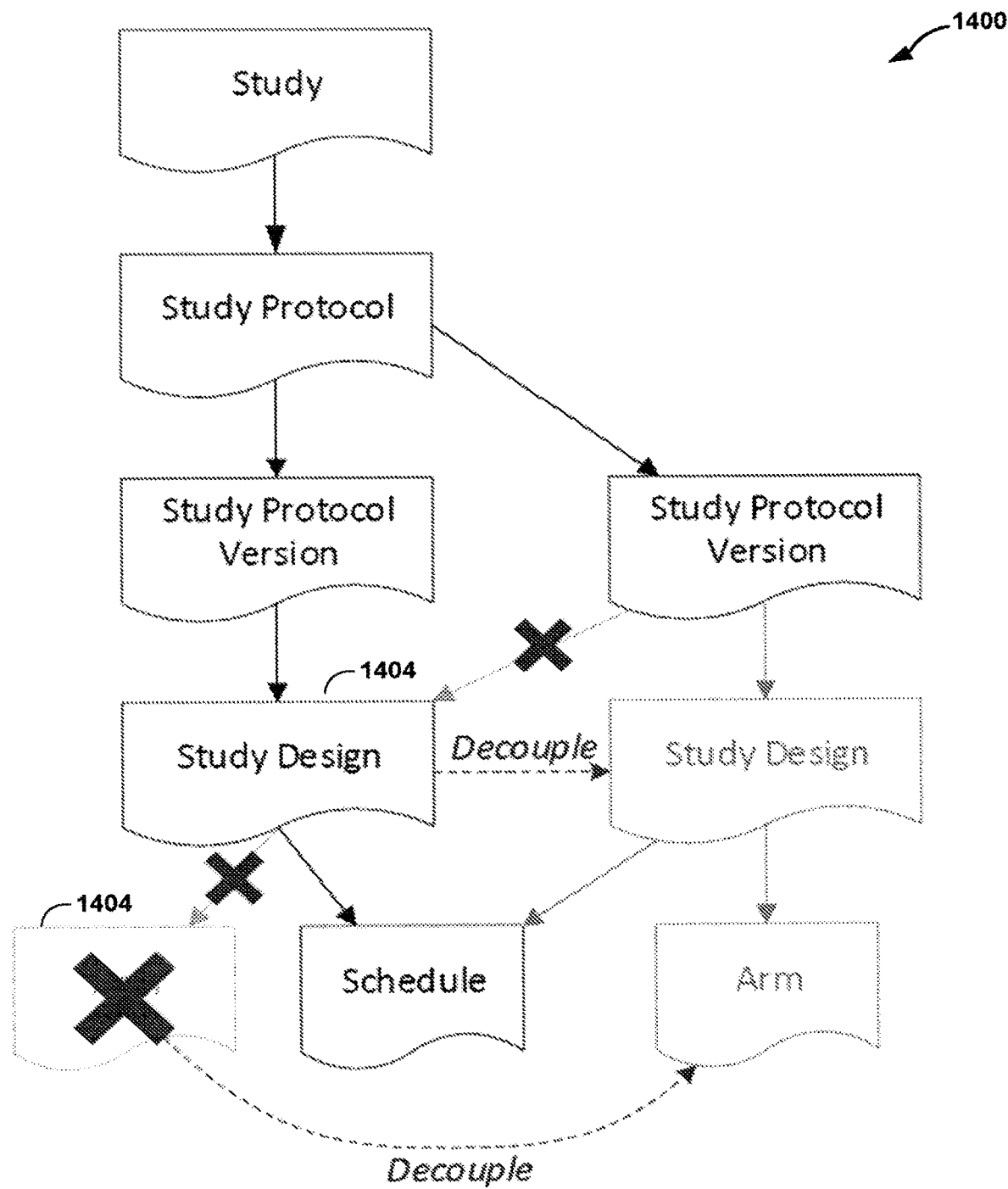
Figure 14:
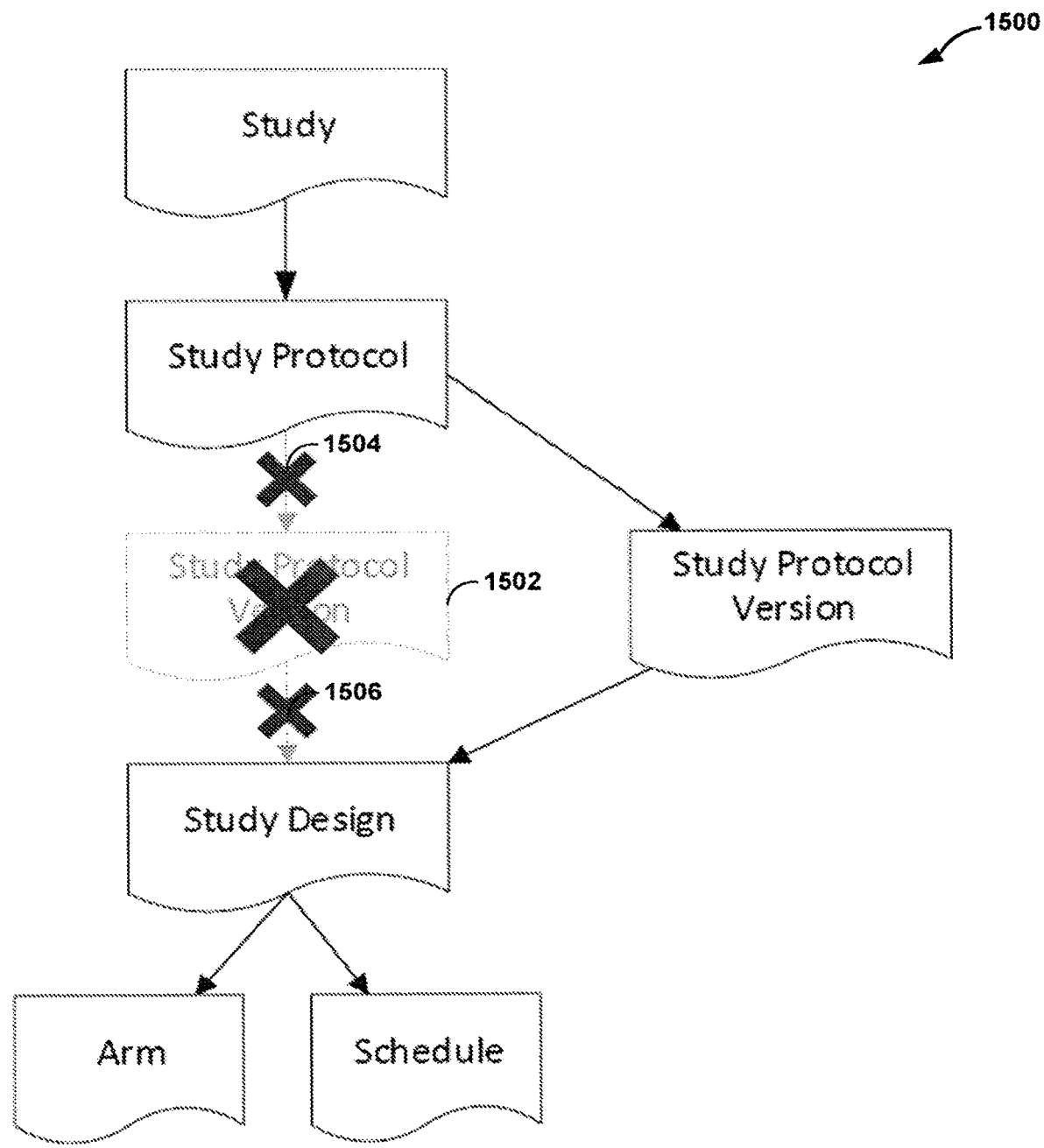
Figure 15:
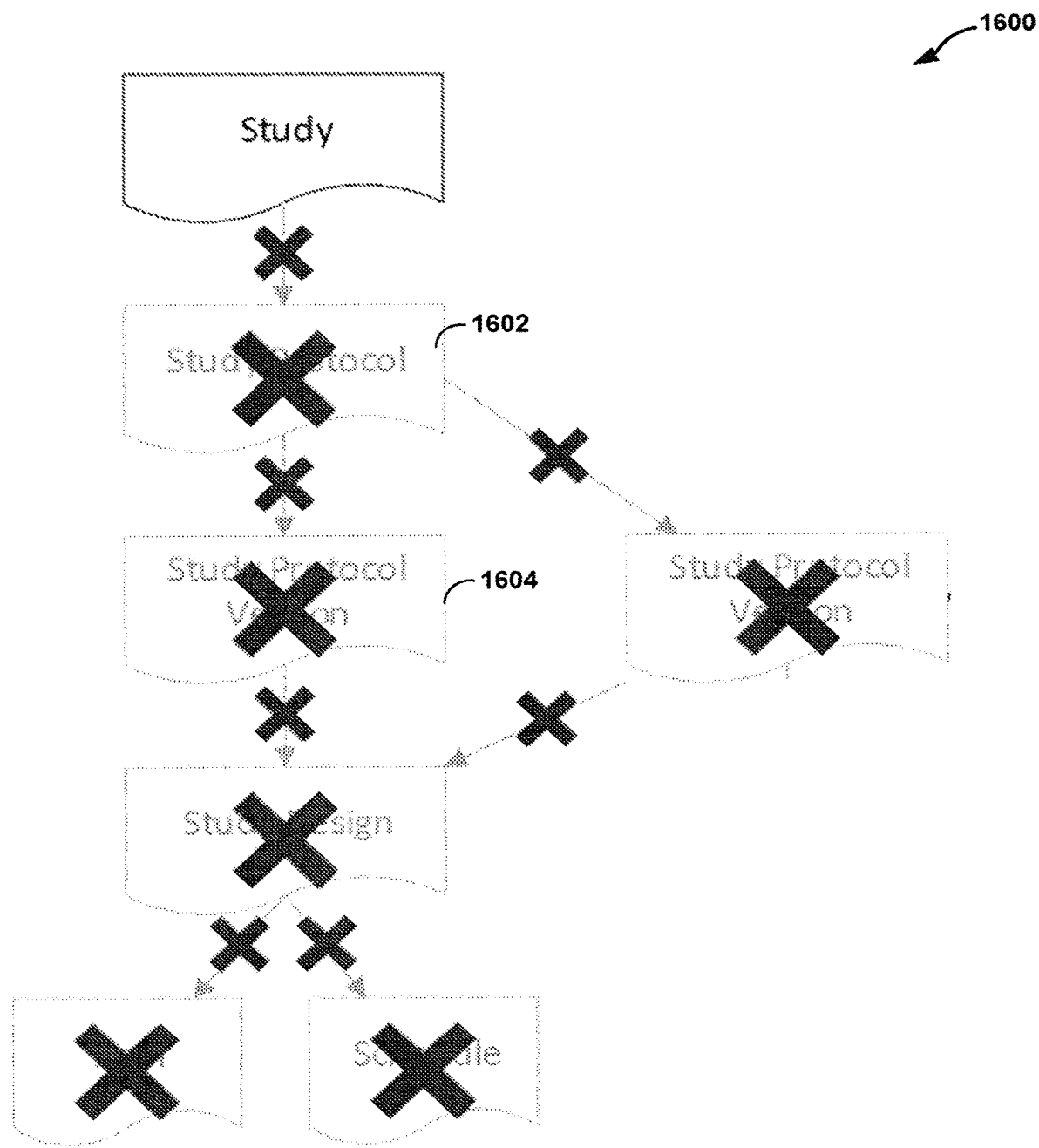

FIGS. 13-15—depict illustrating various use cases for deleting nodes where the node, an ancestor of the node, or a descendent of the node is a lazy copy. FIG. 13 is a block diagram illustrating an operation for deleting node 1404, wherein parent node 1402 is a lazy copy. In some examples, tree data structure 1200 of FIG. 11 is modified from an initial state to obtain tree data structure 1400 as described subsequently.

As depicted in FIG. 13, node 1404 is to be deleted. The algorithm determines whether node 1404 or an ancestor of node 1404 is a lazy copy as described above with respect to FIG. 13. If an ancestor of node 1404 is a lazy copy, the algorithm walks up the stack of tree data structure 1400 to find the top lazy copy (e.g., node 1404). Starting at the top lazy copy (e.g., node 1404), the algorithm decouples documents down the stack by performing deep copies of each descendent of the top lazy copy. The algorithm then deletes node 1404 and all dependent nodes.

Figure 16:
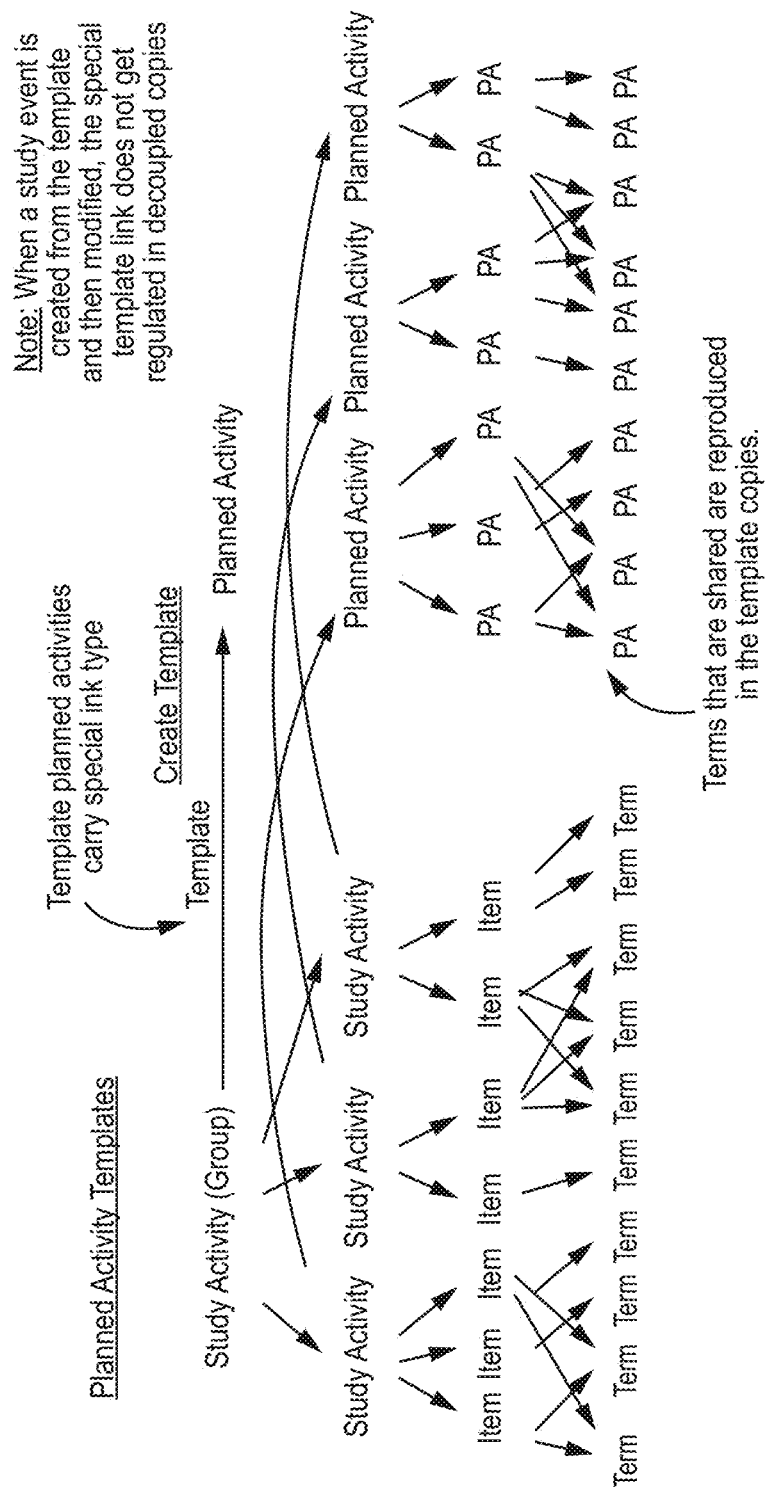
FIG. 16 is a graph illustrating a lazy copy of a planned study activity template for a clinical research study in accordance with the techniques set forth herein.

FIG. 14 is a block diagram illustrating an operation for deleting node 1502, wherein node 1502 is a lazy copy. In some examples, tree data structure 1200 of FIG. 16 is modified from an initial state to obtain tree data structure 1500 as described subsequently.

As depicted in FIG. 14, node 1502 is to be deleted. The algorithm determines whether node 1502 or an ancestor of node 1502 is a lazy copy as described above with respect to FIG. 13. Upon determining that node 1502 is a lazy copy but has no ancestors that are lazy copies, the algorithm deletes node 1502 and deletes inbound edge 1504 and outbound edge 1506 pointing to and from node 1502.

FIG. 15 is a block diagram illustrating an operation for deleting node 1602, wherein child node 1604 is a lazy copy. In some examples, tree data structure 1200 of FIG. 11 is modified from an initial state to obtain tree data structure 1600 as described subsequently.

As depicted in FIG. 15, node 1602 is to be deleted. The algorithm walks tree data structure 1600 to identify descendent nodes of node 1602. For each owned node of node 1602, the algorithm checks to see if any nodes outside the set of owned nodes also declares ownership to the node (e.g., the node has multiple parents). If so, each owned nodes with multiple parents is duplicated to as to decouple the multiple parent nodes from one another and permit deletion of the owned node.

As an example of the foregoing, the algorithm may determine that the first node has multiple parent nodes, wherein the first node comprises multiple inbound edges to the multiple parent nodes of the first node and at least one outbound edge to at least one child node of the first node. In response to determining that the first node has multiple parent nodes, the algorithm determines a closest superior ancestor node of the first node that has only a single parent node. The algorithm duplicates the superior ancestor node of the first node to create a duplicate superior ancestor node. The algorithm duplicates a branch descending from the superior ancestor node of the first node to create a duplicate branch descending from the duplicate superior ancestor node, wherein the duplicate branch descending from the duplicate superior ancestor node duplicates nodes and edges of the branch descending from the superior ancestor node of the first node. The algorithm deletes the first node and any inferior descendent nodes of the first node.

As another example, the algorithm determines that the first node comprises at least one outbound edge to at least one child node of the first node, wherein the first node comprises an inbound edge to a parent node of the first node. The algorithm determines, based on inbound edges of the at least one child node to the first node and to a second node, that the at least one child node has multiple parent nodes. The algorithm deletes the first node, an outbound edge of the parent node to the first node, and the inbound edges of the at least one child node to the first node.

FIG. 16 is a graph illustrating a lazy copy of a planned study activity template for a clinical research study in accordance with the techniques set forth herein. A template for a planned study activity may be created from a study activity group as a lazy copy. The template of planned study activities carries a special link type. When a study event is created from the template and then modified, the special template link does not get replicated in decoupled copies. Terms that are shared are reproduced in the template as lazy copies.

Figure 17:
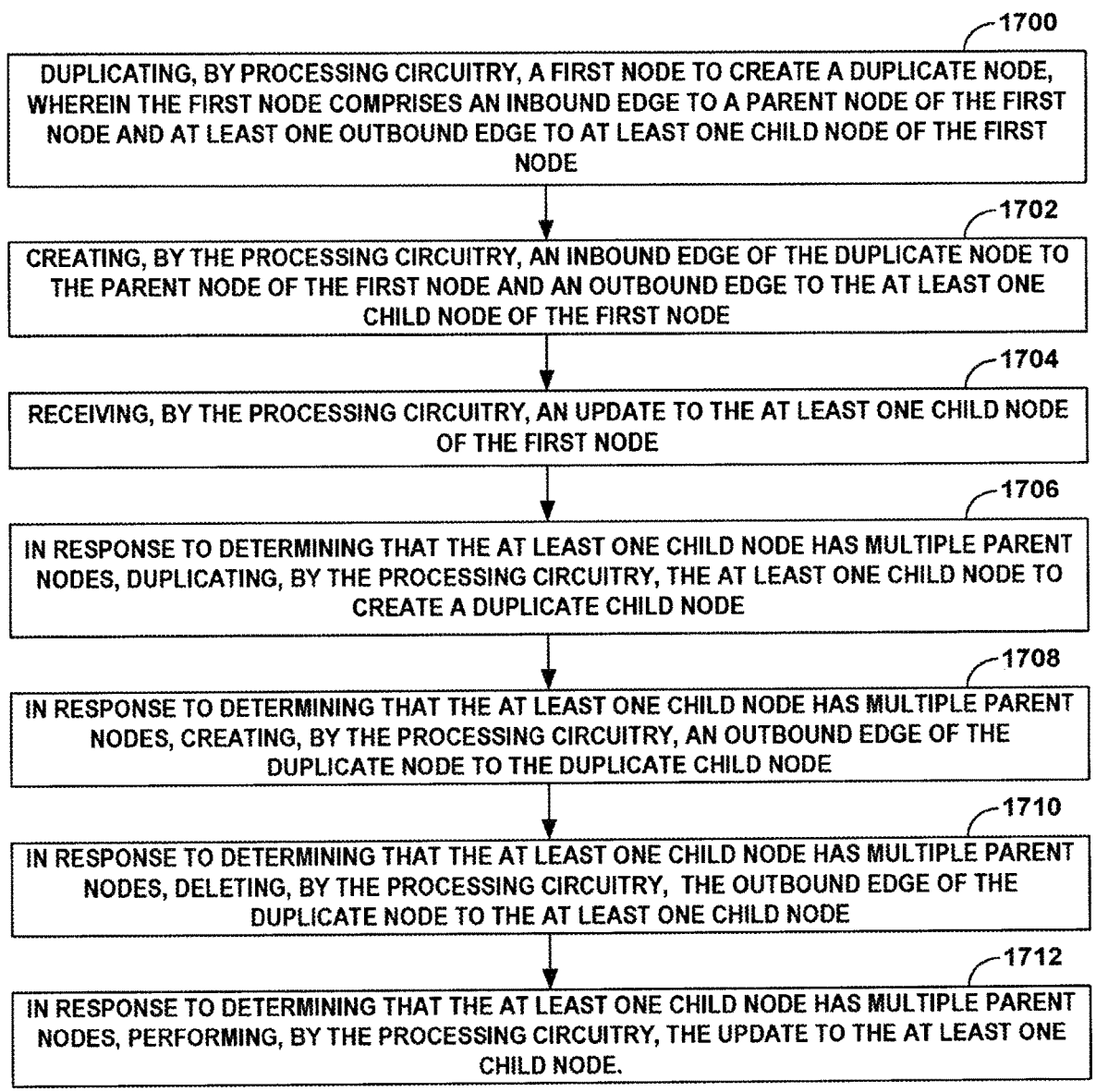
FIG. 17 is a flowchart illustrating an example operation for executing a lazy copy.

FIG. 17 is a flowchart illustrating example operation of the study design microservice in performing a lazy copy in accordance with various aspects of the techniques described herein. Study design microservice 126 (FIG. 1) may first duplicate a first node, e.g., 1202, to create a duplicate node, e.g., 1202' (as shown in the example of FIG. 11), which comprises an inbound edge 1204 and at least one outbound edge 1206 to at least one child node, e.g., node 1203, of first node 1202 (1700). As described above, study design microservice 126 may create an inbound edge 1204' of duplicate node 1202' and an outbound edge 1206' to at least one child node 1203 of first node 1202 (1702).

Study design microservice 126 may then receive an update to at least one child node 1203 of first node 1202 (1704), whereupon study design microservice 126 may, in response to determining that child node 1203 has multiple parent nodes, duplicate child node 1203 to create a duplicate child node 1304' (FIG. 12) (1706). In response to determining that child node 1203 has multiple parent nodes (e.g., nodes 1302 and 1302'), study design microservice 126 may create an outbound edge 1308' to duplicate child node 1304' (1708). Moreover, in response to determining that child node 1203 has multiple parent nodes 1302 and 1302', study design microservice 126 may delete outbound edge 1308' of duplicate node 1302' to child node 1308 (1710). Study design microservice 126 may next, in response to determining that child node 1203 has multiple parent nodes 1302 and 1302', perform the update to child node 1302' and/or each child and descendant of duplicate node 1302' (1712).

Figure 18:
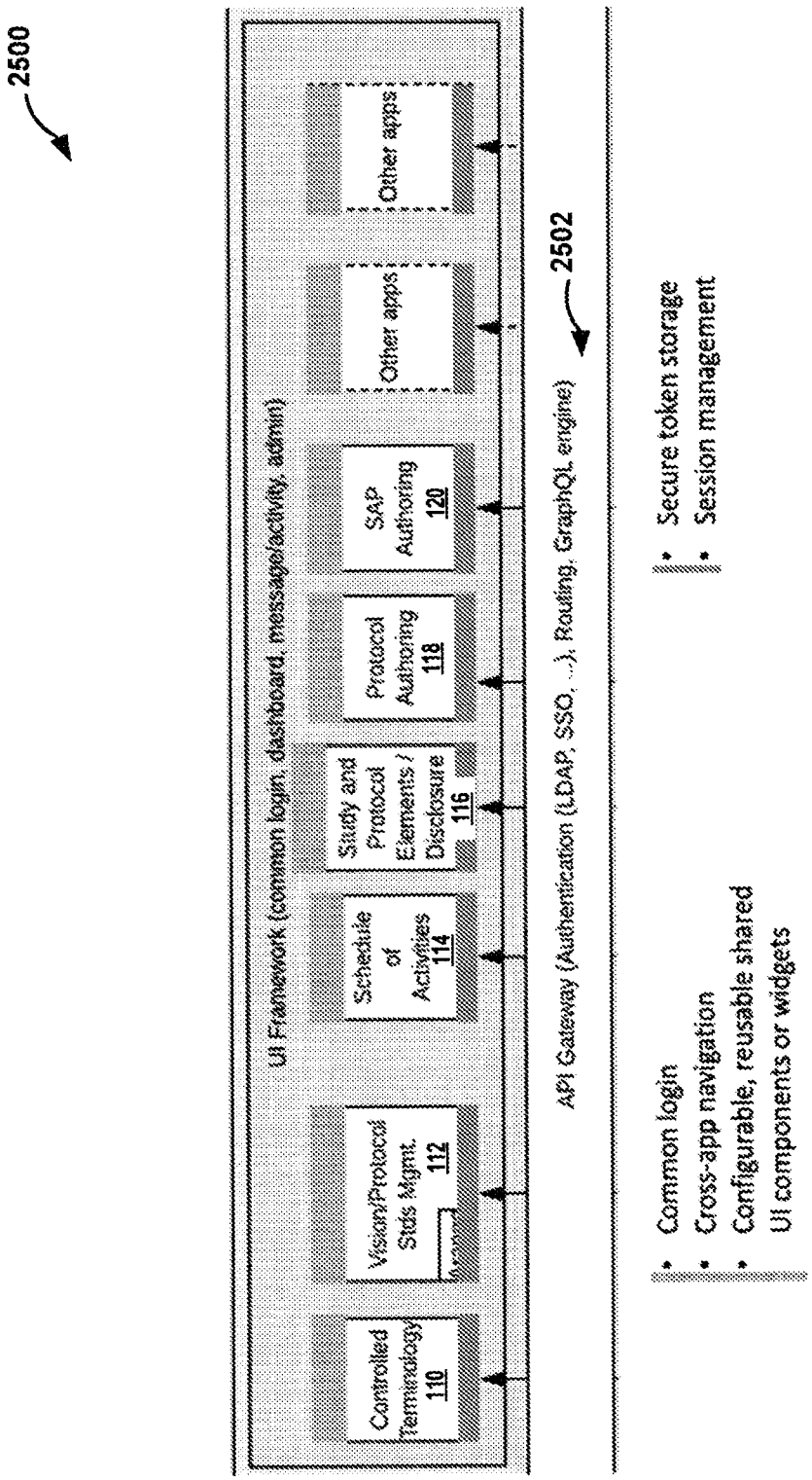
FIG. 18 is a block diagram illustrating an example user interface (UI) framework for generating clinical research studies in accordance with the techniques of the disclosure.

FIG. 18 is a block diagram illustrating example UI framework 2500 for generating clinical research studies in accordance with the techniques of the disclosure. UI Framework 2500 may operate in a substantially similar fashion to UI framework 102 of FIG. 1. UI Framework 2500 implements a plurality of applications, including controlled terminology 110, vision/protocol standards management 112, schedule of study activities 114, Study and Protocol Elements/disclosure application 116, protocol authoring 118, and SAP authoring 120. In some examples, UI Framework 2500 may further be configured to implement other applications not expressly described herein. Each application comprises an API interface for interfacing with API gateway 2502. UI Framework 2500 provides a common login, cross-application navigation, configurable, reusable, shared UI components or widgets, secure token storage, and session management services to a user.

Figure 19:
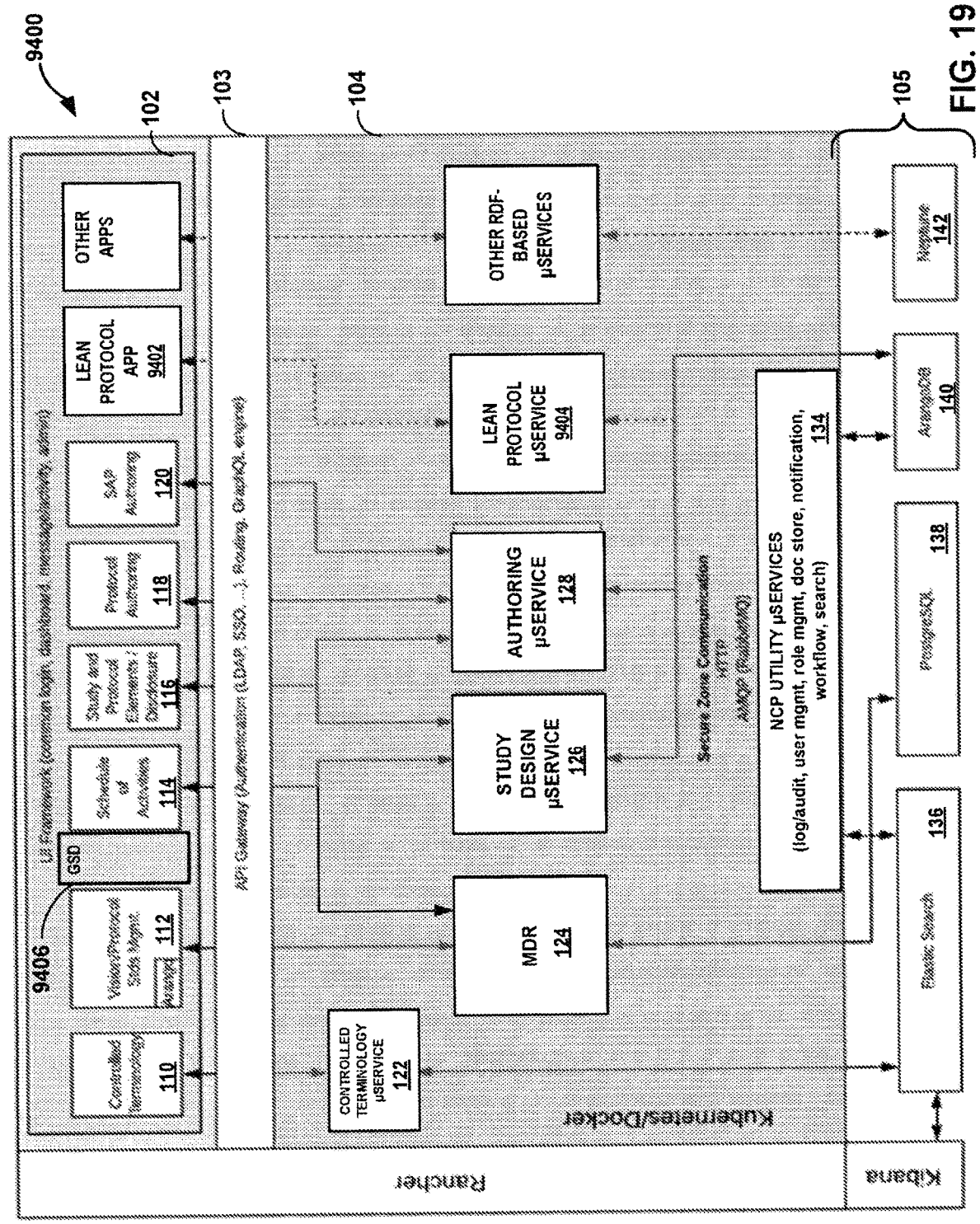
FIG. 19 is a block diagram illustrating example system 9400 for generating a digitized framework for clinical development using a lean protocol dashboard in accordance with the techniques of the disclosure.
Figure 21:
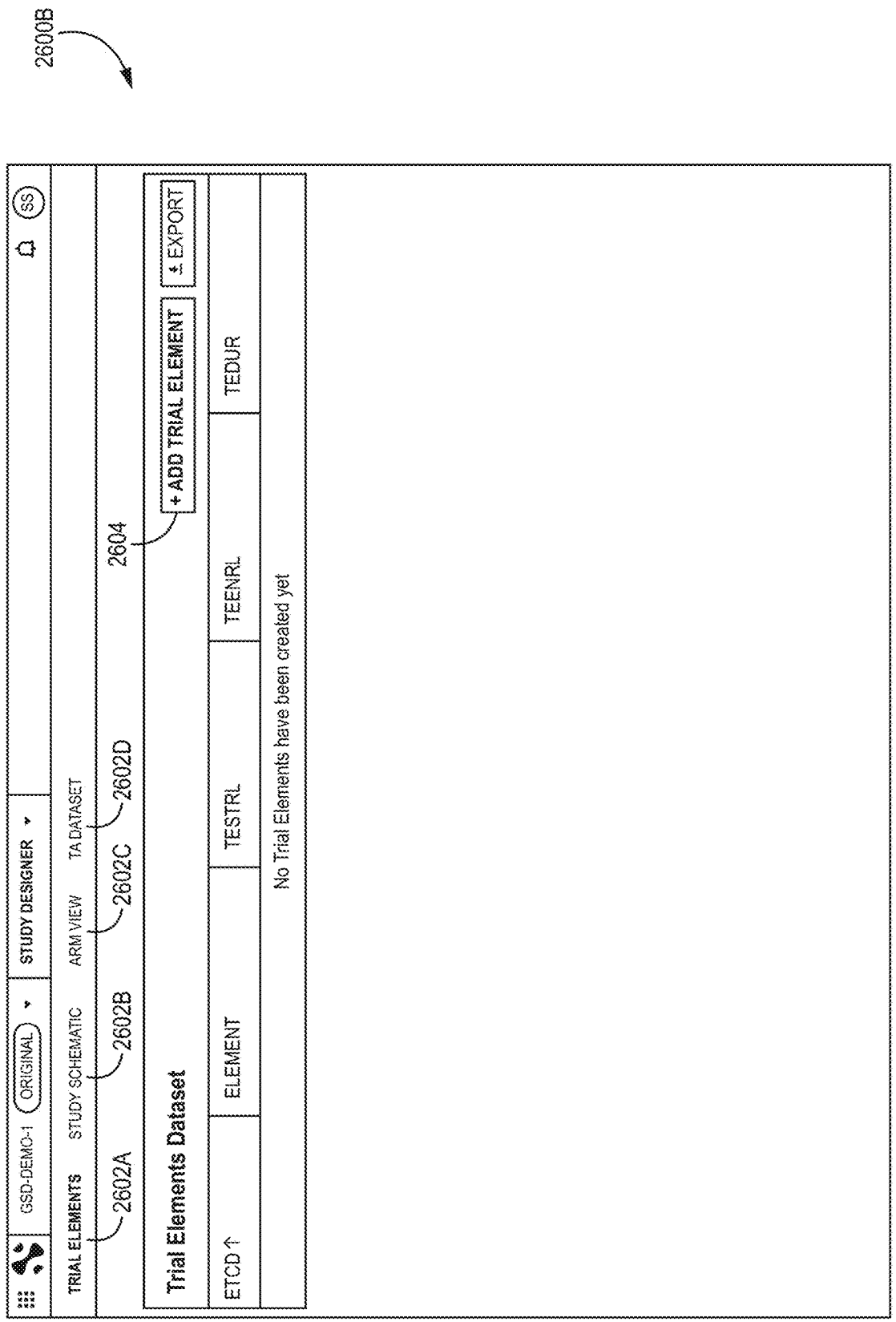
Figure 23:
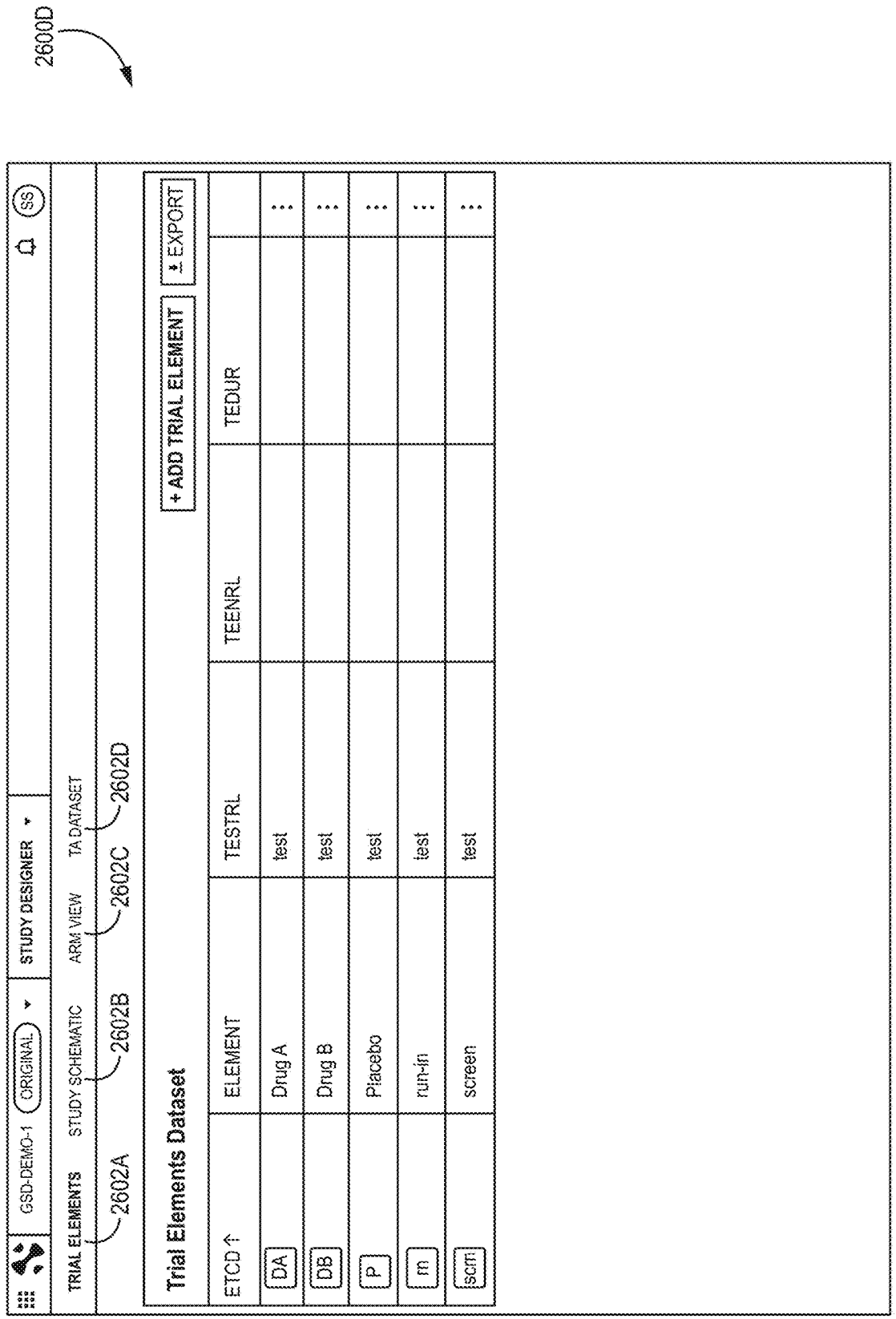
Figure 24:
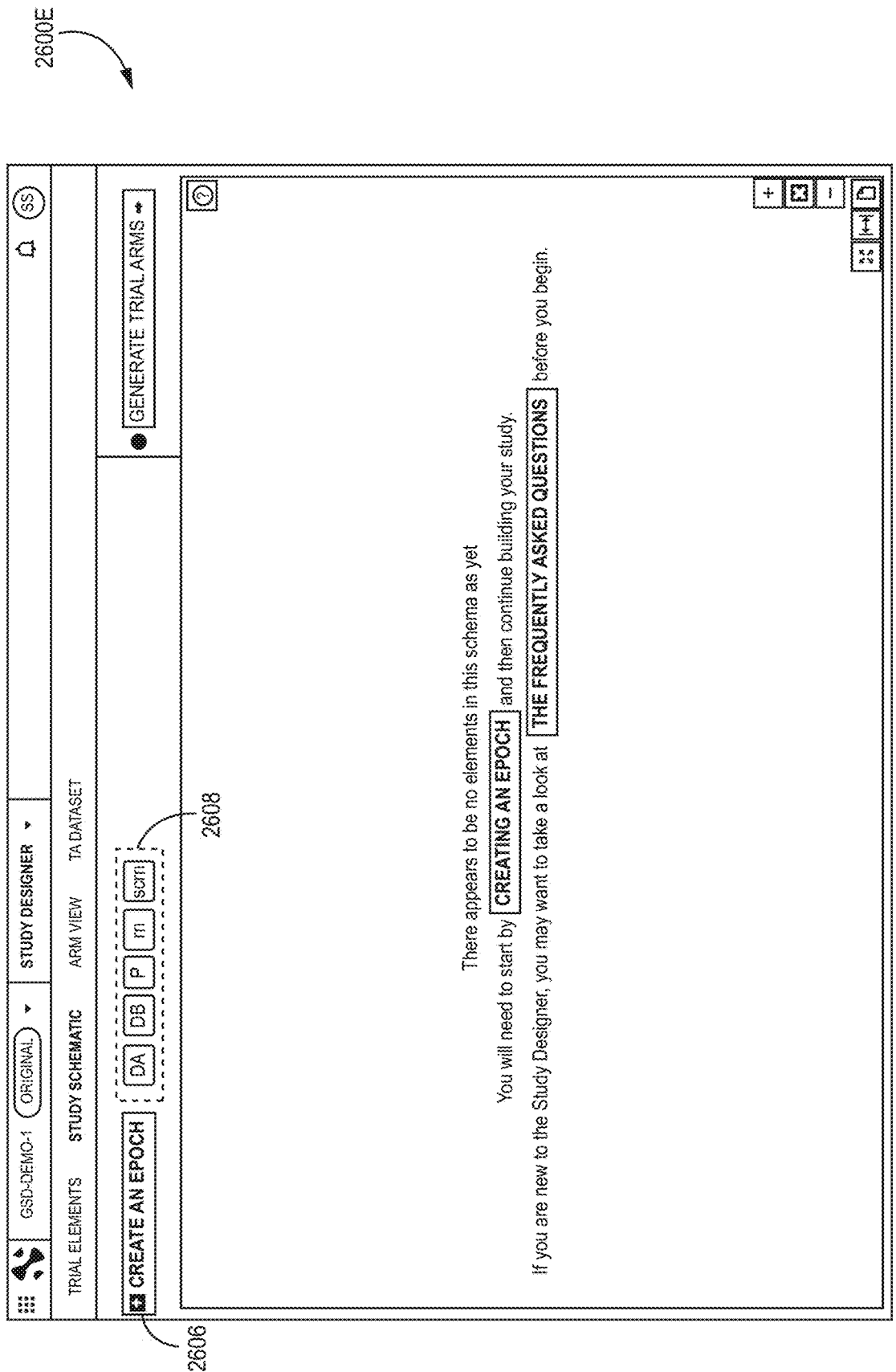

FIG. 19 is a block diagram illustrating example system 9400 for generating a digitized framework for clinical development using a lean protocol dashboard in accordance with the techniques of the disclosure. System 9400 may operate in a substantially similar fashion as system 100 of FIG. 1. In addition, as described herein, Schedule of Activities application 114, Study and Protocol Elements application 116, and Protocol Authoring application 118 (executed against Study Design microservice 126) may accommodate graphical user interface (GUI) study designer ("GSD") 9406 (which exists as a separate graphical user interface application that complements one or more of associated applications 114-118 as well as possibly additional apps that are not shown in the example of FIG. 19) that enables graphical design of a study protocol as described herein. When GUI study designer 9406 is present, certain operations of associated applications may be rendered as read-only; in other words, these operations are supplanted by the more advanced graphical design capabilities of GUI study designer 9406 thereby improving the overall ease of use of system 100 for the end user.

Further, system 9400 includes Lean Protocol application 9402 and Lean Protocol microservice 9404 that implement the functions of the lean protocol system for presenting a clinical study protocol as a sequence of a plurality of stages described herein. A stage specifies a logical grouping of study development tasks and may comprise multiple concurrently-executable processes (also referred to herein as "swimlanes"), as described below, with the intent that these study development tasks are enabled earlier in the study development process than would be otherwise possible via the appropriate grouping and locking of the necessary prerequisite study protocol content sufficient to enable those actions. In other words, the Lean Protocol application is a formalization or instantiation of the principle that Clinical Study design can be made more efficient by decomposing what is currently treated as a monolithic set of work into multiple concurrently executed "gates," each of which frees up specialized processes/tasks that are necessary for study execution to begin.

Gates may optionally be grouped into phases, which may be logical in nature and serve to represent relative timing from inception of the clinical study design work. Gates may address specific topics (e.g., feasibility and recruitment) that in turn may be present in multiple phases with each phase representing a potential refinement of design content informed by the results of gate-enabled prior phase activity.

In one example, for a simple study design (e.g., Phase I safety trial) these gates may be fully independent of each other and grouped under a single stage. In another example, for a more complex study design (e.g., Phase III efficacy trial) gates may be assembled into multiple stage groupings, where each stage progressively refines the study protocol content from earlier stages and as a result enables the study development tasks associated with gates of those stages to also be further refined.

Lean Protocol conceptually sits above all other Study development application functionality of system 9400 of FIG. 19 (including Graphical Study Designer application 9406, Schedule of Activities application 114, and other apps not expressly described herein). Each such application may produce one or more "conditions" that feed into "gates;" these gates in turn free up downstream processes/tasks once approved. In one example, these conditions are based on the locking of Study sections as previously disclosed. FIGS. 20-30 are illustrations of a graphical user interface (GUI) clinical study protocol designer in accordance with the techniques of the disclosure. The GUI clinical study protocol designer (also referred to herein as "Graphical Study Designer") 9406 allows a study design practitioner to graphically model the conceptual structure of a Study Protocol in an intuitive manner and as a result of that modeling, automatically generate the Arms necessary to execute that Study Protocol. The extended functionality provided by graphical study designer 9406 improves user efficiency and accuracy in the early stages of Study Design. Each Arm represents a path through which a Study Subject can proceed within the context of the Study.

For example, in a double-blinded Study where a drug candidate is evaluated against a placebo with neither the medical practitioner nor the subject being aware of which substance the subject is being given, two Arms are necessary, one for the placebo path and one for the active drug path, with a randomization rule distributing the subjects within the study between the two Arms. Study Protocols may become much more complex than this, and one of the potential challenges for a Study Designer is to accurately decompose a complex Protocol's design into the correct set of Arms that represent the full set of valid Study Protocol paths through which a subject can proceed. The Graphical Study Designer application and supporting microservice eliminates the potential for an inaccurate representation of these Arms and the resulting delays in Study Protocol finalization that would ensue from such an error. In this manner, Graphical Study Designer 9406 provides a more capable alternative means of modeling Study Protocol Arms than the tabular capability previously disclosed as part of the Study Protocol Elements application.

In addition, Graphical Study Designer 9406 produces standardized CDISC-compliant datasets representing Trial Elements (TE) and Trial Arms (TA). In combination with Study and Protocol Elements application 116 production of the CDISC-compliant datasets Trial Inclusion/Exclusion Criteria (TI) and Trial Summary Elements (TS) and the Schedule of Activities application 114 production of Trial Visits (TV), system 9400 as a whole is capable of automatically producing the full complement of CDISC-compliant Study Design datasets that are required as part of a regulatory submission and are typically assembled in a manual manner from disparate information. In this way, the ability to automatically assemble these datasets may provide significant value to the end user in terms of accuracy and efficiency. System 100 of FIG. 1 provides a third means of Arm definition directly embedded within the Schedule of Activities application.

The capabilities of graphical study designer 9406 may naturally flow into the previously disclosed Schedule of Activities (SOA) application 114. As part of a Study Protocol's specification, each Arm is associated with a Schedule. Within a Study Protocol, multiple Arms may share the same Schedule (as in the case for the double-blinded efficacy study described above, where every subject experiences the Study in an identical manner with the exception of the substance the subject is given), each Arm may be assigned a unique Schedule, or some combination of shared and unique Schedules may be assigned.

During the period when a study protocol is under development, Arms and Schedules may be decoupled. This allows a user of the Schedule of Activities application 114 to detach an Arm from a Schedule in case the Arm design needs to be updated, but the configuration of the Schedule needs to be preserved. In this example, after updating the Arm design the user can attach the temporarily decoupled Schedule again to one or more Arms of the updated Arm design. When a Schedule is not attached to any Arms it is considered an orphaned Schedule.

As noted above, orphaned Schedules are allowed only during protocol development. Upon a user's attempt to lock the Schedule of Activities section, Study Design microservice 126 will validate that no orphaned schedules are present in the study protocol and prevent the section lock from occurring if this is not the case. In other words, as a result of this Arm to Schedule linkage which occurs within the Schedule of Activities application 114, a Schedule may (temporarily) exist without being attached to any Arm (where such Schedule may be referred to as an orphaned Schedule). Support for decoupling of Arms from Schedules accommodates a potential need for designers to be able to delete one or more Arms under development without losing already created Schedules, in particular in the context of using graphical study designer 9406. As a result, Schedules are assigned a human-readable and meaningful label so they can be identified by the user independent of the existence of Arms.

As a peer application to graphical study designer application 9406 as described above, schedule of activities application 114 and underlying study design microservice 126 may support the following Arm and Schedule Management requirements:
1. When an Arm is newly created (regardless of source), it has no related Schedule.
2. A newly created Arm A without a Schedule can acquire a schedule in three ways:
2.1. First, it may attach an existing Schedule X to Arm A. It is possible that X was orphaned before becoming attached to Arm A.
2.2 Second, it may create a new empty Schedule X and attach it to Arm A.
2.3 Third, it may create a new Schedule X as a copy of an existing Schedule Y and attach X to Arm A.
3. Given Arm A related to a Schedule X, it is valid to relate A to another existing Schedule Y. Schedule X may become orphaned as a result of this action. It is possible that Y was orphaned before becoming attached to Arm A.
4. Detach an existing Schedule X from an Arm A. The Arm then returns to the same state as in (1), e.g., an Arm with no related Schedule. Schedule X may become orphaned as a result of this action.
5. The logical action to change an existing Schedule X of an Arm A to a copy of another existing Schedule Y is not directly supported in the Schedule of Activities application 114, as this functionality can be accomplished by first doing (4) followed by (2.3).
6. An Arm without a Schedule can be deleted (unless a Lean Protocol lock is in place). Arm deletion occurs in the application used to generate the initial set of Arms for the Study Protocol.
7. An Arm A with a related schedule X may also be deleted. This results in deletion of Arm A, but not in deletion of associated Schedule X. Schedule X may become orphaned as a result of this action.
8. A Schedule may only be deleted if it is orphaned. To delete a Schedule X that is not orphaned, the user first detaches all Arms from schedule X.

Graphical study designer 9406 may operate as an independent application, or an Arm Table Editor may execute within the Study and Protocol Elements application 116. In both cases the intention is managing Arms (without thinking of Schedules): create arms, update arm attributes, delete arms. For example, creating an Arm defines a new Arm without a related Schedule as in (1) above. Updating Arm attributes is allowed, even if a Schedule is attached to the arm. Deleting an Arm (when not locked) is possible irrespective of whether a Schedule is attached following (6) and (7) above.

A user who does not use the Schedule of Activities application 114 has the capability to manage Arms without ever creating Schedules. If the user has access to Schedule of Activities application 114, creating Arms may not in itself create the overhead of automatically creating Schedules. In combination with Lean Protocol locking, the Arms have been given full consideration by the user before beginning Schedule definition. This may provide separation between managing Arms vs managing Schedules. In one example, a user may choose to enable parallel Arm and Schedule development, whereas in another example a user may choose to configure platform validation rules such that the capability of creating and editing Schedules is prevented until the Arms section has been successfully locked.

When the graphical study designer application 9406 is deployed, the Arm Table within study protocol elements application 116 may be set to read-only. The user may manage Schedules dialog within schedule of activities application 114. If the schedule of activities application 114 is standalone (meaning without arm management by study and protocol elements application 116, Arm table, or graphical study designer application 9406), then the dialog has two sections: Manage Arms and Manage Schedules. If schedule of activities application 114 is deployed with a separate application (either graphical study designer 9406 or study and protocol elements application 116) for Arm management, then the dialog has only the second section Manage Schedules (without user actions to create or delete arms).

The aforementioned is a specific example of the general platform (which is another way of referring to system 9400 or any system set forth in this disclosure) concept of deployment-sensitive application functionality. As such, each application deployed into a platform instance is aware (e.g., via registration or some other process) of all other deployed applications and, based on desired behavior, may enable or disable aspects of its functionality based on the presence or absence of other platform applications within the deployment. Another such example is the enabling or disabling of section unlock capability within the suite of study design-related applications (graphical study designer 9406, study and protocol elements 116, and schedule of activities 114) based on the presence or absence of lean protocol application 9404 described below within the deployment.

When present, the Manage Arms action Create Arm within the schedule of activities application 114 should only create the Arm, but not a default Schedule for that arm, consistent with (1) and the way Arms are created in study and protocol application 116 or graphical study designer 9406. The result of the create arm action is that the Arm is added to the Manage Schedules table, but with no value for Schedule. Where system 9400 provides a Manage Arms section, then an Arm (with or without a Schedule) can be deleted from the Manage Schedules section following (6) or (7) above.

Within the Manage Schedules table of the schedule of activities application 114, graphical study designer 9406 may display only Arm Label from the Arm attributes. This attribute is read-only. Schedule of activities application 114 may assign a Schedule a unique label. When creating a new Schedule, the user provides a label for the Schedule. User actions for (2), (3), (4) and (8) are required for the Manage Schedules section of the dialog.

With respect to the Lean Protocol described below, locking does not change the foregoing, but constrains which of the actions are possible in graphical study designer 9406, Arm Table Editor, and schedule of activities application 114, depending on the locking states of the apps. Without locking capabilities, all of the above may still consistently work (particularly in the case of an Schedule of Activities-only deployment). Locking constraints may force the user to do things in the right order from a domain perspective.

Figure 20:
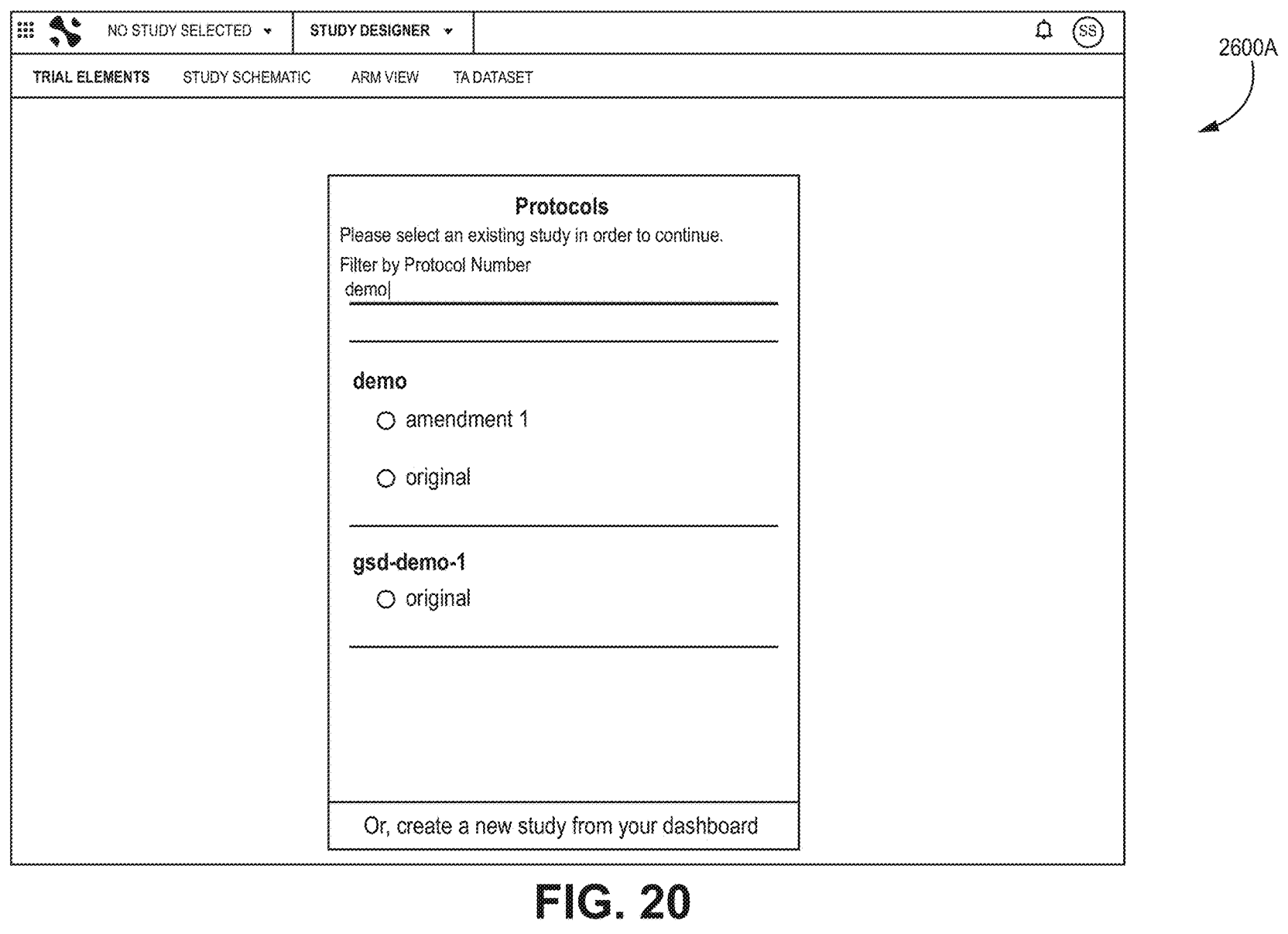

Referring first to the example of FIG. 20, graphical user interface 2600A may represent one example of a user interface presented by graphical study designer 9604 to enable a user to define a study protocol or select an existing study protocol to edit. After selecting a study protocol, such as "GSD-DEMO-1," graphical study designer 9604 may transition to user interface 500B shown in the example of FIG. 21, which enables the user to define Trial Elements datasets, while also being able to switch between Trial Elements, Study Schematic, Arm View, and Trial Activity (TA) datasets via selectors 2602A-2602D. Graphical user interface 2600B may also include an input 2604 by which a user may add new trial elements.

Figure 22:
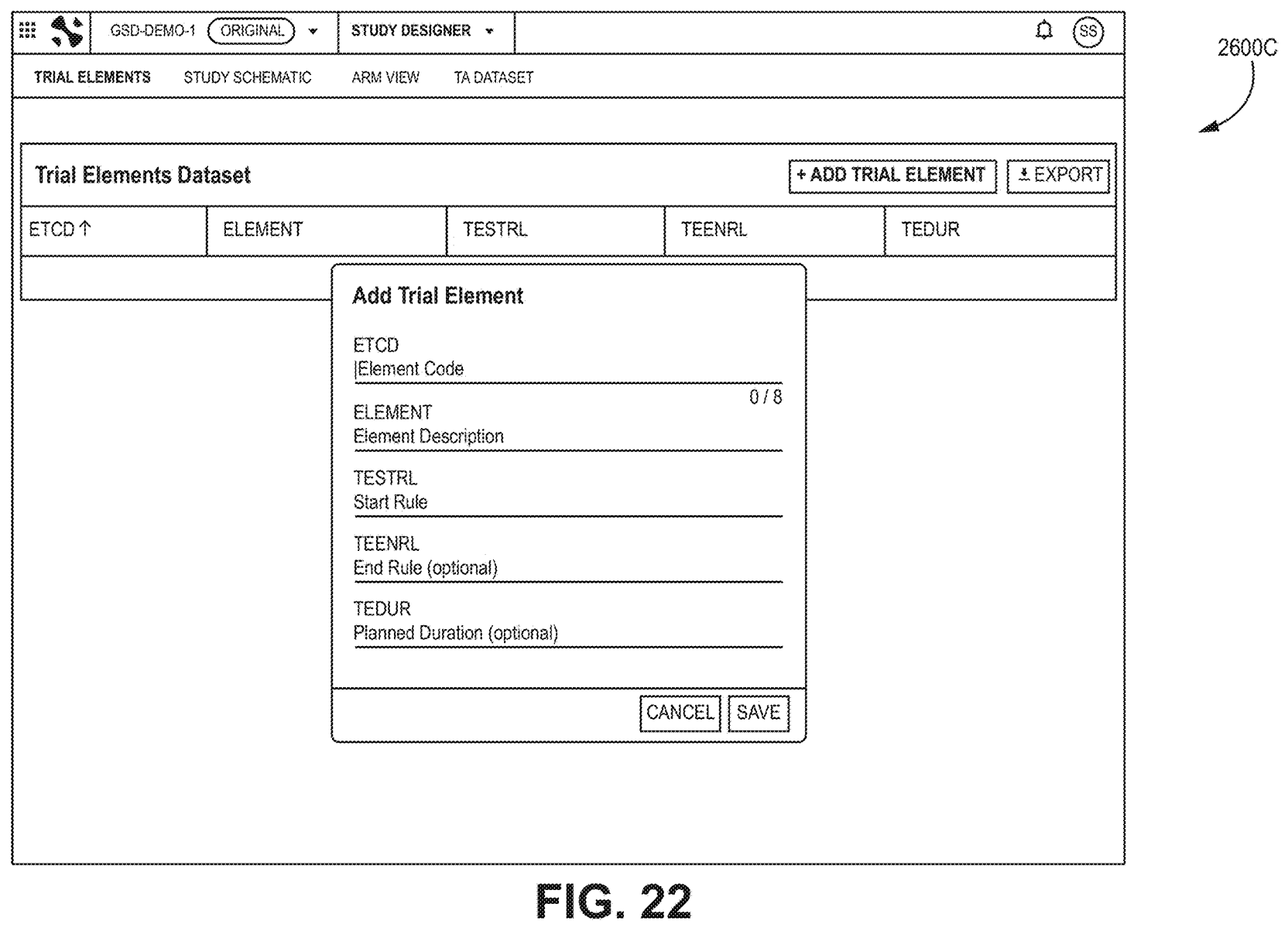

Selecting input 2604 may result in graphical study designer 9604 presenting graphical user interface 2600C, which is shown in the example of FIG. 22. Graphical user interface 2600C may enable definition of a Trial Element having properties of "Element Code," "Element Description," "Start Rule," "End Rule," and "Planned Duration," where various of these properties may be graphically represented for use in study design. The user may iterate in this manner to define the Trial Elements dataset, resulting in an example graphical user interface 2600D shown in FIG. 23.

Graphical user interface 2600D presents a populated Trial Elements dataset having a Drug A, a Drug B, a Placebo, a run-in, and a screen. The user may review the Trial Elements dataset, which may represent an example of statically defined study content 560 shown in the example of FIG. 6. Once the Trial Elements are confirmed, the user may select to transition to the study schematic by selecting selector 2602B, whereupon graphical study designer 9604 may, responsive to receiving the selection of selector 2602B, present a graphical user interface 2600E shown in the example of FIG. 24.

Figure 25:
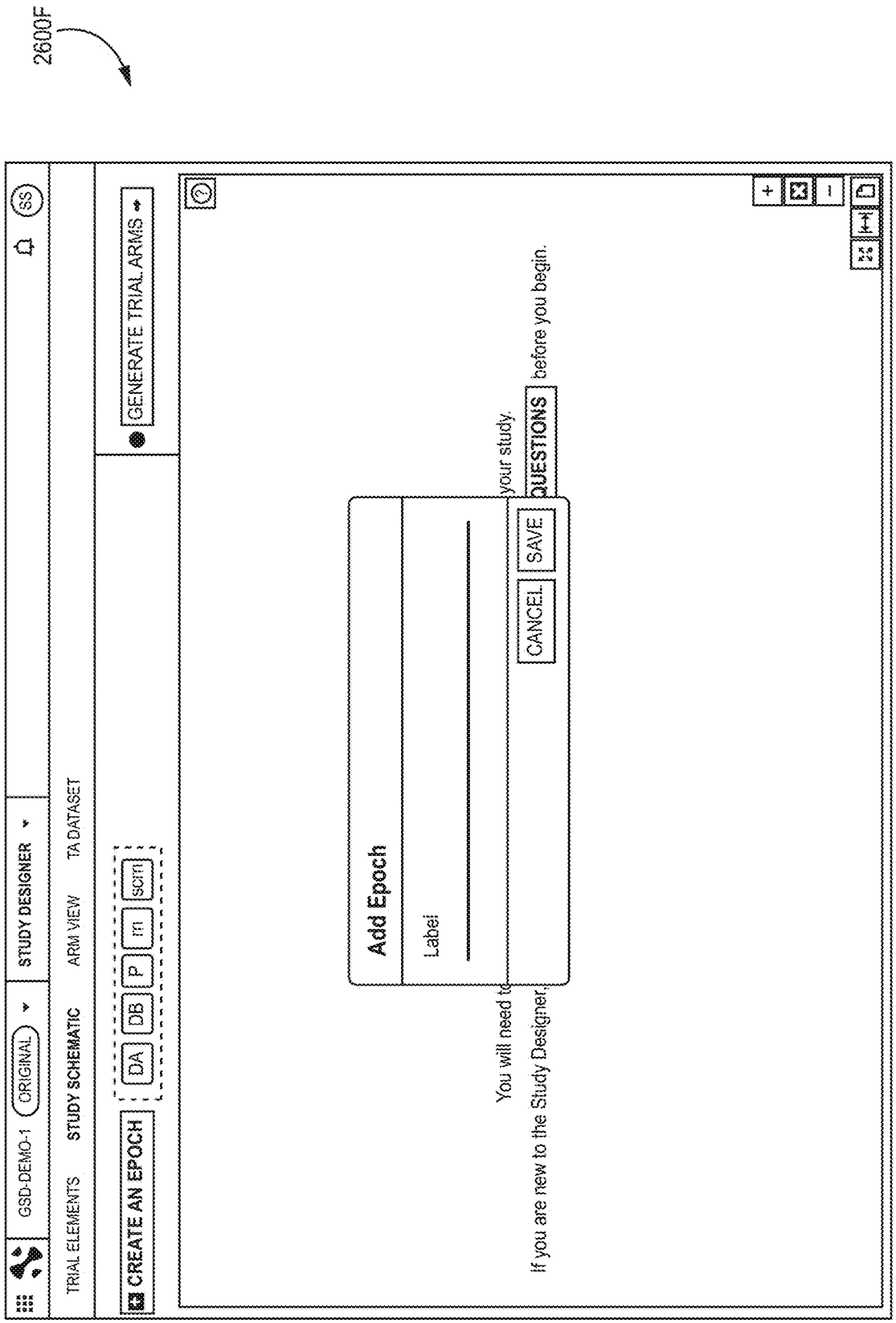

Graphical user interface 2600E enables graphical definition of study. Each study may have one or more Epochs, where graphical user interface 2600E may include an input for adding new Epochs to the current study (which again is denoted as "GSD-DEMO-1"). Graphical user interface 2600E also includes icons 2608, where each icon denotes a different Trial Element (e.g., a Drug A, a Drug B, a Placebo, a run-in, and a screen). Responsive to selecting input 2606, graphical study designer 9604 may generate and present a graphical user interface 2600F, which is shown in the example of FIG. 25.

Figure 26:
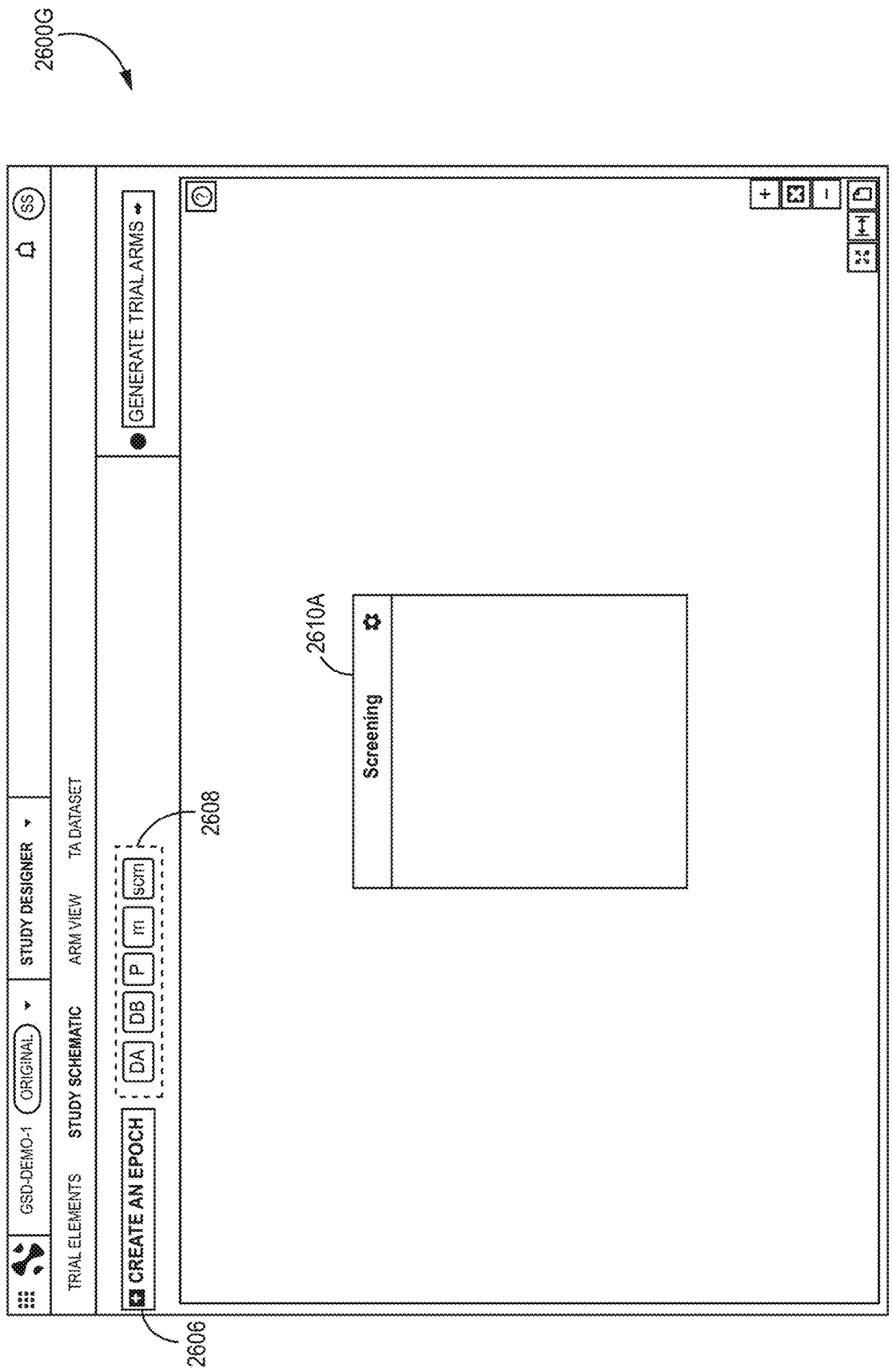
Figure 27:
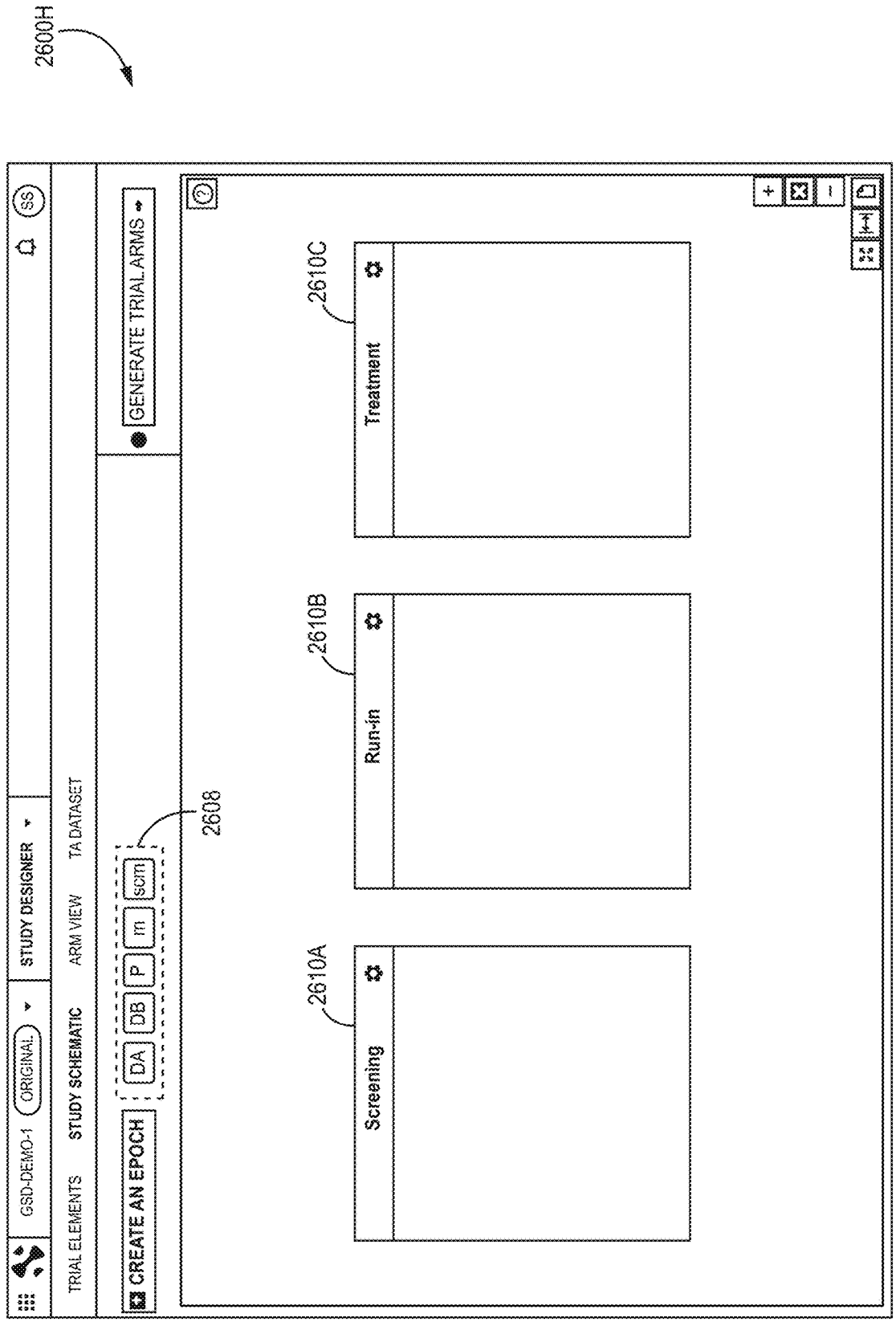

Graphical user interface 2600F may enable definition of an Epoch (e.g., by assigning a name), where graphical study designer 9604 may, responsive to receiving the definition of the Epoch generate a graphical user interface 2600G as shown in the example of FIG. 26. Graphical user interface 2600G may graphically depict the Epoch (entitled "Screening") via graphical element 2610A. Multiple Epochs may be created in this manner, resulting in an example graphical user interface 2600H that is shown in FIG. 27, which includes graphical elements 2610B and 2610C in addition to graphical element 2610A. Graphical element 2610B may represent an Epoch referred to as "Run-in," while graphical element 2610C may represent an Epoch referred to as "Treatment."

Graphical user interface 2600H may enable for dragging various trial element icons 2608 to graphical element 2610A-2610C ("graphical elements 2610") to associate the corresponding trial elements to a given Epoch. Graphical user interface 2600H may also allow for edges to be defined between different trial elements (which may represent nodes of a tree data structure) across the Epochs to define a schedule of events and/or activities. For example, a user may drag the screen (scrn) icon of icons 2608 to graphical element 2610A, the run-in (rn) icon of icons 2608 to graphical element 2610B, and the Drug A (DA), Drug B (DB), and placebo (P) icons of icons 2608 to graphical element 2610C. The user may next link screen icon to run-in icon via an edge, and create separate edges between run-in icon and each of the Drug A, Drug B, and placebo icons, resulting in a graphical user interface 2600I shown in the example of FIG. 28.

In the event that a node is associated via multiple edges with more than one downstream node, the user is informed via graphical representation that further information in the form of a Branching Rule (e.g., randomization) must be specified for each edge. In this respect, system 9400 may determine that nodes (representative of trial elements) have connections to multiple down stream nodes (representative of trial elements, such as a second trial element and a third trial element). Responsive to determining that nodes have connections to multiple downstream nodes, system 9400 may refrain from generating the one or more trial arms until branching criteria has been specified.

Figure 28:
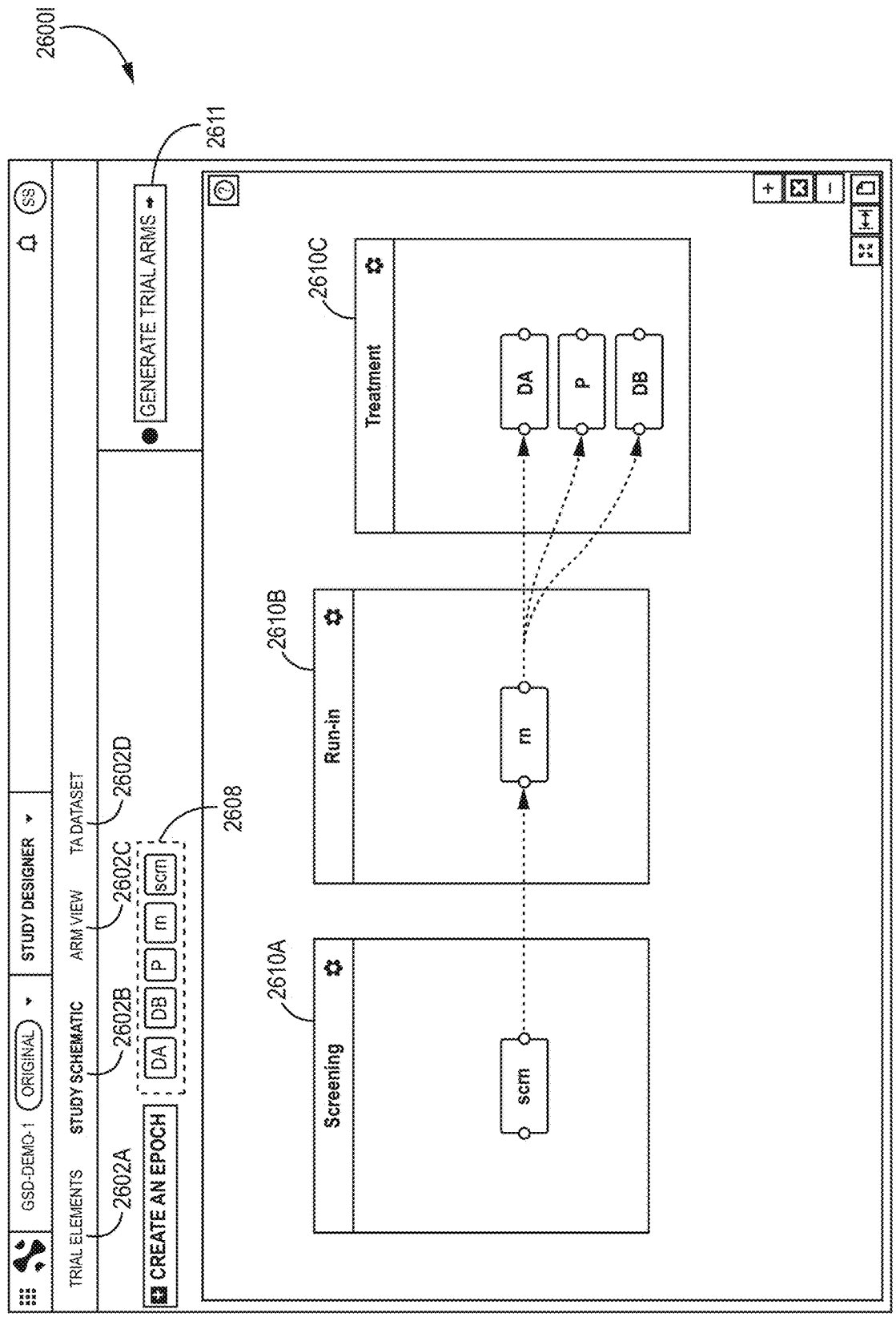

The user may review the created study schematic, and if satisfied, proceed to interact with input 2611 that enables generation of trial arms, where such input 2611 may represent a commit action performed by the user when: 1) all requirements for arm generation have been satisfied, and 2) the user is satisfied with the study design. Responsive to receiving input 2611, graphical study designer 9406 may enable the user to view the arms of the study that are automatically created based on the study schematic shown in user interface 2600I. However, should the user subsequently modify any aspect of the study schematic as represented in the example of FIG. 28, the generated trial arms are invalidated and the user may be required to initiate regeneration of the trail arms via input 2611, where again invocation of this action may be restricted (by system 9400) until all requirements for arm generation have been met.

Figure 29:
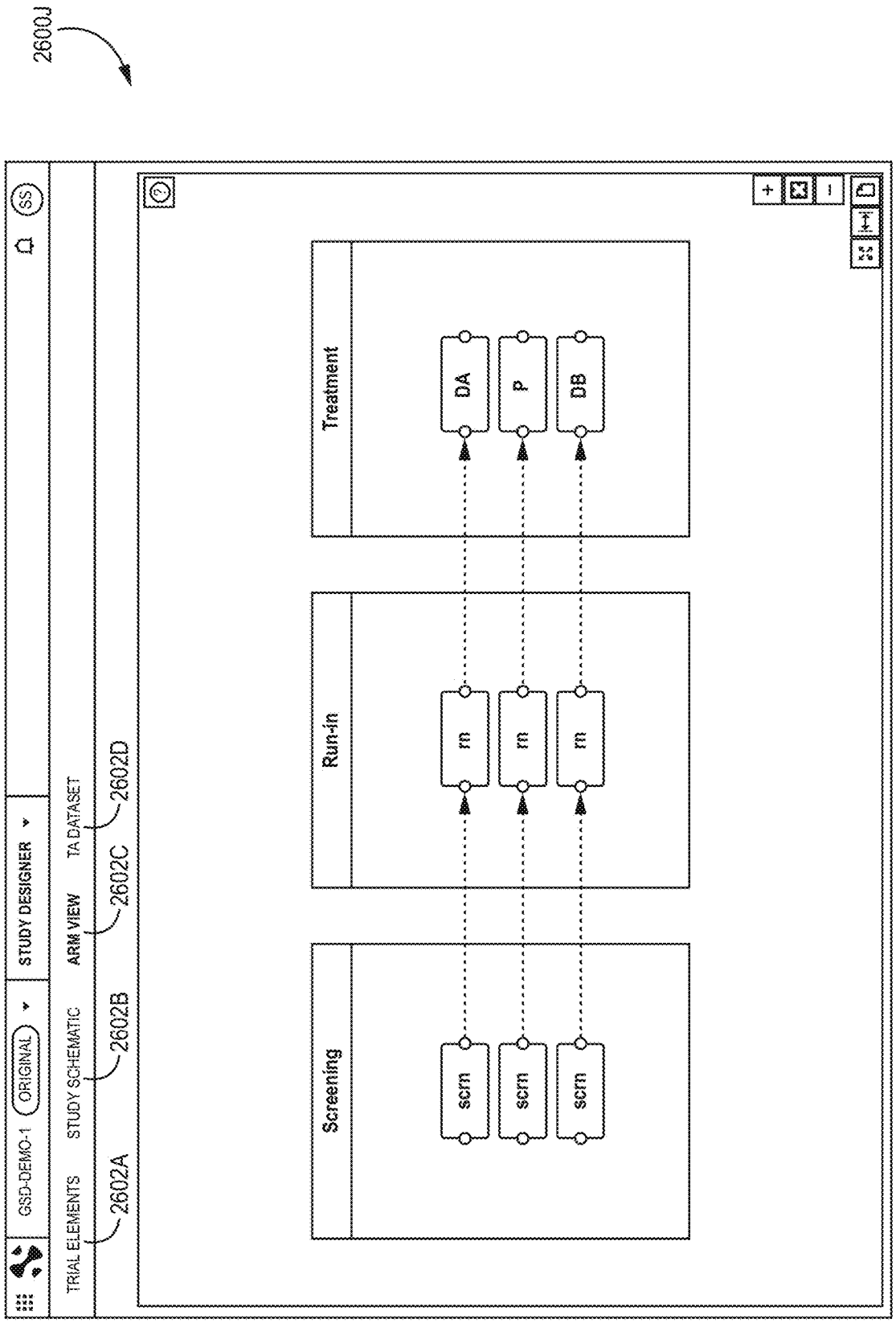

FIG. 29 is a diagram showing graphical user interface 2600J, which graphical study designer 9604 may generate responsive to receiving the input that selector 2602C was selected. Graphical user interface 2600J replicated various icons to graphically depict each arm of the study, where in this example, a first arm includes a screen icon coupled to the run-in icon, which in turn is connected to the Drug A icon, a second arm includes a screen icon coupled to the run-in icon, which in turn is connected to the placebo icon, and a third arm includes a screen icon coupled to the run-in icon, which in turn is connected to the Drug B icon. As such, graphical study designer 9604 may graphically represent, as a tree data structure, a clinical study protocol, and flatten trial arms for a clinical study protocol generated from the tree data set.

The user may next select TA dataset selector 2602D to transition to graphical user interface 2600K, which is shown in the example of FIG. 30 and provides a list of Trial Arms datasets in terms of trial activities.

In this respect, FIGS. 20-30 are illustrations of a GUI clinical study protocol designer in accordance with the techniques of the disclosure. As illustrated in FIGS. 20-30 system 100 of FIG. 1 receives, from a user, an input specifying a plurality of trial elements for a study. System 100 receives, from the user, an input arranging the plurality of trial elements into a tree data structure. System 100 determines, based on the tree data structure of the plurality of trial elements, one or more trial arms for the study. Each trial arm of the one or more trial arms comprises a single path between at least one trial element of the plurality of trial elements to at least one other trial element of the plurality of trial elements. System 100 outputs, for display to the user, the one or more trial arms for the study.

In some examples, the user begins arm design by initially defining a plurality of trial elements. As depicted in the examples of the FIGS. 20-30, the user defines trial elements including screening (scrn), run-in (rn), dosage type A (DA), dosage type B (DB), and placebo (P).

Subsequent to trial element definition, in some examples the user specifies one or more epochs for the study. An epoch describes an interval of time in the planned conduct of a study. As used herein, an epoch is a conceptual construct used to logically group trial elements (also referred to herein as "study elements") with respect to various aspects of trial execution. An epoch is associated with a purpose and applies across all arms of the study. For example, an epoch may be associated with a purpose such as screening, randomization, run-in, treatment, follow-up, etc. As illustrated in the examples of FIGS. 20-30, the user specifies a screening epoch, a run-in epoch, and a treatment epoch.

After defining one or more epochs for the study, in some examples the user specifies each trial element for association with each epoch by dragging-and-dropping a representation of the trial element into a representation of a corresponding epoch. Further, in some examples the user arranges the plurality of trial elements into a tree data structure by, for each trial element, dragging-and-dropping a unidirectional arrow from a trial element to a sequentially subsequent trial element so as to specify an order for which the trial elements are to occur.

Figure 31:
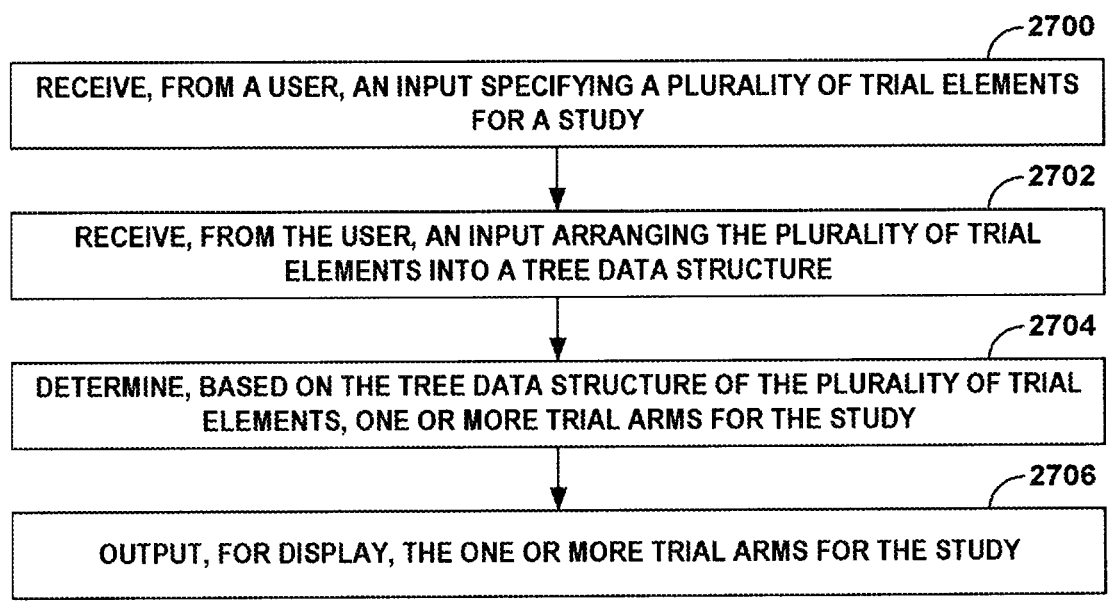
FIG. 31 is a flowchart illustrating example operation of the graphical study designer in performing various aspects of the graphical study design techniques.

FIG. 31 is a flowchart illustrating example operation of the graphical study designer in performing various aspects of the graphical study design techniques. As discussed above, graphical study designer 9604 may initially receive, from a user, an input specifying a plurality of trail elements for a study, and receive, again from the user, an input arranging the plurality of trail elements into a tree data structure (2700, 2702). Graphical study designer 9604 may next determine, based on the tree data structure of the plurality of trail elements, one or more trial arms for the study, and output, for display, the one or more trial arms for the study (2704, 2706).

Referring back to the example of FIG. 19, lean protocol application 9402 may present a clinical study protocol as a sequence of a plurality of stages in accordance with the techniques of the disclosure. In today's environment, it has become increasingly critical to accelerate the clinical development process, maximize efficiency and drive innovation to support the increasing complexity of trials including Platform, Adaptive, Umbrella and Basket Trials. Within the context of a clinical trial and clinical operations processes, activities can be accelerated through what is described herein as the "lean protocol process," which is based on protocol development gates from Clinical Development Plan (CDP) through to final protocol.

This "gated" process begins with the CDP/Protocol workflow (which may be configurable) as the first gate when critical data is first available and enables parallel development of the protocol, SAP and study build to begin. The early availability of critical study data elements further triggers early and parallel development of functional plans and process activities. Using feasibility as an example, study population, planned procedures and reference drugs are identified at gate 1 and trigger development of the feasibility and strategy plan. The protocol is further refined through subsequent gates, enabling early execution of protocol feasibility to begin after gate 2 and site feasibility activities at gate 3 or protocol level 2. The same methodology applies to other functional plan development such as data management (DM) and monitoring. Most importantly, this lean process provides the shared alignment and transparency to generate and address recommendations for changes to the study design before final protocol.

The Lean Protocol process digitizes and standardizes data that is critical to the reliability of the study findings, specifically data that supports primary and key secondary estimands/endpoints. By prioritizing the critical domains and activities based on what is unique to the study such as new/unique tools/procedures or safety considerations as a result of comparator drugs or the indication, the techniques herein may drive informed decisions and risk assessment. For example, one may consider whether there are competitive studies that need to be considered for the study population, whether the inclusion/exclusion criteria are open to interpretation or unclear, or whether the complexity of the study increase risks for execution. Leveraging the early availability of the digitized study-critical elements also facilitates study build such as EDC and RTSM systems and processes.

Critical data for reporting and analysis are also identified early on in the planning phase, driving a potential early start on development of dashboards and reporting specs. Therefore, the lean protocol process driven by data standards and the digital protocol accelerates the lifecycle through to submission data sets that are consistent with the protocol. This "intelligent automation" through the lean protocol process may drive quality, consistency, and behaviors that focus on critical data versus the completeness and accuracy of every data point at the expense of critical aspects. The end result provided by the lean protocol process may enable a significant reduction of the clinical life cycle and submission timeline driven by a systematic quality by design process.

In other words, at high-level, the Lean Protocol supports the following conceptual requirements. Each Study instance is associated with a set of Gates. Gate configuration needs to be supported in an aggregated manner. For example, some gates may be universally applied. As another example, some or all gates may be scoped by TA/Indication/Phase/etc. (e.g., filtered condition set) with the scoping process based on a best-fit algorithm (i.e., where a Lean Protocol definition is selected via application of filtering criteria under increasingly less stringent rules including the potential of selecting a default definition that conforms to none of the specified filtering criteria), or based on an additive algorithm (i.e., where a baseline Lean Protocol definition is augmented by identification of further gates that conform to the specified filtering criteria). Further, some gates may be custom-defined for a specific study. Each Gate rolls up a set of Conditions (Boolean flags). Conditions may include section locks (automated from other system functional microservices), other gates, and/or human-settable flags. Gate approval is enabled by setting of all conditions associated with the Gate. Further, gate approval may be tied to Workflow.

With respect to Lean Protocol Microservice 9404, each declared Gate instance supports a fixed state machine as follows:
  In Progress: the initial state; the instance remains in this state while all gate conditions have not been met.
  Ready for Review: state transition from In Progress is enabled once all gate conditions have been met. This state also enables an approval workflow action. While a Gate is in Ready for Review state, the User can also choose to revert the Gate back to In Progress state (e.g. to force clear a Condition (section lock) because modifications are required in that section).

Under Review: occurs at time of approval workflow initiation

Approved: occurs when workflow successfully completes. An Approved Gate can be rescinded by the user as appropriate (e.g., as described in subsequent paragraph). At the time of rescindment, the user may identify one or more Conditions that are to be unlocked, or may choose to manually review and unlock those sections as a separate action. Depending upon this choice, the Gate's state will be set to In Progress (if the user selects one or more Conditions to be unlocked at time of rescindment) or Ready for Review (if the user chooses to defer the action of Condition review and unlock).

Similar to the Rescind path described above, if Gate approval workflow processing results in rejection, the Gate's state may return to Ready for Review. Alternatively, the state may return to "In Progress" with workflow-driven reset of one or more Gate Conditions based on approver role feedback.

Once a Gate's Conditions are fully set, the ability for the user to submit the Gate into its approval Workflow is enabled for that Gate. Lean Protocol microservice 9404 may also support automated Workflow invocation as a configuration option on a per Gate basis. The full range of Workflow configuration can be applied to Gate approval, where, for example, the workflow may be: Logical no-op (e.g., automatically transitioned gate); simple notification only (e.g., gate has been transitioned); or a human-driven approval process. Per Workflow microservice design, any workflow may incorporate side actions including but not limited to role-based notifications, invocation of external APIs.

Additionally, if a multi-phase gating approach is configured for a Lean Protocol instance, it is possible for a locked Condition for a previously approved Gate to become unlocked in a Phase that is downstream from a prior Phase incorporating that Condition. At this occurrence, Lean Protocol microservice notifies (via asynchronous messages received and acted upon by utility Notifications microservice 134) the appropriate user of this occurrence so as to allow the user an opportunity to rescind the affected Gate approval from the prior phase (e.g., because the unlock action resulted from a significant enough change to the Study Design to warrant revisiting of previous downstream tasks enabled by Gate approval) or to allow the prior phase Gate to remain in the Approved state (e.g., because the user determines that the change is not material to the prior Gate's approval and resulting downstream tasks).

Also, because Conditions can be shared across multiple Gates, such a Condition unlocking can occur for a Gate currently being processed through an Approval workflow (e.g., because a user unlocks that Condition in the context of another Gate); when this occurs, the Workflow microservice informs a user attempting to initiate final Gate approval that unlocked Condition(s) exist. The user is then allowed to Reject the approval request or to instead defer the approval decision until a later time under the assumption that the unlocked Conditions will subsequently become relocked.

A Lean Protocol instance is itself a section within a Study definition. The Lean Protocol section is unlocked at time of instantiation (i.e., when its parent study instance is created), becomes locked when all of its Gates are in the Approved state, and may subsequently become unlocked if any of its previously Approved Gates are rescinded as described above. By specifying the Lean Protocol instance for a Study as a section of that Study, it becomes possible to use Lean Protocol completion as a gating criteria for submission of the Study for final approval and thereby ensuring sufficient scrutiny of all Study contents while at the same time enabling the efficiencies of parallel study development task execution.

Lean Protocol microservice 9404 publishes Gate transitions to an AMQP exchange with an appropriately specified routing key. Likewise, Lean Protocol microservice 9404 publishes messages for Condition unlock requests (and listens for peer messages that indicate the result of unlock requests) and Lean Protocol instance lock and unlock transitions per the previously described algorithm. Lean Protocol microservice 9404 also listens (or in other words, monitors) for inbound section lock messages so as to effect the resulting Condition state changes as required. This messaging enables loosely coupled integration with other applications of system 9400. In some examples, Lean Protocol microservice 9404 state transitions as represented by messages are loosely integrated into existing application integration points of system 9404, e.g., a user attempting to submit a Study Protocol Version for approval may be prevented from that submission if Lean Protocol is installed and the Lean Protocol section is unlocked as described in the prior paragraph.

For Gate/Condition configuration, one applies Study attribute filters to configuration instance (e.g., a Phase 2 trial may establish different gates than a Phase 3 trial, different gates may be set for Oncology vs. Nervous System Disorders Therapeutic Area). Gate definitions are allowed to share Conditions. It is the responsibility of the microservice to ensure fanout of condition state change to all specified Gate instances for a Study.

With respect to UI presentation, Lean Protocol application 9402 may display a Study-specific page presenting all Gates for a Study including Gate status (e.g., In Progress, Ready for Review, Under Review, Approved). When Gate status is Under Review, the user may view and/or launch a current Workflow request form status from the UI of Lean Protocol application 9402.

Lean Protocol application 9402 may display, for each Gate, a list of associated Conditions and their current states. A Gate/Conditions pattern may be implemented in part by using existing dynamic page/section/element generation library components. Other fixed behavior aspects of the platform (e.g., schedule of activities application 114) may also be used to provision a Condition or Conditions into the Lean Protocol application 9402 and lean protocol microservice 9404. A user may launch into another application of system 9400 from a Condition (e.g., hyperlink that opens new tab to the relevant Study and Protocol Elements section, Schedule of Activities, etc.). Lean Protocol application 9402 may provide permissions-based edit control over any human-settable condition values. In some examples, UI framework 102 implements a graphical dashboard that presents Gate status, dates and comments associated with gate states for all Studies.

UI framework 102 may present a cross-study dashboard GUI that presents a bird's eye view of statuses across a large number of protocols based on underlying Lean Protocol gate status. Specifically, the x-axis of the cross-study dashboard may define a plurality of study protocols and the y-axis of the cross-study dashboard GUI may provide a plurality of gates. The column, row entry depicts a status of a gate for a corresponding study protocol.

When Lean Protocol microservice 9404 is present, once a section lock is set within a StudyProtocolVersion the lock may in some examples be reset only via Lean Protocol activity as described above. In some examples, AMQP is used to communicate between Lean Protocol microservice 9404 and functional (section lock managing) microservices of system 100. For example, as a result of user input via the Lean Protocol application 9402, system 100 may require a Condition unlock action to be done on the Gate dashboard, which would send a message to a known topic. Any listeners can then decide what to do with that information. For example, Study Design microservice 126 may then unlock the affected section, emitting an Unlocked message into AMQP which is in turn received and acted upon by Lean Protocol microservice 9404. A corollary to this approach is that section locks are one-way within the scope of the functional microservice/application stack (where, in other words, once a section is locked, such section may only be unlocked via the Lean Protocol app/microservice 9402/9404 stack per above when present).

Section unlock controls within functional application may be modal based on presence/absence of Lean Protocol application 9402 (e.g., if Lean Protocol application 9402 is not present, then unlock action needs to be enabled via permission within the functional app). Gate status may be wired into StudyProtocolVersion approval action (e.g., one may not initiate Study approval for original or amendment until all Gates for that Study are approved). Study Amendment creation may implement a dialog that allows a user to determine which Locks are to be reset upon instantiation of the new Amendment.

Figure 32:
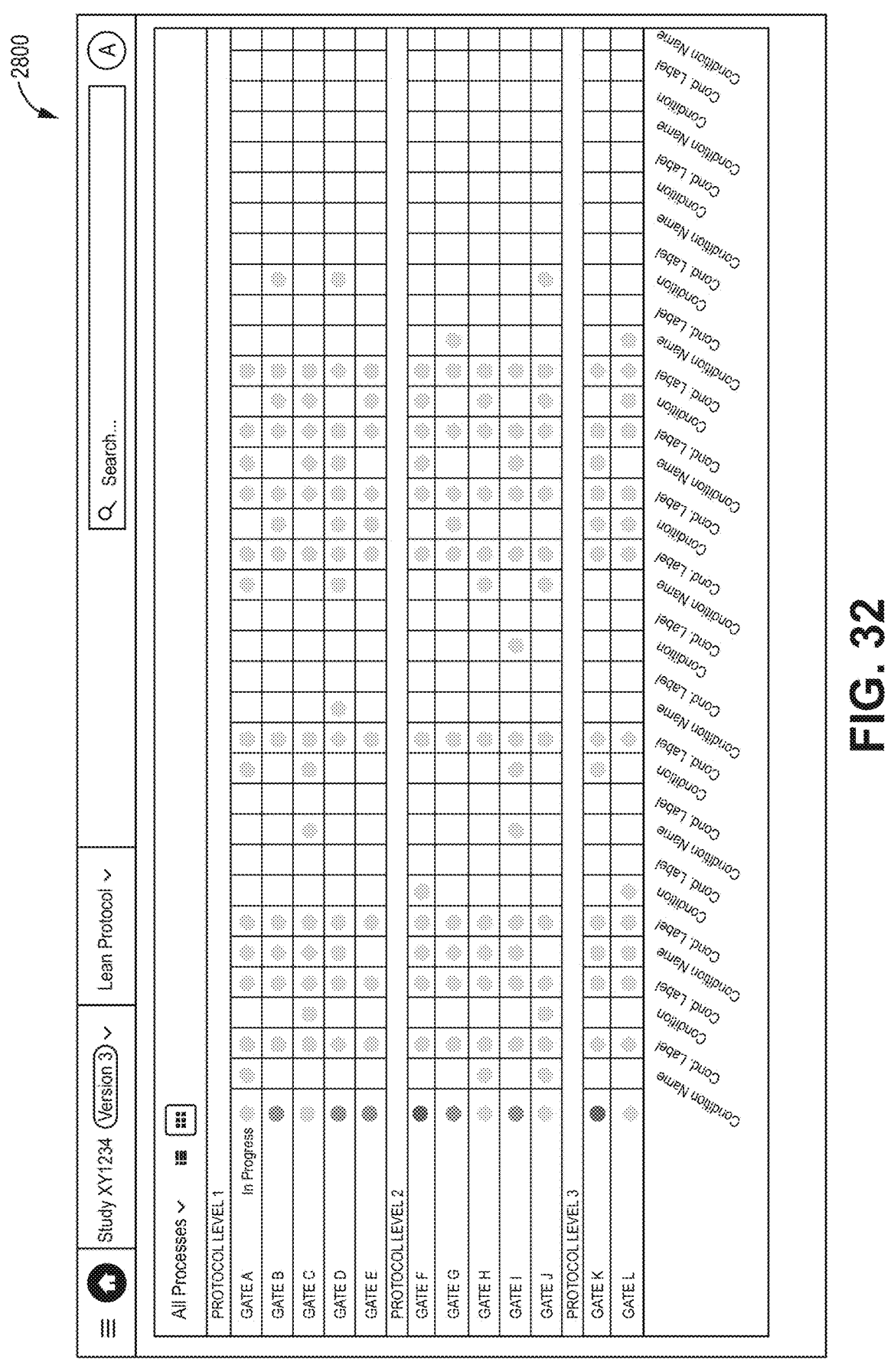

FIG. 32 is a diagram illustrating a graphical user interface that includes statuses of a plurality of gates for a single study. As shown in the example of FIG. 32, graphical user interface 2800 presents a chart in which the x-axis illustrates a plurality of conditions and the y-axis illustrates a plurality of gates. The column, row entry depicts a status of a gate for a corresponding condition of the study protocol.

Figure 33:
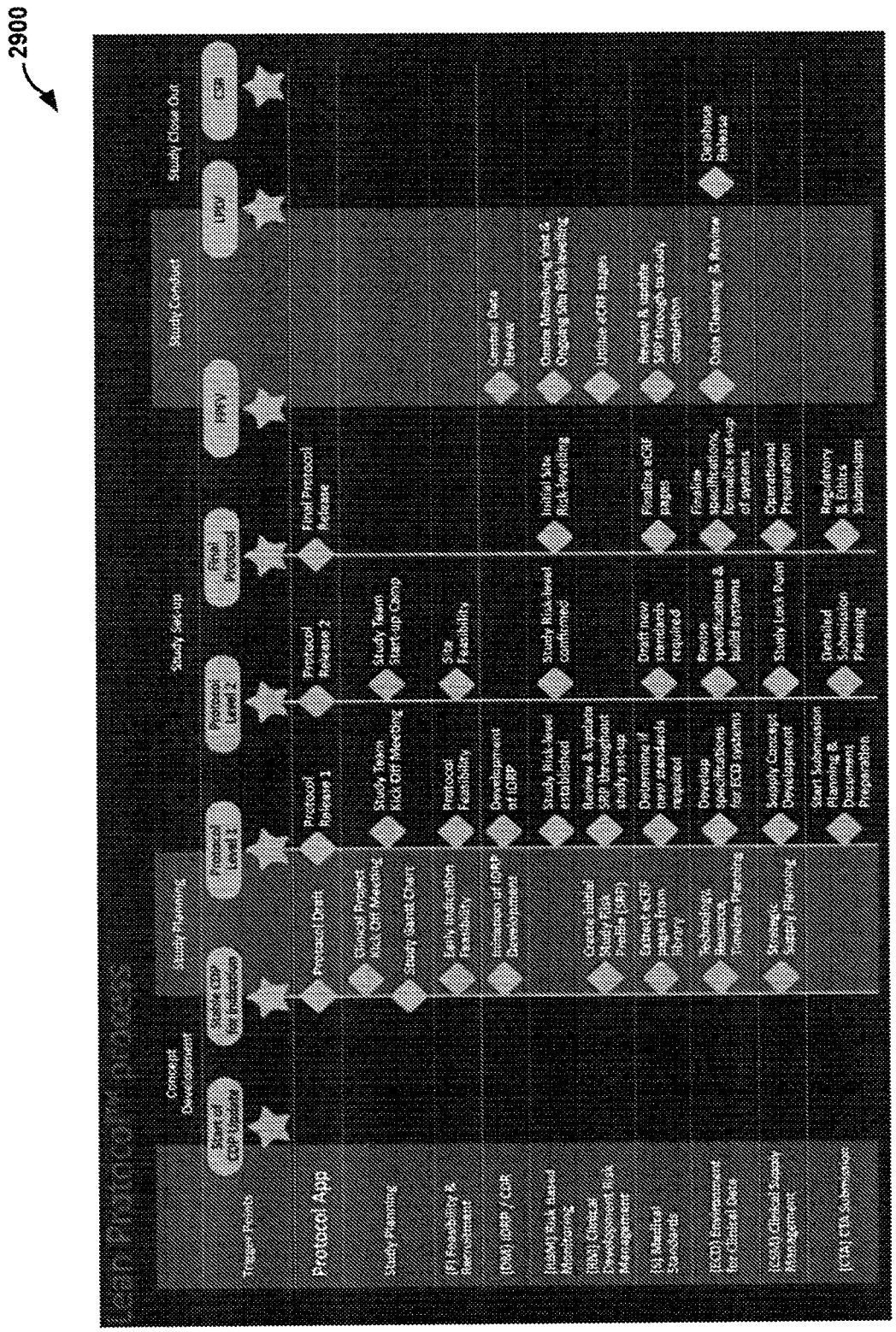
FIG. 33 is a diagram illustrating an example conceptual representation of a clinical study protocol as a sequence of a plurality of stages as applied to typical study planning activities in accordance with the techniques of the disclosure.

FIG. 33 is a diagram illustrating an example conceptual representation of a clinical study protocol as a sequence of a plurality of stages as applied to typical study planning activities in accordance with the techniques of the disclosure. In the example of FIG. 33, conceptual representation 2900 shows a bird's eye view of various gating "swim lanes" (also referred to herein as "lanes") specifying downstream process categories associated with Study Protocol implementation. In the example shown in FIG. 33, there are eight example process categories listed down the vertical axis (and repeated below): Feasibility and Recruitment, IDMP/CDR, Risk-Based Monitoring, Clinical Development Risk Management, Medical Standards, Environment for Clinical Data, Clinical Supply Management, and CTA Submission. Each diamond in a swimlane equates to a Lean Protocol Gate, and the swimlanes themselves equate to Lean Protocol Gate Categories. Such process categories are provided by examples only. In other examples, customers may use these processes, other processes not expressly described herein, or provide their own custom-defined processes or swim lanes in accordance with the techniques of the disclosure.

Figure 34:
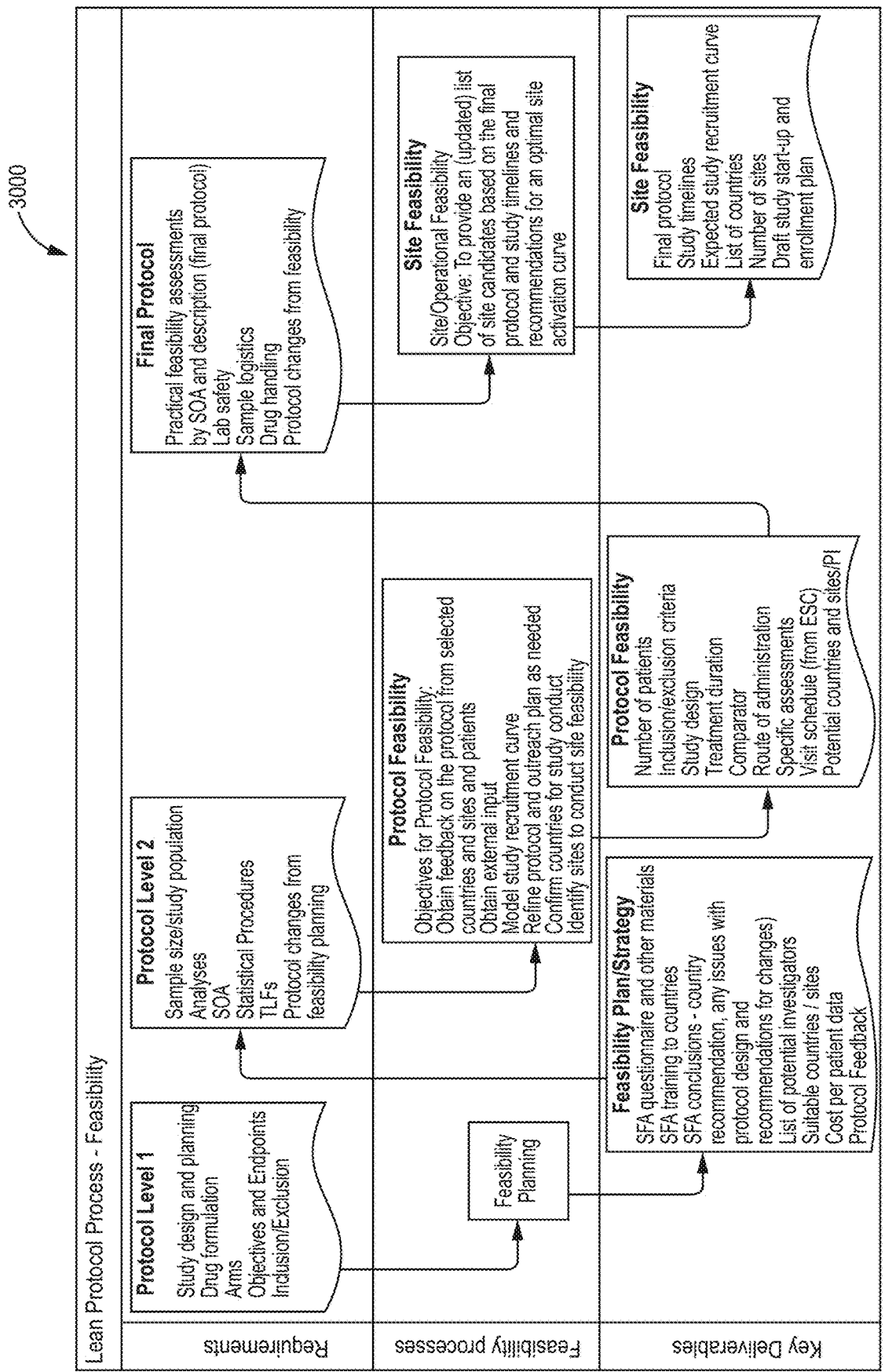
FIG. 34 is an illustration of an example process flow representation of a clinical study protocol that is represented as a sequence of a plurality of stages in accordance with the techniques of the disclosure.

FIG. 34 is an illustration of an example process flow representation of a clinical study protocol that is represented as a sequence of a plurality of stages in accordance with the techniques of the disclosure. For example, FIG. 34 depicts a graphical user interface 3000 of an example process flow against one "swimlane" of the overall Study planning process of FIG. 33. GUI 3000 of FIG. 34 illustrates how one swimlane (e.g., Feasibility and Recruitment) might be implemented within a Lean Protocol configuration. The three objects in the Requirements row equate to Gates, and the list within each object equates to the set of Conditions required to fulfill the Gate requirements. Specifically, when mapped to an example configuration, the Gate entitled "Protocol Level 1" in the diagram depends upon the following Study Protocol Version sections being locked: Study Planning, Trial Arms, Planned Intervention, Interventions, Objectives and Endpoints, Inclusion Criteria, and Exclusion Criteria. Other swim lanes as represented in FIG. 33 may have similar process flow representations.

In some examples, a Lean Protocol configuration may also be defined to represent the aggregation of stages across swim lanes by introducing a "closing gate" for each stage, where the closing gate's conditions are made up of the aggregation of swim lane gates for the stage. In the example of FIG. 33, each of the bottom eight rows of the diagram represents a swim lane, and the vertical bars labeled "Protocol Level 1", "Protocol Level 2" and "Final Protocol" represent stages.

Lean protocol application 9402 may also present GUIs that depict sections/conditions within a clinical study protocol that are in turn consumed by Lean Protocol gates in accordance with the techniques of the disclosure. The GUI may be configured via the dynamic properties mechanism described above. Feasibility and Recruitment is incrementally specified/refined in three stages as part of Study planning work. Each stage represents a Gate with Conditions, where the Protocol Level 2 Gate builds upon the Key Deliverables enabled by Protocol Level 1 Gate approval (and whose Gate contents are influenced by those Key Deliverables as shown by the flow arrow from Level 1 Key Deliverables to Level 2 Protocol), and likewise Protocol Level 3 builds upon the results of Protocol Level 2. This allows for the incremental buildout of downstream process swim lanes. The figures provided represent examples of sections that are relevant to Level 1 Feasibility and Recruitment.

Lean protocol application 9402 and lean protocol microservices 9404 may also operate according to a state machine for a sequence of a plurality of stages defining a clinical study protocol in accordance with the techniques of the disclosure. A gate may be in 4 possible states:
1. Not all gate conditions are met. (Indicated by "In Progress").
2. All gate conditions are met. (Indicated by "Ready to Review").
3. Gate approval workflow started. (Indicated by "Under Review").
4. Gate approved. (Indicated by "Approved").

Figure 35:
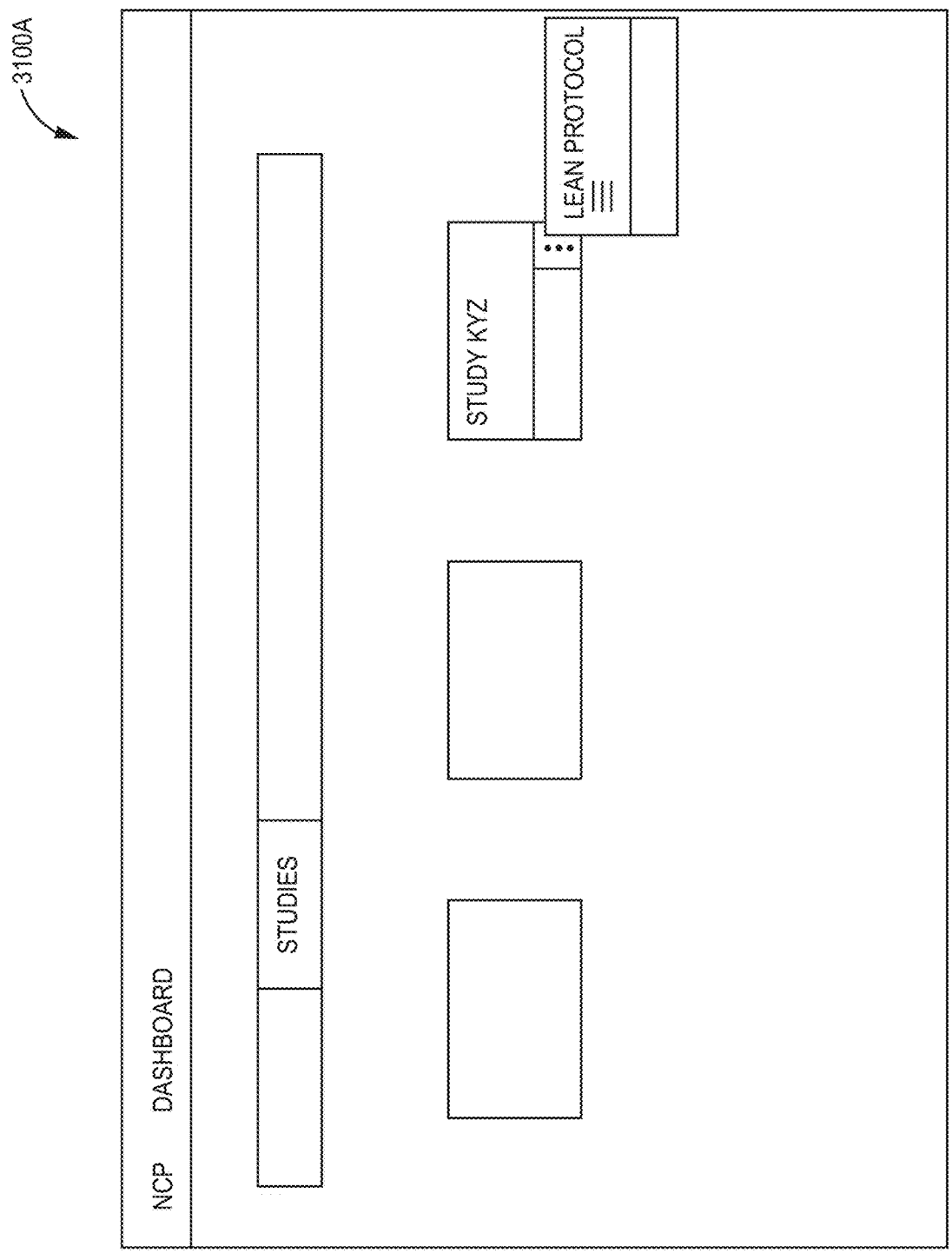
FIGS. 35 and 36 are illustrations of an example GUI that presents a clinical study protocol as a sequence of a plurality of stages in accordance with the techniques of the disclosure.
Figure 36:
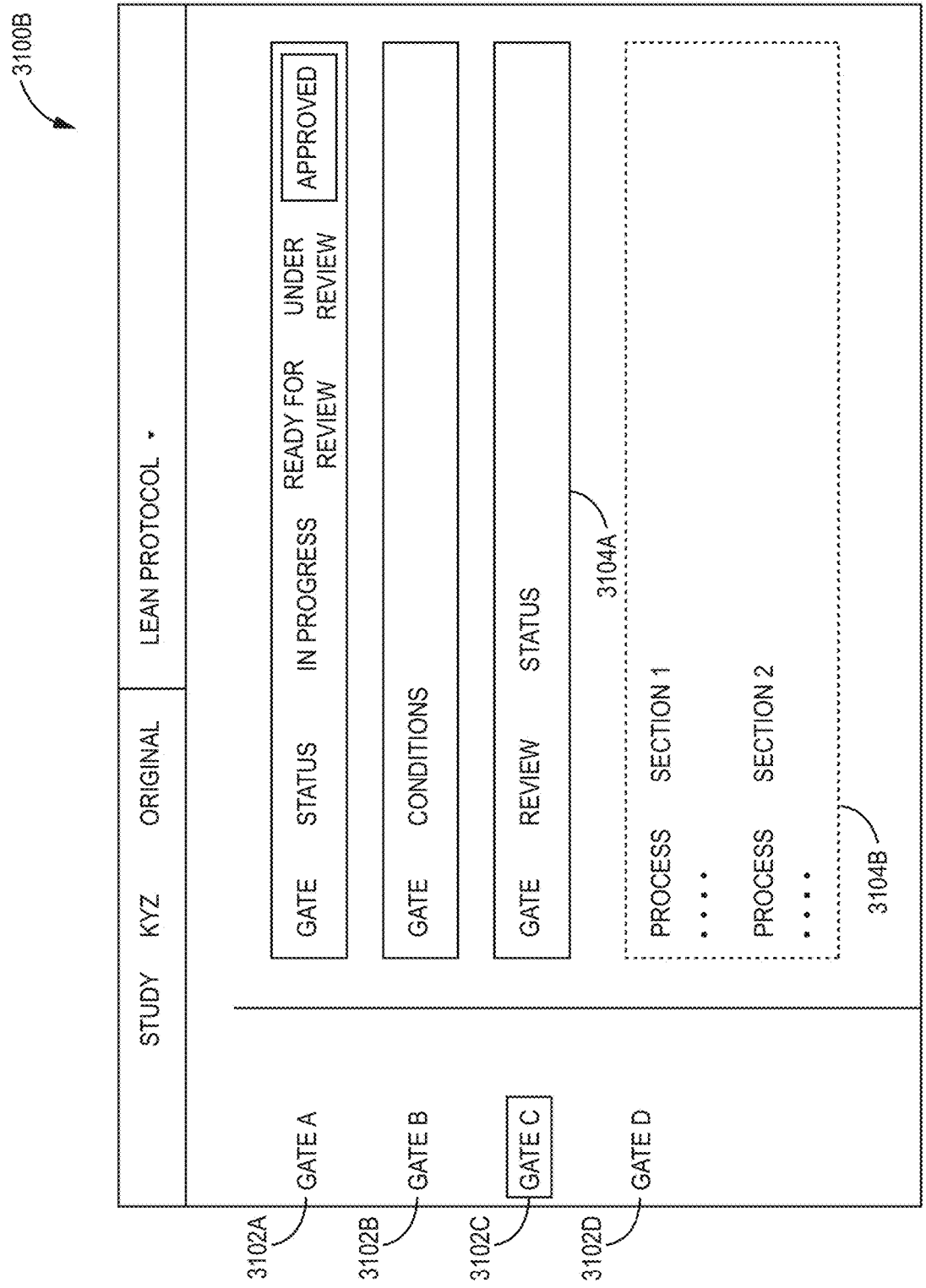

FIGS. 35 and 36 are illustrations of an example GUI that presents a clinical study protocol as a sequence of a plurality of stages in accordance with the techniques of the disclosure. FIG. 35 is an example GUI 3100A representing how a user may invoke Lean Protocol application 9402 of FIG. 19 from a dashboard interface representing a plurality of clinical study protocols.

As illustrated in FIGS. FIG. 36, graphical user interface 3100B includes a graphical elements 3102A-3102D, each of which represents protocol gates, where each Study Protocol Version can have a number of protocol gates. Each protocol gate depends on a set of gate conditions. Gate conditions can be of three types:
1. Conditions depending on protocol sections (e.g., locked, unlocked).

2. Conditions depending on other gates (e.g., locked, unlocked).
3. Manual conditions.

The set of conditions and gates can be configured optionally depending on study attributes (phase, trial arm, etc.).

In some examples, FIG. 36 may depict conceptual diagram 3100B that is substantially similar to conceptual diagram 2900 depicted in FIG. 33. However, conceptual diagram 3100B also includes a Gate Review Status graphical element 3104A and a Process Sections graphical element 3104B. Gate Review Status graphical element 3104A may provide a way by which to capture Lean Protocol Owner notes on gate activities. The Process Sections graphical element 3104B may represent a way by which to present information and status about downstream clinical study planning activities triggered by completion of a Lean Protocol gate.

Figure 37:
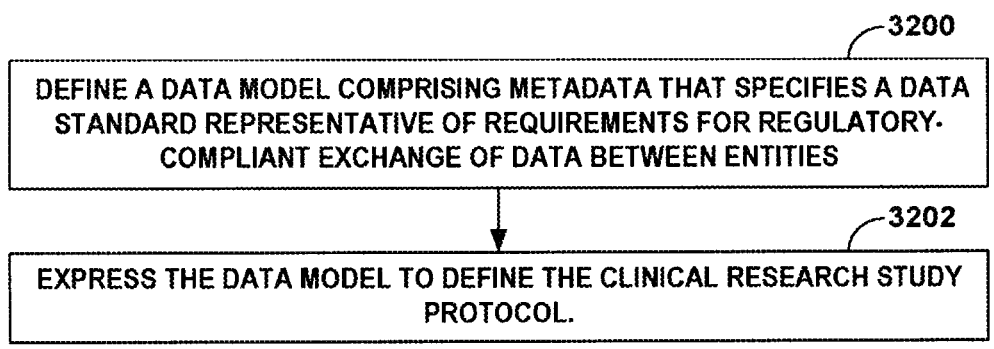
FIG. 37 is a flowchart illustrating example operation of the system shown in FIG. 19 in performing various aspects of the lean protocol techniques described in this disclosure.

FIG. 37 is a flowchart illustrating example operation of the system shown in FIG. 19 in performing various aspects of the lean protocol techniques described in this disclosure. As shown in the example of FIG. 37, lean protocol application 9402 and/or lean protocol microservice 3404 (which may be denoted as lean protocol system 9402/9404) may define a data model comprising metadata that specifies a data standard representative of requirements for regulatory-compliant exchange of data between entities (3200). As described above, the data model includes one or more client objects, each client object specifying a sequence of a plurality of gates for a process of a clinical research study protocol, where each gate of the plurality of gates defines one or more conditions for completion of the gate. Lean protocol system 9402/9404 may then express the data model to define the clinical research study protocol (3202).

As such, various aspects of the techniques may enable one or more of the following examples:

Example A1. A method comprising: defining, by processing circuitry, a data model comprising metadata that specifies a data standard representative of requirements for regulatory-compliant exchange of data between entities, wherein the data model includes one or more client business objects, each client business object specifying one or more study events or associated study elements, and each study event of the one or more study events specifying one or more study activities to be executed for the study event, and wherein the data model includes one or more properties for each of the client business objects that organize the client business objects into one or more property groups, and expressing, by the processing circuitry, the data model to define one or more templates for a clinical research study comprising a sequence of the one or more study events.

Example A2. The method of example 1, wherein expressing the data model to define one or more templates for a clinical research study comprising the sequence of the one or more study events comprises: expressing the data model to define one or more templates for at least one study objective and at least one study endpoint; and parameterizing the one or more templates for at least one study objective and at least one study endpoint to obtain the sequence of the one or more study events.

Example A3. The method of any of examples A1-A2, further comprising parameterizing, by the processing circuitry, the one or more templates for the clinical research study to obtain a schedule of study activities to be executed for each study event of the sequence of the one or more study events.

Example A4. The method of any of examples A1-A3, wherein expressing the data model to define one or more templates comprises expressing the one or more properties for each of the client business objects to define: one or more study objective templates; and one or more study endpoint templates.

Example A5. The method of any of examples A1-A4, wherein the data model conforms to a data description language and specifies which data elements must be collected and a format in which the data elements are to be collected.

Example A6. The method of any of examples A1-A5, further comprising storing, by the processing circuitry, the data model in an International Organization for Standardization (ISO) 11179-based metadata registry (MDR) database.

Example A7. The method of any of examples A1-A6, wherein each study activity of the one or more study activities is selected from a group comprising at least: a clinical treatment or procedure to be performed on a subject; a data element to be measured from the subject; or non-treatment related data of the subject.

Example A8. The method of any of examples A1-A7, wherein each property of the one or more properties specifies a value for a property type for the property, the property type selected from a group comprising at least: a date; a time; a string; a uniform resource locator (URL); a Boolean; a member of an pre-defined list; or an integer;

Example A9. The method of any of examples A1-A8, wherein each of the one or more properties are strongly typed.

Example A10. The method of any of examples A1-A9, wherein each of the one or more properties specifies a dependent relationship to another property of the one or more properties.

Example A11. The method of any of examples A1-A10, wherein each property group of the one or more property groups specifies at least one of: an ordinality of the property group in a property group hierarchy; or a microservice associated with the property group.

Example A12. The method of any of examples A1-A11, wherein each property group of the one or more property groups comprise one of: a clinical research study; a clinical research study protocol; a clinical research study version; a clinical research study design; or a clinical research study arm.

Example A13. A computing device configured to perform the method of any of examples A1-A12.

Example A14. A computing device comprising means for performing the method of any of examples A1-A12.

Example A15. A system configured to perform the method of any of examples A1-A12.

Example B1. A method comprising: retrieving, by processing circuitry and from a regulatory database, a template based on a governance process; receiving, by the processing circuitry and via a user interface, input from a user; parameterizing, by the processing circuitry, the template based on the governance process with the user input to create a parameterized template; and storing, by the processing circuitry, the parameterized template in a database.

Example B2. The method of example B1, further comprising: generating, by the processing circuitry and based on the parameterized template, at least one study objective and at least one study endpoint for a clinical research study; generating, by the processing circuitry and based on the at least one study objective and the at least one study endpoint, a sequence of one or more study events specifying one or more study activities to be executed for the study event; and exporting, by the processing circuitry and to the regulatory database, metadata for the clinical research study.

Example B3. The method of example B2, wherein exporting the metadata for the clinical research study comprises: retrieving, by the processing circuitry and from the database, a graph data structure representative of the clinical research study; generating, by the processing circuitry and from the graph data structure representative of the clinical research study, a tree data structure representative of the metadata for the clinical research study; and storing, by the processing circuitry and in the regulatory database, the tree data structure representative of the metadata for the clinical research study.

Example B4. The method of any of examples B2-B3, wherein exporting the metadata for the clinical research study comprises exporting the metadata for the clinical research study according to a predefined file format.

Example B5. The method of any of examples B2-B4, further comprising defining, by the processing circuitry and based on the parameterized template, a database for storing data collected for the clinical research study.

Example B6. The method of any of examples B1-B5, wherein the template based on the governance process comprises a clinical research study objective template, and wherein parameterizing the template comprises parameterizing the clinical research study objective template to obtain one or more study objectives for a clinical research study.

Example B7. The method of any of examples B1-B6, wherein the template based on the governance process comprises a clinical research study endpoint template, and wherein parameterizing the template comprises parameterizing the clinical research study objective template to obtain one or more study endpoints for a clinical research study.

Example B8. The method of any of examples B1-B7, wherein the regulatory database comprises a metadata registry (MDR) database.

Example B9. The method of example B8, wherein the MDR database comprises an International Organization for Standardization (ISO) 11179-based MDR database.

Example B10. The method of any of examples B1-B9, wherein the database is configured to receive a GraphQL query or mutation.

Example B11. A computing device configured to perform the method of any of examples B1-B10.

Example B12. A computing device comprising means for performing the method of any of examples B1-B10.

Example B13. A system configured to perform the method of any of examples B1-B10.

Example C1. A method for copying a first node of a tree data structure, the method comprising: duplicating, by processing circuitry, a first node to create a duplicate node, wherein the first node comprises an inbound edge to a parent node of the first node and at least one outbound edge to at least one child node of the first node; creating, by the processing circuitry, an inbound edge of the duplicate node to the parent node of the first node and an outbound edge to the at least one child node of the first node; receiving, by the processing circuitry, an update to the at least one child node of the first node; in response to determining that the at least one child node has multiple parent nodes: duplicating, by the processing circuitry, the at least one child node to create a duplicate child node; creating, by the processing circuitry, an outbound edge of the duplicate node to the duplicate child node; deleting, by the processing circuitry, the outbound edge of the duplicate node to the at least one child node; and performing, by the processing circuitry, the update to the at least one child node.

Example C2. The method of example 1, further comprising: duplicating, by the processing circuitry, one or more child nodes of the child node to create one or more duplicate child nodes of the child node; and creating, by the processing circuitry, an outbound edge of the duplicate child node to each of the one or more duplicate child nodes of the child nodes.

Example C3. A method for deleting a first node of a tree data structure, the method comprising: determining, by processing circuitry, that the first node has multiple parent nodes, wherein the first node comprises multiple inbound edges from the multiple parent nodes of the first node and at least one outbound edge to at least one child node of the first node; in response to determining that the first node has multiple parent nodes: determining, by the processing circuitry, a closest superior ancestor node of the first node that has only a single parent node: duplicating, by the processing circuitry, the superior ancestor node of the first node to create a duplicate superior ancestor node; duplicating, by the processing circuitry, a branch descending from the superior ancestor node of the first node to create a duplicate branch descending from the duplicate superior ancestor node, wherein the duplicate branch descending from the duplicate superior ancestor node duplicates nodes and edges of the branch descending from the superior ancestor node of the first node; and deleting, by the processing circuitry, the first node and any inferior descendent nodes of the first node.

Example C4. A method for deleting a first node of a tree data structure, the method comprising: determining, by processing circuitry, that the first node comprises at least one outbound edge to at least one child node of the first node, wherein the first node comprises an inbound edge to a parent node of the first node; determining, by the processing circuitry and based on inbound edges of the at least one child node to the first node and to a second node, that the at least one child node has multiple parent nodes; and deleting, by the processing circuitry, the first node, an outbound edge of the parent node to the first node, and the inbound edges of the at least one child node to the first node.

Example C5. The method of any of examples C1-C4, further comprising: retrieving, by the processing circuitry, the tree data structure from a storage medium; updating, by the processing circuitry, the tree data structure with data for the first node; and storing, by the processing circuitry, the updated tree data structure.

Example C6. The method of any of examples C1-C5, wherein the first node comprises data for one of a study, a study protocol, a study protocol version, a study design, or a study schedule.

Example C7. The method of any of example C1-C6, wherein the first node comprises data for one of a clinical research study, a clinical research study protocol, a clinical research study protocol version, a clinical research study design, a clinical research study schedule, or a clinical research study arm.

Example C8. A computing device configured to perform the method of any of example C1-C7.

Example C9. A computing device comprising means for performing the method of any of examples C1-C7.

Example C10. A system configured to perform the method of any of examples C1-C7.

Example D1. A method comprising: retrieving, by processing circuitry and from a regulatory database, a template based on a governance process; receiving, by the processing circuitry and via a user interface, input from a user; parameterizing, by the processing circuitry, the template based on the governance process with the user input to create a parameterized template; and generating, by the processing circuitry and based on the parameterized template, a clinical research study comprising a sequence of one or more study events specifying one or more study activities to be executed for the one or more study events; and presenting, by the processing circuitry, via the user interface, and to the user, the clinical research study.

Example D2. The method of example D1, wherein the clinical research study further comprises one or more study elements associated with the one or more study events.

Example D3. The method of any of examples D1-D2, wherein generating, based on the parameterized template, the clinical research study comprising the sequence of one or more study events comprises: generating, based on the parameterized template, at least one study objective and at least one study endpoint for the clinical research study; and generating, based on the at least one study objective and the at least one study endpoint for the clinical research study, the sequence of the one or more study events specifying the one or more study activities to be executed for the study event.

Example D4. The method of any of examples D1-D3, wherein parameterizing the template based on the governance process with the user input to create the parameterized template comprises: displaying, by the processing circuitry, via the user interface, and to the user, one or more input types and one or more values for each of the one or more input types, and receiving, via the user interface and from the user, a selection of a value of the one or more values for each of the one or more input types; and parameterizing the template based on the governance process with the selection of the value of the one or more values for each of the one or more input types to create the parameterized template.

Example D5. The method of any of examples D1-D4, wherein receiving the input from the user comprises receiving a user input specifying a selection of one or more values for: one or more study protocol elements; one or more study design elements; or one or more study model elements.

Example D6. The method of any of examples D1-D5, wherein receiving the input from the user comprises receiving a user input specifying one or more secondary or exploratory study objectives or one or more secondary or exploratory study endpoints.

Example D7. The method of any of examples D1-D6, further comprising: determining, by the processing circuitry, a cost estimate for the one or more study activities to be executed for each study event of the one or more study events; determining, by the processing circuitry and based on the cost estimate for the one or more study activities to be executed for each study event of the one or more study events, a total cost estimate for the at least one study endpoint; and displaying, by the processing circuitry and via the user interface, the cost estimate for the one or more study activities to be executed for each study event of the one or more study events and the total cost estimate for the at least one study endpoint.

Example D8. The method of any of examples D1-D7, further comprising: determining, by the processing circuitry and based on the sequence of the one or more study events, a timeline for the clinical research study; and displaying, by the processing circuitry and via the user interface, the timeline for the clinical research study.

Example D9. The method of example D8, wherein the timeline further comprises a schedule for each of the one or more study activities to be executed for each study event of the one or more study events.

Example D10. The method of any of examples D1-D9, wherein presenting, via the user interface, the clinical research study comprises presenting, via user interface embedded within a dashboard web application, the clinical research study.

Example D11. The method of any of examples D1-D10, further comprising: generating, by the processing circuitry and based on the parameterized template, one or more reporting criteria for the clinical research study; and displaying, by the processing circuitry and via the user interface, one or more reporting criteria for the clinical research study.

Example D11. A computing device configured to perform the method of any of examples D1-D11.

Example D12. A computing device comprising means for performing the method of any of examples D1-D11.

Example D13. A system configured to perform the method of any of examples D1-D11.

Example 1E. A method comprising: defining, by processing circuitry, a data model comprising metadata that specifies a data standard representative of requirements for regulatory-compliant exchange of data between entities, wherein the data model includes one or more client objects, each client object specifying a sequence of a plurality of gates for a process of a clinical research study protocol, wherein each gate of the plurality of gates defines one or more conditions for completion of the gate; and expressing, by the processing circuitry, the data model to define the clinical research study protocol.

Example 2E. The method of example 1E, wherein the method further comprises: outputting, by the processing circuitry, an indication that the process of the clinical research study protocol is at a first gate of the sequence of the plurality of gates; determining, by the processing circuitry, that one or more conditions of the first gate are satisfied; determining, by the processing circuitry and in response to determining that each of the one or more conditions of the first gate are satisfied, that the first gate is completed; only after determining that the first gate is completed; outputting an indication that the clinical research study protocol is at a second gate of the sequence of the plurality of gates subsequent to the first gate.

Example 3E. The method of example 2E, wherein determining that one or more conditions of the first gate are satisfied comprises: receiving, via a user interface application executed by the processing circuitry and from one or more first users, data associated with the first gate; displaying, via the user interface application and to one or more second users, the data associated with the first gate; receiving, via the user interface application and from the one or more second users, an indication that the one or more conditions of the first gate are satisfied; transmitting, by the user interface application and to a microservice executed by the processing circuitry, the indication that the one or more conditions of the first gate are satisfied; and wherein determining, in response to determining that each of the one or more conditions of the first gate are satisfied, that the first gate is completed comprises: determining, by the microservice and in response to the indication from the user interface application that that the one or more conditions of the first gate are satisfied, that the first gate is completed.

Example 4E. The method of example 3E, wherein transmitting, by the user interface application and to the microservice, the indication that the one or more conditions of the first gate are satisfied comprises transmitting, by the user interface application and according to a guaranteed messaging protocol, the indication that the one or more conditions of the gate are satisfied.

Example 5E. The method of any of examples 1E through 4E, further comprising: outputting, by the processing circuitry, a representation of the sequence of the plurality of gates, wherein the representation of the sequence of the plurality of gates comprises: a representation of each gate of the sequence of the plurality of gates; and a representation of each condition of the one or more conditions of each gate of the sequence of the plurality of gates.

Example 6E. The method of example 5E, wherein the representation of the sequence of the plurality of gates further comprises a status of each gate of the sequence of the plurality of gates; and a status of each condition of the one or more conditions of each gate of the sequence of the plurality of gates.

Example 7E. The method of any of examples 5E through 6E, wherein the representation of the sequence of the plurality of gates comprises a grid representation of each gate of the sequence of the plurality of gates and each condition of the one or more conditions of each gate of the sequence of the plurality of gates.

Example 8E. The method of any of examples 5E through 7E, wherein outputting the representation of the sequence of the plurality of gates comprises outputting, for display on a dashboard of a web browser, the representation of the sequence of the plurality of gates.

Example 9E. The method of any of examples 1E through 8E, wherein each client business object specifies a plurality of processes (e.g., "swimlanes"), each process of the plurality of processes comprising an independent sequence of a plurality of gates for the clinical research study protocol.

Example 10E. The method of claim 9, wherein the sequence of the plurality of gates further comprises a closing gate for each process of the of the plurality of processes, such that completion of the closing gate for the corresponding process is indicative that the process has completed.

Example 11E. The method of any of examples 9E through 10E, wherein the plurality of processes comprise at least one of: a process comprising a sequence of a plurality of feasibility and recruitment stages for the clinical research study protocol; a process comprising a sequence of a plurality of Identification of Medicinal Products (IDMP) or Clinical Decision Rule (CDR) stages for the clinical research study protocol; a process comprising a sequence of a plurality of risk-based monitoring stages for the clinical research study protocol; a process comprising a sequence of a plurality of clinical development risk management stages for the clinical research study protocol; a process comprising a sequence of a plurality of medical standards stages for the clinical research study protocol; a process comprising a sequence of a plurality of environment for clinical data stages for the clinical research study protocol; a process comprising a sequence of a plurality of clinical supply mission stages for the clinical research study protocol; or a process comprising a sequence of a plurality of Clinical Trial Agreement (CTA) submission stages for the clinical research study protocol.

Example 12E. The method of any of examples 1E through 11E, further comprising receiving, by the processing circuitry and from a user, an input defining: at least one gate of the sequence of the plurality of gates; or at least one condition of the one or more conditions for at least one gate of the sequence of the plurality of gates.

Example 13E. A device comprising processing circuitry configured to: define a data model comprising metadata that specifies a data standard representative of requirements for regulatory-compliant exchange of data between entities, wherein the data model includes one or more client objects, each client object specifying a sequence of a plurality of gates for a process of a clinical research study protocol, wherein each gate of the plurality of gates defines one or more conditions for completion of the gate; and express the data model to define the clinical research study protocol.

Example 14E. The device of example 13E, configured to perform the method of any of examples 1E through 12E.

Example 15E. A system comprising the device of any of examples 13 through 14.

Example 16E. A non-transitory, computer-readable medium comprising instructions that, when executed, are configured to cause processing circuitry to: define a data model comprising metadata that specifies a data standard representative of requirements for regulatory-compliant exchange of data between entities, wherein the data model includes one or more client objects, each client object specifying a sequence of a plurality of gates for a process of a clinical research study protocol, wherein each gate of the plurality of gates defines one or more conditions for completion of the gate; and express the data model to define the clinical research study protocol.

Example 17E. The computer-readable medium of example 16E, wherein the processing circuitry is configured to perform the method of any of examples 1E through 12E.

Example 1F. A method comprising: receiving, by processing circuitry and from a user, an input specifying a plurality of trial elements for a study; receiving, by the processing circuitry and from the user, an input arranging the plurality of trial elements into a tree data structure; determining, by the processing circuitry based on the tree data structure of the plurality of trial elements, one or more trial arms for the study, each trial arm of the one or more trial arms comprising a single path between at least one trial element of the plurality of trial elements to at least one other trial element of the plurality of trial elements; and outputting, by the processing circuitry and for display, the one or more trial arms for the study.

Example 2F. The method of example 1F, wherein the method further comprises: displaying, by the processing circuitry, a graphical user interface comprising: a representation of a template area; a plurality of representations of trial elements positioned within the template area; and a representation of a workspace area;

Example 3F. The method of example 2F, wherein receiving the input specifying the plurality of trial elements for the study comprises: receiving, by the processing circuitry and from the user, an input from the user specifying movement of at least some of the plurality of the representations of trial elements from the representation of the template area to the representation of the workspace area.

Example 4F. The method of example 3F, wherein the input from the user specifying the movement of the at least some of the plurality of the representations of trial elements from the representation of the template area to the representation of the workspace area comprises an input specifying a drag-and-drop operation to move the at least some of the plurality of the representations of trial elements from the representation of the template area to the representation of the workspace area.

Example 5F. The method of any of examples 2F through 4F, wherein each representation of the plurality of the representations of trial elements comprise at least one anchor point, and wherein the input arranging the plurality of trial elements into a tree data structure comprises an input specifying a drag-and-drop operation to drag a connection between a first anchor point of a first representation of a first trial element of the plurality of the representations of trial elements to a second anchor point of a second representation of a second trial element of the plurality of the representations of trial elements, the input indicating a parent-child relationship of the first trial element to the second trial element.

Example 6F. The method of any of examples 1F through 5F, wherein outputting, for display, the one or more trial arms for the study comprises outputting, for display on a dashboard of a web browser, the one or more trial arms for the study.

Example 7F. The method of any of examples 1F through 7F, further comprising outputting, by the processing circuitry, at least one of: a trial arm dataset for the one or more trial arms for the study; or a trial element dataset for the one or more trial arms for the study Example 8F. The method of any of examples 1F through 7F, wherein receiving the input specifying the plurality of trial elements comprises receiving an input specifying a selection of a plurality of pre-defined trial elements for the study.

Example 9F. The method of any of examples 1F through 7F, wherein receiving the input specifying the plurality of trial elements comprises receiving an input defining a plurality of custom trial elements for the study.

Example 10F. The method of any of examples 1F through 9F, wherein determining, based on the tree data structure of the plurality of trial elements, the one or more trial arms for the study comprises: deterministically traversing of the tree data structure of the plurality of trial elements to obtain one or more paths from a root of the tree data structure to a unique leaf of the tree data structure; and defining, based on the one or more paths, the one or more trial arms for the study, each trial arm of the one or more trial arms corresponding to each path of the one or more paths.

Example 11F. The method of any of examples 1F through 10F, wherein the tree data structure comprises a single parent, single root tree data structure.

Example 12F. A device comprising processing circuitry configured to: receive, from a user, an input specifying a plurality of trial elements for a study; receive, from the user, an input arranging the plurality of trial elements into a tree data structure; determine, based on the tree data structure of the plurality of trial elements, one or more trial arms for the study, each trial arm of the one or more trial arms comprising a single path between at least one trial element of the plurality of trial elements to at least one other trial element of the plurality of trial elements; and output, for display, the one or more trial arms for the study.

Example 13F. The device of example 12F, further configured to perform the method of any of examples 1F through 11F.

Example 14F. A system comprising the device of any of examples 12F through 13F.

Example 15F. A non-transitory, computer-readable medium comprising instructions that, when executed, are configured to cause processing circuitry to: receive, from a user, an input specifying a plurality of trial elements for a study; receive, from the user, an input arranging the plurality of trial elements into a tree data structure; determine, based on the tree data structure of the plurality of trial elements, one or more trial arms for the study, each trial arm of the one or more trial arms comprising a single path between at least one trial element of the plurality of trial elements to at least one other trial element of the plurality of trial elements; and output, for display, the one or more trial arms for the study.

Example 16F. The computer-readable medium of example 15F, wherein the processing circuitry is configured to perform the method of any of examples 1F through 11F.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
receiving, by processing circuitry and from a user, an input specifying a plurality of trial elements for a study;
receiving, by the processing circuitry and from the user, an input arranging the plurality of trial elements into a tree data structure;
determining, by the processing circuitry based on the tree data structure of the plurality of trial elements, two or more trial arms for the study, each trial arm of the two or more trial arms comprising a single path between at least one trial element of the plurality of trial elements to at least one other trial element of the plurality of trial elements, wherein determining, based on the tree data structure of the plurality of trial elements, the two or more trial arms for the study comprises:
deterministically traversing of the tree data structure of the plurality of trial elements to obtain one or more paths from a root of the tree data structure to a unique leaf of the tree data structure; and defining, based on the one or more paths, the two or more trial arms for the study, each trial arm of the two or more trial arms corresponding to each path of the one or more paths; and outputting, by the processing circuitry and for display, the two or more trial arms for the study.

2. The method of claim 1, wherein the method further comprises: displaying, by the processing circuitry, a graphical user interface comprising:
a representation of a template area;
a plurality of representations of trial elements positioned within the template area; and
a representation of a workspace area.

3. The method of claim 2, wherein receiving the input specifying the plurality of trial elements for the study comprises:
receiving, by the processing circuitry and from the user, an input from the user specifying movement of at least some of the plurality of the representations of trial elements from the representation of the template area to the representation of the workspace area.

4. The method of claim 3, wherein the input from the user specifying the movement of the at least some of the plurality of the representations of trial elements from the representation of the template area to the representation of the workspace area comprises an input specifying a drag-and-drop operation to move the at least some of the plurality of the representations of trial elements from the representation of the template area to the representation of the workspace area.

5. The method of claim 2,
wherein each representation of the plurality of the representations of trial elements comprise at least one anchor point, and
wherein the input arranging the plurality of trial elements into the tree data structure comprises an input specifying a drag-and-drop operation to drag a connection between a first anchor point of a first representation of a first trial element of the plurality of the representations of trial elements to a second anchor point of a second representation of a second trial element of the plurality of the representations of trial elements, the input indicating a parent-child relationship of the first trial element to the second trial element.

6. The method of claim 5,
wherein the input specifying the plurality of trial elements for the study comprises a first input and the connection comprises a first connection,
wherein the input arranging the plurality of trial elements into the tree data structure further comprises a second input specifying the drag-and-drop operation to drag a connection between the first anchor point of the first representation of the first trail element to a third anchor point of a third representation of a third trial element,
wherein the method further comprises:
determining that the first trial element has connections to both the second trial element and the third trial element; and
refraining, responsive to determining that the first trial element has connections to both the second trial element and the third trial element, from generating the two or more trial arms until branch criteria has been specified.

7. The method of claim 1, wherein outputting, for display, the two or more trial arms for the study comprises outputting, for display on a dashboard of a web browser, the two or more trial arms for the study.

8. The method of claim 1, further comprising outputting, by the processing circuitry, at least one of:
a trial arm dataset for the two or more trial arms for the study; or
a trial element dataset for the two or more trial arms for the study.

9. The method of claim 1, wherein receiving the input specifying the plurality of trial elements comprises receiving an input specifying a selection of a plurality of pre-defined trial elements for the study.

10. The method of claim 1, wherein receiving the input specifying the plurality of trial elements comprises receiving an input defining a plurality of custom trial elements for the study.

11. The method of claim 1, wherein the tree data structure comprises a single parent, single root tree data structure.

12. A computing device comprising:
a memory configured to store a study; and
one or more processors configured to:
receive, from a user, an input specifying a plurality of trial elements for the study;
receive, from the user, an input arranging the plurality of trial elements into a tree data structure;
determine, based on the tree data structure of the plurality of trial elements, two or more trial arms for the study, each trial arm of the two or more trial arms comprising a single path between at least one trial element of the plurality of trial elements to at least one other trial element of the plurality of trial elements, wherein to determine, based on the tree data structure of the plurality of trial elements, the two or more trial arms for the study, the one or more processors are configured to:
deterministically traverse of the tree data structure of the plurality of trial elements to obtain one or more paths from a root of the tree data structure to a unique leaf of the tree data structure; and
define, based on the one or more paths, the two or more trial arms for the study, each trial arm of the two or more trial arms corresponding to each path of the one or more paths; and
output, for display, the two or more trial arms for the study.

13. The computing device of claim 12, where the one or more processors are further configured to display a graphical user interface comprising:
a representation of a template area;
a plurality of representations of trial elements positioned within the template area; and
a representation of a workspace area.

14. The computing device of claim 13, wherein the one or more processors are configured, when receiving the input specifying the plurality of trial elements for the study, to:
receive, from the user, an input from the user specifying movement of at least some of the plurality of the representations of trial elements from the representation of the template area to the representation of the workspace area.

15. The computing device of claim 14, wherein the input from the user specifying the movement of the at least some of the plurality of the representations of trial elements from the representation of the template area to the representation of the workspace area comprises an input specifying a drag-and-drop operation to move the at least some of the plurality of the representations of trial elements from the representation of the template area to the representation of the workspace area.

16. The computing device of claim 13,
wherein each representation of the plurality of the representations of trial elements comprise at least one anchor point, and
wherein the input arranging the plurality of trial elements into the tree data structure comprises an input specifying a drag-and-drop operation to drag a connection between a first anchor point of a first representation of a first trial element of the plurality of the representations of trial elements to a second anchor point of a second representation of a second trial element of the plurality of the representations of trial elements, the input indicating a parent-child relationship of the first trial element to the second trial element.

17. The computing device of claim 16,
wherein the input specifying the plurality of trial elements for the study comprises a first input and the connection comprises a first connection,
wherein the input arranging the plurality of trail elements into the tree data structure further comprises a second input specifying the drag-and-drop operation to drag a connection between the first anchor point of the first representation of the first trail element to a third anchor point of a third representation of a third trial element,
wherein the one or more processors are further configured to:
determine that the first trial element has connections to both the second trial element and the third trial element; and
refrain, responsive to determining that the first trial element has connections to both the second trial element and the third trial element, from generating the two or more trial arms until branch criteria has been specified.

18. The computing device of claim 12, wherein the one or more processors are configured, when outputting, for display, the two or more trial arms for the study, to output, for display on a dashboard of a web browser, the two or more trial arms for the study.

19. The computing device of claim 12, wherein the one or more processors are further configured to output at least one of:
a trial arm dataset for the two or more trial arms for the study; or
a trial element dataset for the two or more trial arms for the study.

20. The computing device of claim 12, wherein the one or more processors are configured, when receiving the input specifying the plurality of trial elements, to receive an input specifying a selection of a plurality of pre-defined trial elements for the study.

21. The computing device of claim 12, wherein the one or more processors are configured, when receiving the input specifying the plurality of trial elements, to receive an input defining a plurality of custom trial elements for the study.

22. The computing device of claim 12, wherein the tree data structure comprises a single parent, single root tree data structure.

23. A non-transitory, computer-readable medium comprising instructions that, when executed, are configured to cause processing circuitry to:
receive, from a user, an input specifying a plurality of trial elements for a study;
receive, from the user, an input arranging the plurality of trial elements into a tree data structure;
determine, based on the tree data structure of the plurality of trial elements, two or more trial arms for the study, each trial arm of the two or more trial arms comprising a single path between at least one trial element of the plurality of trial elements to at least one other trial element of the plurality of trial elements, wherein to determine, based on the tree data structure of the plurality of trial elements, the two or more trial arms for the study, the instructions, when executed cause the processing circuitry to:
deterministically traverse of the tree data structure of the plurality of trial elements to obtain one or more paths from a root of the tree data structure to a unique leaf of the tree data structure; and
define, based on the one or more paths, the two or more trial arms for the study, each trial arm of the two or more trial arms corresponding to each path of the one or more paths; and
output, for display, the one or more trial arms for the study.

* * * * *